US008716220B2

(12) United States Patent
Tezapsidis et al.

(10) Patent No.: US 8,716,220 B2
(45) Date of Patent: *May 6, 2014

(54) LEPTIN COMPOSITIONS AND METHODS FOR TREATING PROGRESSIVE COGNITIVE FUNCTION DISORDERS RESULTING FROM ACCUMULATION OF NEUROFIBRILLARY TANGLES AND AMYLOID BETA

(76) Inventors: Nikolaos Tezapsidis, West Orange, NJ (US); Steven J. Greco, Carlstadt, NJ (US); Mark Smith, Cleveland, OH (US)

(*) Notice: Subject to any disclaimer, the term of this patent is extended or adjusted under 35 U.S.C. 154(b) by 27 days.

This patent is subject to a terminal disclaimer.

(21) Appl. No.: 12/612,613

(22) Filed: Nov. 4, 2009

(65) Prior Publication Data

US 2010/0113358 A1 May 6, 2010

Related U.S. Application Data

(63) Continuation-in-part of application No. 12/470,427, filed on May 21, 2009, and a continuation-in-part of application No. 11/516,224, filed on Sep. 6, 2006.

(60) Provisional application No. 61/186,102, filed on Jun. 11, 2009, provisional application No. 61/111,197, filed on Nov. 4, 2008, provisional application No. 61/055,009, filed on May 21, 2008, provisional application No. 60/714,948, filed on Sep. 7, 2005.

(51) Int. Cl.
 *A61K 38/22* (2006.01)

(52) U.S. Cl.
 USPC .............................. 514/5.8; 514/17.8; 514/18.2

(58) Field of Classification Search
 None
 See application file for complete search history.

(56) References Cited

U.S. PATENT DOCUMENTS

| | | | |
|---|---|---|---|
| 4,105,027 A | 8/1978 | Lundquist |
| 4,192,309 A | 3/1980 | Poulsen |
| 4,227,522 A | 10/1980 | Carris |
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 5,521,283 A | 5/1996 | DiMarchi et al. |
| 5,552,522 A | 9/1996 | DiMarchi et al. |
| 5,552,523 A | 9/1996 | Basinski et al. |
| 5,552,524 A | 9/1996 | Basinski et al. |
| 5,698,389 A | 12/1997 | De La Brousse et al. |
| 5,756,461 A | 5/1998 | Stephens |
| 5,830,450 A | 11/1998 | Lallone |
| 6,001,816 A | 12/1999 | Morsy et al. |
| 6,001,968 A | 12/1999 | Friedman et al. |
| 6,020,004 A | 2/2000 | Shah |
| 6,025,324 A | 2/2000 | Bailon et al. |
| 6,025,325 A | 2/2000 | Campfield et al. |
| 6,048,837 A | 4/2000 | Friedman et al. |
| 6,068,976 A | 5/2000 | Briggs et al. |
| 6,284,221 B1 | 9/2001 | Schenk et al. |
| 6,309,853 B1 | 10/2001 | Friedman et al. |
| 6,352,970 B1 | 3/2002 | Ke et al. |
| 6,429,290 B1 | 8/2002 | Friedman et al. |
| 6,471,956 B1 | 10/2002 | Friedman et al. |
| 6,475,984 B2 | 11/2002 | Kirwin et al. |
| 6,518,235 B1 | 2/2003 | Oomura et al. |
| 6,630,346 B1 | 10/2003 | Morsy et al. |
| 6,716,810 B1 | 4/2004 | Brennan et al. |
| 6,777,388 B1 | 8/2004 | Grasso et al. |
| 6,921,527 B2 | 7/2005 | Platz et al. |
| 6,936,439 B2 | 8/2005 | Mann et al. |
| 7,074,397 B1 | 7/2006 | Matthews |
| 7,109,159 B1 | 9/2006 | Barkan et al. |
| 7,112,659 B2 | 9/2006 | Mann et al. |
| 7,183,254 B2 | 2/2007 | DePaoli et al. |
| 7,186,694 B2 | 3/2007 | Grasso et al. |
| 7,208,572 B2 | 4/2007 | Grasso et al. |
| 7,291,458 B2 | 11/2007 | Broekaert et al. |
| 7,307,142 B2 | 12/2007 | Gertler et al. |
| 7,354,896 B2 | 4/2008 | Kirwin et al. |
| 7,407,929 B2 | 8/2008 | Gonzalez et al. |
| 7,544,492 B1 | 6/2009 | Friedman et al. |
| 7,582,292 B2 | 9/2009 | Wilkison et al. |
| 7,612,043 B2 | 11/2009 | Gonzalez et al. |
| 7,629,315 B2 | 12/2009 | Zhao |
| 7,642,281 B2 | 1/2010 | Blackburn et al. |
| 7,786,265 B2 | 8/2010 | Grasso et al. |

(Continued)

FOREIGN PATENT DOCUMENTS

| | | |
|---|---|---|
| WO | 9116038 A1 | 10/1991 |
| WO | 9623513 A1 | 8/1996 |
| WO | 9623514 A1 | 8/1996 |
| WO | 9623515 A1 | 8/1996 |
| WO | 9623516 A1 | 8/1996 |
| WO | 9623517 A1 | 8/1996 |
| WO | 9623518 A1 | 8/1996 |
| WO | 9623519 A1 | 8/1996 |
| WO | 9623520 A1 | 8/1996 |
| WO | 9629405 A2 | 9/1996 |

(Continued)

OTHER PUBLICATIONS

Greco et al., Biochem. and Biophys. Res. Comm., 2008, 376, pp. 536-541.*

(Continued)

*Primary Examiner* — Olga N Chernyshev

(57) ABSTRACT

The present disclosure provides compositions containing a leptin product and methods of clinical therapy and diagnostic methods for progressive cognitive disorders. According to one aspect, the described invention provides a method for treating a progressive cognitive disorder. According to another aspect, the described invention provides a method for improving resilience of cognitive function in a subject in need thereof. According to another aspect, the described invention provides a method for identifying an effective therapeutic agent for treating a progressive cognitive dysfunction disease or disorder that results from at least one of accumulation of Aβ, hyperphosphorylation of tau, or accumulation of neurofibrillary tangles.

4 Claims, 20 Drawing Sheets

(56) References Cited

U.S. PATENT DOCUMENTS

| | | | |
|---|---|---|---|
| 7,790,683 B2 | 9/2010 | Grasso et al. | |
| 7,807,154 B2 | 10/2010 | Strasburger et al. | |
| 7,807,643 B2 | 10/2010 | Kirwin et al. | |
| 7,863,240 B2 | 1/2011 | Ilan et al. | |
| 8,227,408 B2 * | 7/2012 | Tezapsidis | 514/5.8 |
| 2002/0015709 A1 | 2/2002 | Kirwin et al. | |
| 2002/0019351 A1 | 2/2002 | Ke et al. | |
| 2002/0019352 A1 | 2/2002 | Brems et al. | |
| 2002/0107211 A1 | 8/2002 | Friedman et al. | |
| 2003/0036526 A1 | 2/2003 | Broekaert et al. | |
| 2003/0130192 A1 | 7/2003 | Kirwin et al. | |
| 2003/0215423 A1 | 11/2003 | Morsy et al. | |
| 2004/0043932 A1 | 3/2004 | Grasso et al. | |
| 2004/0053366 A1 | 3/2004 | Lo et al. | |
| 2004/0202652 A1 | 10/2004 | Karsenty et al. | |
| 2004/0213763 A1 | 10/2004 | Friedman et al. | |
| 2005/0020496 A1 | 1/2005 | DePaoli et al. | |
| 2005/0049193 A1 | 3/2005 | Grasso et al. | |
| 2005/0065078 A1 | 3/2005 | Cawthorne et al. | |
| 2005/0163799 A1 | 7/2005 | Mann et al. | |
| 2005/0250690 A1 | 11/2005 | Gonzalez et al. | |
| 2005/0272656 A1 | 12/2005 | Matthews | |
| 2006/0079442 A1 | 4/2006 | Ilan et al. | |
| 2006/0079443 A1 | 4/2006 | Ilan et al. | |
| 2006/0154859 A1 | 7/2006 | Gertler et al. | |
| 2006/0165683 A1 | 7/2006 | Karsenty et al. | |
| 2006/0205660 A1 | 9/2006 | De Sauvage et al. | |
| 2006/0206948 A1 | 9/2006 | Zhao | |
| 2006/0281699 A1 | 12/2006 | Merchiers et al. | |
| 2007/0066527 A1 | 3/2007 | Tezapsidis | |
| 2007/0099836 A1 | 5/2007 | DePaoli et al. | |
| 2007/0104697 A1 | 5/2007 | Wilkison et al. | |
| 2007/0135510 A1 | 6/2007 | Blackburn | |
| 2007/0162987 A1 | 7/2007 | Grasso et al. | |
| 2007/0218504 A1 | 9/2007 | Zhao | |
| 2008/0009475 A1 | 1/2008 | Garner et al. | |
| 2008/0108567 A1 | 5/2008 | Grasso et al. | |
| 2008/0118503 A1 | 5/2008 | Strasburger et al. | |
| 2008/0138811 A1 | 6/2008 | Mack et al. | |
| 2008/0242612 A1 | 10/2008 | Kirwin et al. | |
| 2009/0029919 A1 | 1/2009 | Gonzalez et al. | |
| 2009/0031434 A1 | 1/2009 | Han | |
| 2009/0175841 A1 | 7/2009 | Berry et al. | |
| 2009/0281522 A1 | 11/2009 | Thio et al. | |
| 2009/0291894 A1 | 11/2009 | Tezapsidis et al. | |

FOREIGN PATENT DOCUMENTS

| | | | |
|---|---|---|---|
| WO | 9724440 A1 | 7/1997 | |
| WO | 9748419 A1 | 12/1997 | |
| WO | 9748806 A1 | 12/1997 | |
| WO | 9824896 A2 | 6/1998 | |
| WO | 9846257 A1 | 10/1998 | |
| WO | 9951253 A2 | 10/1999 | |
| WO | 0009165 A1 | 2/2000 | |
| WO | 0011173 A1 | 3/2000 | |
| WO | 0020872 A1 | 4/2000 | |
| WO | 0033658 A1 | 6/2000 | |
| WO | 0040615 A2 | 7/2000 | |
| WO | 0047741 A1 | 8/2000 | |
| WO | 0076552 A1 | 12/2000 | |
| WO | 0113935 A2 | 3/2001 | |
| WO | 03020303 A1 | 3/2003 | |
| WO | 03034996 A2 | 5/2003 | |
| WO | 2005110461 A2 | 11/2005 | |
| WO | 2005110468 A2 | 11/2005 | |
| WO | 2006056987 A2 | 6/2006 | |
| WO | 2006096816 A2 | 9/2006 | |
| WO | 2008048691 A2 | 4/2008 | |
| WO | 2008115880 A2 | 9/2008 | |
| WO | 2008155403 A2 | 12/2008 | |
| WO | 2009019427 A2 | 2/2009 | |
| WO | 2009108340 A2 | 9/2009 | |
| WO | 2009138762 A2 | 11/2009 | |
| WO | 2010054017 A1 | 5/2010 | |
| WO | 2009143380 A2 | 11/2011 | |

OTHER PUBLICATIONS

Bor Luen Tang, 2008, Biochem. Biophys. Res. Comm., 368, pp. 181-185.*

Signore et al., 2008, J. Neurochem., 106, pp. 1977-1990.*

Fewlass et al., 2004, FASEB, 18, pp. 1870-1878.*

Tschape, J.-A. et al., "Therapeutic Perspectives in Alzheimer's Disease", Recent Pat. CNS Drug Discov., 2006, pp. 119-127, vol. 1, No. 1, Bentham Science Publishers Ltd.

Ulery, P.G. et al., "LRP in Alzheimer's Disease: Friend or Foe?", J. Clin. Invest., Nov. 2000, pp. 1077-1079, vol. 106, No. 9, The American Society for Clinical Investigation.

Unger, R.H., "The Physiology of Cellular Liporegulation", Annu. Rev. Physiol., 2003, pp. 333-347, vol. 65, Annual Reviews.

Unger, R.H., "Lipotoxic Diseases", Annu. Rev. Med., 2002, pp. 319-336, vol. 53, Annual Reviews.

Ur, E. et al., "Leptin Immunoreactivity is Localized to Neurons in Rat Brain", Neuroendocrinology, 2002, pp. 264-272, vol. 75, S. Karger AG, Basel.

Vickers, J.C., "A Vaccine Against Alzheimer's Disease: Developments to Date", Drugs Aging, 2002, pp. 487-494, vol. 19, No. 7, Adis International Limited.

Watson, G.S. et al. "The Role of Insulin Resistance in the Pathogenesis of Alzheimer's Disease: Implications for Treatment", CNS Drugs, 2003, pp. 27-45, vol. 17, No. 1, Adis International Limited.

Weng, Z. et al., "Leptin Protects Against 6-Hydroxydopamine-Induced Dopaminergic Cell Death via Mitogen-Activated Protein Kinase Signaling", J. Biol. Chem. Nov. 23, 2007, pp. 34479-34491, vol. 282, No. 47, The American Society for Biochemistry and Molecular Biology, Inc.

Wilentz, R.E. et al., "Lipogenic Enzymes Fatty Acid Synthase and Acetyl-Coenzyme A Carboxylase are Coexpressed with Sterol Regulatory Element Binding Protein and Ki-67 in Fetal Tissues", Pediatr. Dev. Pathol., 2000, pp. 525-531, vol. 3, Society for Pediatric Pathology.

Wood, W.G. et al., "Brain Membrane Cholesterol Domains, Aging and Amyloid Beta-Peptides", Neurobiol. Aging, 2002, pp. 685-694, vol. 23, Elsevier Science, Inc.

Xiao, E. et al., "Leptin Modulates Inflammatory Cytokine and Neuroendocrine Responses to Endotoxin in the Primate", Endocrinology, Oct. 2003, pp. 4350-4353, vol. 144, No. 10, The Endocrine Society.

Yanagisawa, M. et al, "Role of Lipid Rafts in Integrin-Dependent Adhesion and gp130 Signalling Pathway in Mouse Embryonic Neural Precursor Cells", Genes Cells, 2004, pp. 801-809, vol. 9, Blackwell Publishing Limited.

Ye, F. et al., "The Dipeptide H-Trp-Glu-OH Shows Highly Antagonistic Activity Against PPARgamma: Bioassay with Molecular Modeling Simulation", Chembiochem, 2006, pp. 74-82, vol. 7, Wiley-VCH Verlag GmbH & Co. KGaA, Weinheim.

Yu, Y.-H. et al., "Posttrascriptional Control of the Expression and Function of Diacylglycerol Acyltransferase-1 in Mouse Adipocytes", J. Biol. Chem., Dec. 27, 2002, pp. 50876-50884, vol. 277, No. 52, The American Society for Biochemistry and Molecular Biology, Inc.

Zarkesh-Esfahani, H. et al., "High-Dose Leptin Activates Human Leukocytes Via Receptor Expression on Monocytes", J. Immunol., 2001, pp. 4593-4599, vol. 167, The American Association of Immunologists, Inc., Bethesda, MD.

Zhang, F et al., "Neuroprotective effects of Leptin Against Ischemic Injury Induced by Oxygen-Glucose Deprivation and Transient Cerebral Ischemia", Stroke, Aug. 2007, pp. 2329-2336, vol. 38, American Heart Association, Inc.

Zhao, Y. et al., "Expression of Leptin Receptors and Response to Leptin Stimulation of Human Natural Killer Cell Lines", Biochem. Biophys. Res. Commun., 2003, pp. 247-252, vol. 300, Elsevier Science (USA), Academic Press.

(56) References Cited

OTHER PUBLICATIONS

Zhou, G. et al., "Role of AMP-Activated Protein Kinase in Mechanism of Metformin Action", J. Clin. Invest., Oct. 2001, pp. 1167-1174, vol. 108, No. 8, The American Society for Clinical Investigation.

American Psychiatric Association, "Diagnostic Criteria for Dementia of the Alzheimer's Type", Diagnostic and Statistical Manual of Mental Disorders, Fourth Edition, 1994, Copyright American Psychiatric Association.

Arnalich, F. et al., "Relationship of Plasma Leptin to Plasma Cytokines and Human Sepsis and Septic Shock", J. Infect. Dis., 1999, pp. 908-911, vol. 180, The Infectious Diseases Society of America.

Barrett-Connor, E. et al., "Weight Loss Precedes Dementia in Community-Dwelling Older Adults", J. Am. Geriatr. Soc., Oct. 1996, pp. 1147-1152, vol. 44, No. 10, Blackwell Publishing.

Batterham, R.L. et al., "Inhibition of Food Intake in Obese Subjects by Peptide YY3-36", N. Engl. J. Med., Sep. 4, 2003, pp. 941-948 vol. 349, No. 10, Massachusetts Medical Society.

Baumann, H. et al., "The Full-Length Leptin Receptor has Signaling Capabilities of Interleukin 6-Type Cytokine Receptors", Proc. Natl. Acad. Sci. USA, Aug. 1996, pp. 8374-8378, vol. 93, The National Academy of Sciences.

Benveniste, E.N. et al., "Immunological Aspects of Microglia: Relevance to Alzheimer's Disease", Neurochem. Int., 2001, pp. 381-391, vol. 39, Elsevier Science, Ltd.

Bickel, P.E. et al., "Flotillin and Epidermal Surface Antigen define a New Family of Caveolae-Associated Integral Membrane Proteins", J. Biol. Chem., May 23, 1997, pp. 13793-137802, vol. 272, No. 21, The American Society for Biochemistry and Molecular Biology, Inc.

Bilancio, A. et al., "Key Role of the p110Delta Isoform of PI3K in B-cell Antigen and IL-4 Receptor Signaling: Comparative Analysis of Genetic and Pharmacologic Interference with p110Delta Function in B Cells", Blood, 2006, pp. 642-650, vol. 107, No. 2, The American Society of Hematology, Washington DC.

Bjorbaek, C. et al., "The Role of SOCS-3 in Leptin Signaling and Leptin Resistance", J. Biol. Chem., Oct. 15, 1999, pp. 30059-30065, vol. 274, No. 42, The American Society for Biochemistry and Molecular Biology, Inc.

Blasko, I. et al., "TNFalpha Plus IFNgamma Induce the Production of Alzheimer Beta-Amyloid Peptides and Decrease the Secretion of APPs", FASEB J., Jan. 1999, pp. 63-68, vol. 13, The Federation of American Societies for Experimental Biology.

Bor Luen Tang, "Leptin as a neuroprotective agent", Biochem. Biophys. Res. Commun., Apr. 4, 2008, pp. 181-185, vol. 368, No. 2, Elsevier Inc.

Bradford, M.M., "A Rapid and Sensitive Method for the Quantitation of Microgram Quantities of Protein Utilizing the Principle of Protein-Dye Binding", Anal. Biochem., May 7, 1976, pp. 248-254, vol. 72, No. 1-2, Elsevier B.V.

Brown, M.S. et al., "The SREBP Pathway: Regulation of Cholesterol Metabolism by Proteolysis of a Membrane-Bound Transcription Factor", Cell, May 2, 1997, pp. 331-340, vol. 89, Cell Press.

Caldefie-Chezet, F. et al., "Leptin: A Potential Regulator of Polymorphonuclear Neutrophil Bactericidal Action", J. Leukoc. Biol., Mar. 2001, pp. 414-418, vol. 69, The Society of Leukocyte Biology.

Carpino, L.A. et al., "The 9-Fluorenylmethoxycarbonyl Amino-Protecting Group", J. Org. Chem., 1972, pp. 3404-3409, vol. 37, American Chemical Society.

Chen, F. et al., "Characterization of ATP-Independent ERK Inhibitors Indentified Through Silico Analysis of the Active ERK2 Structure", Bioorg. Med. Chem. Lett., 2006, pp. 6281-6287, vol. 16, Elsevier, Ltd.

Cheng, A.N. et al., "Attenuation of Leptin Action and Regulation of Obesity by Protein Tyrosine Phosphatase 1B", Dev. Cell, Apr. 2002, pp. 497-503, vol. 2, Cell Press.

Chung, W.K. et al., "Heterozygosity for Lep/ob or Lepr/db Affects Body Composition and Leptin Homeostasis in Adult Mice", Am. J. Physiol. Regul. Integr. Comp. Physiol., 1998, pp. R985-R990, vol. 274, The American Physiological Society, Bethesda, MD.

Clare, P.M. et al., "The Cyclin-Dependent Kinases cdk2 and cdk5 Act by a Random, Anticooperative Kinetic Mechanism", J. Biol. Chem., Dec. 21, 2001, pp. 48292-48299, vol. 276, No. 51, The American Society for Biochemistry and Molecular Biology, Inc.

Conway, K.A. et al., "Fibrils Formed in Vitro from alpha-Synuclein and Two Mutant Forms Linked to Parkinson's Disease are Typical Amyloid", Biochemistry, 2000, pp. 2552-2563, vol. 39, American Chemical Society.

Cordy, J.M. et al., "Exclusively Targeting (beta}-Secretase to Lipid Rafts by GPI-Anchor Addition Up-regulates (beta)-Site Processing of the Amyloid Precursor Protein", Proc. Natl. Acad. Sci. USA., Sep. 30, 2003, pp. 11735-11740, vol. 100, The National Academy of Sciences.

Counce, M.E. et al., "Localization of Leptin Receptor in the Human Brain", Neuroendocrinology, Sep. 1997, pp. 145-150, vol. 66, S. Karger AG, Basel.

Danik, M. et al., "Brain Lipoprotein Metabolism and Its Relation to Neurodegenerative Disease", Crit. Rev. Neurobiol., 1999, pp. 357-407, vol. 13, No. 4, Begell House, Inc. Publishers.

De Laszlo, S.E. et al., "Pyrroles and Other Heterocycles as Inhibitors of P38 Kinase", Bioorg. Med. Chem. Lett., 1998, pp. 2689-2694, vol. 8, Elsevier B.V.

De Strooper, B., "Aph-1, Pen-2, and Nicastrin with Presenilin Generate an Active gamma-Secretase Complex", Neuron, Apr. 10, 2003, pp. 9-12, vol. 38, Cell Press.

Doherty, G.H. et al., "Neuroprotective actions of leptin on central and peripheral neurons in vitro", Neuroscience, Jul. 17, 2008, pp. 1297-13-7, vol. 154, No. 4, Elsevier Ltd.

Duff, K. et al., "Increased Amyloid-beta42(43) in Brains of Mice Expressing Mutant Presenilin 1", Nature, Oct. 1996, pp. 710-713, vol. 383, The Nature Publishing Group.

Emmerling, M.R. et al., "The Role of Complement in Alzheimer's Disease Pathology", Biochim. Biophys. Acta, 2000, pp. 158-171, vol. 1502, Elsevier B.V.

Fagan, A.M. et al., "Unique Lipoproteins Secreted by Primary Astrocytes from Wild Type, apoE(−/−), and Human apoE Transgenic Mice", J. Biol. Chem., Oct. 15, 1999, pp. 30001-30007, vol. 274, The American Society for Biochemistry and Molecular Biology.

Faggioni, R. et al., "Leptin Regulation of the Immune Response and the Immunodeficiency of Malnutrition", FASEB J., Dec. 2001, pp. 2565-2571, vol. 15, The Federation of American Societies for Experimental Biology.

Farr, S.A. et al., "Effects of Leptin on Memory Processing", Peptides, 2006, pp. 1420-1425, vol. 27, Elsevier, Inc.

Farris, W. et al., "Insulin-Degrading Enzyme Regulates the Levels of Insulin, Amyloid Beta-Protein, and the Beta-Amyloid Precursor Protein Intracellular Domain in vivo", Proc. Natl. Acad. Sci. USA., Apr. 1, 2003, pp. 4162-1467, vol. 100, The National Academy of Sciences.

Feng, B. et al., "The Endoplasmic Reticulum is the Site of Cholesterol-Induced Cytotoxicity in Macrophages", Nat. Cell Biol., 5:781-792 (2003).

Fewlass, D.C. et al., "Obesity-Related Leptin Regulates Alzheimer's Abeta", FASEB J., Dec. 2004, pp. 1870-1878, vol. 18, The Federation of American Societies for Experimental Biology.

Fields, G.B. et al., "Solid Phase Peptide Synthesis Utilizing 9-Fluorenylmethoxycarbonyl Amino Acids", Int. J. Pept. Protein Res., 1990, pp. 161-214, vol. 35, John Wiley & Sons, Inc.

Figueiredo-Pereira, M.E. et al., "Distinct Secretases, a Cysteine Protease and a Serine Protease, Generate the C Termini of Amyloid Beta-Proteins Abeta1-40 and Abeta1-42, respectively", J. Neurochem., 1999, pp. 1417-1422, vol. 72, Lippincott Williams & Wilkins, Inc., Philadelphia, International Society for Neurochemistry.

Ford, M.J. et al., "Selective Expression of Prion Protein in Peripheral Tissues of the Adult Mouse", Neuroscience, 2002, pp. 177-192, vol. 113, No. 1, Elsevier Science, Ltd.

Frenkel, D. et al., "Nasal Vaccination with a Proteasome-Based Adjuvant and Glatiramer Acetate Clears beta-Amyloid in a Mouse Model of Alzheimer Disease", J. Clin. Invest., Sep. 2005, pp. 2423-2433, vol. 115, No. 9, The American Society for Clinical Investigation.

(56) References Cited

OTHER PUBLICATIONS

Gandy, S. "The Role of Cerebral Amyloid beta Accumulation in Common Forms of Alzheimer Disease", J. Clin. Invest., May 2005, pp. 1121-1129, vol. 115, No. 5, The American Society for Clinical Investigation.

Ghosh, T.K. et al., "Transdermal and Topical Drug Delivery Systems", 2007, pp. 249-297, Culinary and Hospitality Industry Publications Services.

Han, Z. et al., "c-Jun N-Terminal Kinase is Required for Metalloproteinase Expression and Joint Destruction in Inflammatory Arthritis", J. Clin. Invest., Jul. 2001, pp. 73-81, vol. 108, No. 1, The American Society for Clinical Investigation.

Hardy, J. et al., "The Amyloid Hypothesis of Alzheimer's Disease: Progress and Problems on the Road to Therapeutics", Science, Jul. 19, 2002, pp. 353-356, vol. 297, American Association for the Advancement of Science.

Heshka, J.T. et al., "A Role for Dietary Fat in Leptin Receptor, OB-Rb Function", Life Sci., 2001, pp. 987-1003, vol. 69, Elsevier, Inc.

Holcomb, L. et al., "Accelerated Alzheimer-Type Phenotype in Transgenic Mice Carrying Both Mutant Amyloid Precursor Protein and Presenilin 1 Transgenes", Nat. Med. Jan. 1998, pp. 97-100, vol. 4, No. 1, Nature Publishing Group.

Hsiao, K. et al., "Correlative Memory Deficits, Abeta Elevation, and Amyloid Plaques in Transgenic Mice", Science, Oct. 4, 1996, pp. 99-102, vol. 274, American Association for the Advancement of Science.

Hu, Y. et al., "3-(Hydroxymethyl)-Bearing Phosphatidylinositol Ether Lipid Analogues and Carbonate Surrogates Block P13-K, Akt, and Cancer Cell Growth", J. Med. Chem., 2000, pp. 3045-3051, vol. 43, No. 16, American Chemical Society.

Idris, I. et al., "Familial Hyperinsulinaemia Associated with Epilepsy and Mental Retardation—A Syndrome of Familial Insulin Resistance", Diabet. Med., 2004, pp. 628-631, vol. 21, Diabetes, UK.

International Search Report for PCT/US09/63310 dated Feb. 25, 2010.

Ishida, A. et al., "Stabilization of Calmodulin-Dependent Protein Kinase II Through the Autoinhibitory Domain", J. Biol. Chem., Feb. 3, 1995, pp. 2163-2170, vol. 270, No. 5, The American Society for Biochemistry and Molecular Biology, Inc.

Isidori, A.M. et al., "Leptin and Aging: Correlation with Endocrine Changes in Male and Female Healthy Adult Populations of Different Body Weights", J. Clin. Endocrinol. Metab., 2000, pp. 1954-1962, vol. 85, No. 5, The Endocrine Society.

Han, B. S. et al., "A distinct death mechanism is induced by 1-methyl-4-phenylpyridinium or by 6-hydroxydopamine in cultured rat cortical neurons: degradation and dephosphorylation of tau,", Neurosci Lett., May 1, 2003, 341(2): 99-102.

Mesulam, M. M., "A plasticity-based theory of the pathogenesis of Alzheimer's disease," Ann N Y Acad Sci. 2000; 924:42-52.

Muma, N. A. et al., "6-hydroxydopamine-induced lesions of dopaminergic neurons alter the function of postsynaptic cholinergic neurons without changing cytoskeletal proteins," Exp Neurol., Mar. 2001;168(1): 135-43.

Torack, R. M. et al., "Hippocampal pyramidal cell response to 6-hydroxydopamine lesions of the rat ventral tegmental area," Brain Res. Mar. 6, 1992; 574(1-2):345-8.

Bancher C. et al., "Accumulation of abnormally phosphorylated tau precedes the formation of neurofibrillary tangles in Alzheimer's disease." Brain Res., 1989, 477(1-2):90-9.

Greco et al., "Leptin regulates tau phosphorylation and amyloid through AMPK in neuronal cells" Biochemical and Biophysical Research Communications 380: 98-104 (2009).

Johnsingh, A.A. et al., "Altered Binding of Mutated Presenilin with Cytoskeleton-Interacting Proteins", FEBS Lett., 2000, pp. 53-58, vol. 465, Elsevier B.V., Federation of European Biochemical Societies.

Kang, D.E. et al., "Modulation of Amyloid Beta-Protein Clearance and Alzheimer's Disease Susceptibility by the LDL Receptor-Related Protein Pathway", J. Clin. Invest., Nov. 2000, pp. 1159-1166, vol. 106, No. 9, The American Society for Clinical Investigation.

Kase, H. et al., "K-252 Compounds, Novel and Potent Inhibitors of Protein Kinase C and Cyclic Nucleotide-Dependent Protein Kinases", Biochem. Biophys. Res. Commun., Jan. 30, 1987, pp. 436-440, vol. 142, No. 2, Academic Press, Inc.

Kawarabayashi, T. et al., "Age-Dependent Changes in Brain, CSF, and Plasma Amyloid beta Protein in the Tg2576 Transgenic Mouse Model of Alzheimer's Disease", J. Neurosci., Jan. 15, 2001, pp. 372-381, vol. 21, No. 2, Society for Neuroscience.

Kawarabayashi, T. et al., "Dimeric Amyloid beta Protein Accumulates in Lipid Rafts Followed by Apolipoprotein E and Phosphorylated Tau Accumulattion in the Tg2576 Mouse Model of Alzheimer's Disease", J. Neurosci., Apr. 14, 2004, pp. 3801-3809, vol. 24, No. 15, Society for Neuroscience.

Kempen, H.J. et al., "Secretion of Apolipoproteins A-I and B by HepG2 Cells: Regulation by Substrates and Metabolic Inhibitors", J. Lipid Res., 1995, pp. 1796-1806, vol. 36, The American Society for Biochemistry and Molecular Biology, Inc.

Kersten, S. "Mechanisms of Nutritional and Hormonal Regulation of Lipogenesis", EMBO Rep., 2001, pp. 282-286, vol. 2, No. 41, European Molecular Biology Organization.

King, T.D. et al., "AMP-Activated Protein Kinase (AMPK) Activating Agents Cause Dephosphorylation of Akt and Glycogen Synthase Kinase-3", Biochem. Pharmacol., 2006, pp. 1637-1647, vol. 71, Elsevier B.V.

Klein, P.S. et al., "A Molecular Mechanism for the Effect of Lithium on Development", Proc. Natl. Acad. Sci. USA, Aug. 1996, pp. 8455-8459, vol. 93, The National Academy of Sciences.

Kotilinek, L.A. et al., "Reversible Memory Loss in a Mouse Transgenic Model of Alzheimer's Disease", J. Neurosci., Aug. 1, 2002, pp. 6331-6335, vol. 22, No. 15, Society for Neuroscience.

Ladu, M.J. et al., "Apolipoprotein E and Apolipoprotein E Receptors Modulate A Beta-Induced Glial Neuroinflammatory Responses", Neurochem. Int., 2001, pp. 427-434, vol. 39, Elsevier Science, Ltd.

Langer, R., "New Methods of Drug Delivery", Science, Sep. 28, 1990, pp. 1527-1533, vol. 249, American Association for the Advancement of Science.

Lee, Y. et al., "Liporegulation in Diet-Induced Obesity: The Antisteatotic Role of Hyperleptinemia", J. Biol. Chem., Feb. 23, 2001, pp. 5629-5635, vol. 276, No. 8, The American Society for Biochemistry and Molecular Biology, Inc.

Lemaire-Vieille, C. et al., "Epithelial and Endothelial Expression of the Green Fluorescent Protein Reporter Gene Under the Control of Bovine Prion Protein (PrP) Gene Regulatory Sequences in Transgenic Mice", Proc. Natl. Acad. Sci. USA., May 9, 2000, pp. 5422-5427, vol. 97, No. 10, The National Academy of Sciences.

Lichtenthaler, S.F. et al., "Amyloid at the Cutting Edge: Activation of Alpha-Secretase Prevents Amyloidogenesis in an Alzheimer Disease Mouse Model", J. Clin. Invest., May 2004, pp. 1384-1387, vol. 113, No. 10, The American Society for Clinical Investigation.

Loftus, T.M. et al., "Reduced Food Intake and Body Weight in Mice Treated with Fatty Acid Synthase Inhibitors", Science, Jun. 30, 2000, pp. 2379-2381, vol. 288, American Association for the Advancement of Science.

Lord, G.M. et al., "Leptin Modulates the T-Cell Immune Response and Reverses Starvation-Induced Immunosuppression", Nature, Aug. 27, 1998, pp. 897-901, vol. 394, Nature Publishing Group, Macmillan Publishers, Ltd.

Martin-Romero, C. et al., "Human Leptin Activates P13K and MAPK Pathways in Human Peripheral Blood Mononuclear Cells: Possible Role of Sam68", Cell. Immunol., 2001, pp. 83-91, vol. 212, Elsevier Science, Ltd.

Matarese, G. et al., "Leptin in Immunology", J. Immunol., 2005, pp. 3137-3142, vol. 174, The American Association of Immunologists, Inc.

Mazzali, G. et al., "Energy Balance in Alzheimer's Disease", J. Nutr. Health Aging, 2002, pp. 247-253, vol. 6, No. 4, Springer.

McGowen, D.P. et al., "Amyloid-like Inclusions in Huntington's Disease", Neuroscience, 2000, pp. 677-680, vol. 100, No. 4, Elsevier Science, Ltd, Great Britain.

Merrifield, R.B., "Solid Phase Peptide Synthesis. I. The Synthesis of a Tetrapeptide", J. Am. Chem. Soc., Jul. 20, 1963, pp. 2149-2154, vol. 85, American Chemical Society.

(56) References Cited

OTHER PUBLICATIONS

Minokoshi, Y. et al., "Leptin Stimulates Fatty-Acid Oxidation by Activating AMP-Activated Protein Kinase", Nature, Jan. 17, 2002, pp. 339-343, vol. 415, Macmillan Magazines, Ltd.

Mobbs, C.V. et al., "Block the FAS, Loose the Fat", Nat. Med., Apr. 2002, pp. 335-336, vol. 8, No. 4, Nature Publishing Group.

Narita, M. et al., "Cellular Catabolism of Lipid Poor Apolipoprotein E Via Cell Surface LDL Receptor-Related Protein", J. Biochem., pp. 743-749, vol. 132, No. 5, The Japanese Biochemical Society, 2002.

Peterson, T.A. et al., "Design, Development, Manufacturing, and Testing of Transdermal Drug Delivery Systems", Transdermal and Topical Drug Delivery Systems, 1997, pp. 249-297, Interpharm Press, Inc.

Postina, R. et al., "A Disintegrin-Metalloproteinase Prevents Amyloid Plaque Formation and Hippocampal Defects in an Alzheimer Disease Mouse Model", J. Clin. Invest., May 2004, pp. 1456-1464, vol. 113, No. 10, The American Society for Clinical Investigation.

Puglielli, L. et al., "Acyl-Coenzyme A: Cholesterol Acyltransferase Modulates the Generation of the Amyloid Beta-Peptide", Nat. Cell Biol., Oct. 2001, pp. 905-912, vol. 3, Macmillan Magazines Ltd.

Purves, D. et al., (Eds.) Neuroscience, 2001, Sinauer Associates, Inc., 2nd Edition, pp. 403, 554, 555 and 678.

Qiu, W.Q. et al., "Degradation of Amyloid Beta-Protein by a Metalloprotease Secreted by Microglia and other Neural and Non-neural Cells", J. Biol. Chem., Mar. 7, 1997, pp. 6641-6646, vol. 272, No. 10, The American Society for Biochemistry and Molecular Biology, Inc.

Refolo, L.M. et al., "Hypercholesterolemia Accelerates the Alzheimer's Amyloid Pathology in a Transgenic Mouse Model", Neurobiol. Dis., 2000, pp. 321-331, vol. 7, Academic Press.

Sanchez-Margelet, V. et al., "Human Leptin Signaling in Human Peripheral Blood Mononuclear Cells: Activation of the JAK-STAT Pathway", Cell. Immunol., 2001, pp. 30-36, vol. 211, Academic Press.

Schindler, C., "Transcriptional Responses to Polypeptide Ligands: The JAK-STAT Pathway", Ann. Rev. Biochem., 1995, pp. 621-651, vol. 64, Annual Reviews, Inc.

Schwartz, M.W. et al., "Central Nervous System Control of Food Intake", Nature, Apr. 6, 2000, pp. 661-671, vol. 404, MacMillan Magazines Ltd.

Shanley, L.J. et al., "Leptin Inhibits Rat Hippocampal Neurons Via Activation of Large Conductance Calcium-Activated K+ channels", Nat. Neurosci., Apr. 2002, pp. 299-300, vol. 5, No. 4, Nature Publishing Group.

Shimano, H. et al., "Isoform 1c of Sterol Regulatory Element Binding Protein is Less Active Than Isoform 1a in Livers of Transgenic Mice and in Cultured Cells", J. Clin. Invest., Mar. 1997, pp. 846-854, vol. 99, No. 5, The American Society for Clinical Investigation, Inc.

Shimoda, K. et al., "A High Percentage Yield of Tyrosine Hydroxylase-Positive Cells from Rat E14 Mesencephalic Cell Culture", Brain Res., Jul. 24, 1992, pp. 319-331, vol. 586, No. 2, Elsevier B.V.

Shimomura, I. et al., "Increased Levels of Nuclear SREBP-1c Associated with Fatty Livers in Two Mouse Models of Diabetes Mellitus", J. Biol. Chem., Oct. 15, 1999, pp. 30028-30032, vol. 274, No. 42, The American Society for Biochemistry and Molecular Biology, Inc.

Siddiquee, K. et al., "Selective Chemical Probe Inhibitor of Stat3, Identified Through Structure-Based Virtual Screening, Induces Antitumor Activity", Proc. Natl. Acad. Sci. USA, May 1, 2007, pp. 7391-7396, vol. 104, No. 18, The National Academy of Sciences.

Simons, M. et al., "Cholesterol Depletion Inhibits the Generation of Beta-Amyloid in Hippocampal Neurons", Proc. Natl. Acad. Sci. USA., May 1998, pp. 6460-6464, vol. 95, The National Academy of Sciences.

Sirtori, C.R. et al., "Re-evaluation of a Biguanide, Metformin: Mechanism of Action and Tolerability", Pharmacol. Res., 1994, pp. 187-228, vol. 30, No. 3, The Italian Pharmacological Society.

Sleeman, M.W. et al., "The Ciliary Neurotrophic Factor and its Receptor, CNTFR Alpha", Pharm. Acta Helv., 2000, pp. 265-272, vol. 74, Elsevier B.V.

Smith, J.L. et al., "Levadopa with Carbidopa Diminishes Glycogen Concentration, Glycogen Synthase Activity, and Insulin-Stimulated Glucose Transport in Rat Skeletal Muscle", J. Appl. Physiol., Dec. 2004, pp. 2339-2346, vol. 97, The American Physiological Society.

Takeshima, T. et al., "Standardized Methods to Bioassay Neurotrophic Factors for Dopaminergic Neurons", J. Neurosci. Methods, 1996, pp. 27-41, vol. 67, Elsevier B.V.

Takeshima, T. et al., "Mesencephalic Type 1 Astrocytes Rescue Dopaminergic Neurons from Death Induced by Serum Deprivation", J. Neurosci., Aug. 1994, pp. 4769-4779, vol. 14, The Society for Neuroscience.

Tartaglia, L.A., "The Leptin Receptor", J. Biol. Chem., Mar. 7, 1997, pp. 6093-6096, vol. 272, No. 10, The American Society for Biochemistry and Molecular Biology.

Tezapsidis, N. et al., "Microtubular Interactions of Presenilin Direct Kinesis of aBeta Peptide and its Precursors", FASEB J., Jul. 2003, pp. 1322-1324, vol. 17, The Federation of American Societies for Experimental Biology.

Tomas, E. et al., "Enhanced Muscle Fat oxidation and Glucose Transport by ACRP30 Globular Domain:acetyl-coA Carboxylase Inhibition and AMP-Activated Protein Kinase Activation", Proc. Natl. Acad. Sci. USA., Dec. 10, 2002, pp. 16309-16313, vol. 99, The National Academy of Sciences.

Toyoshima, Y. et al., "Leptin Improves Insulin Resistance and Hyperglycemia in a Mouse Model of Type 2 Diabetes", Endocrinology, Sep. 2005, pp. 4024-4035, vol. 146, No. 9, The Endocrine Society.

Truett, G.E. et al., "Rat Obesity Gene Fatty (fa) Maps to Chromosome 5: Evidence for Homology with the Mouse Gene Diabetes (db)", Proc. Natl. Acad. Sci., USA, Sep. 1991, pp. 7806-7809, vol. 88, The National Academy of Sciences.

\* cited by examiner

LEPTIN COMPOSITIONS AND METHODS FOR TREATING PROGRESSIVE COGNITIVE FUNCTION DISORDERS RESULTING FROM ACCUMULATION OF NEUROFIBRILLARY TANGLES AND AMYLOID BETA

CROSS REFERENCE TO RELATED APPLICATIONS

This application claims the benefit of priority of U.S. application 61/186,102 (filed Jun. 11, 2009), and U.S. Application No. 61/111,197 (filed Nov. 4, 2008). The content of each of these applications is incorporated by reference in its entirety. This application is also a continuation-in-part of U.S. application Ser. No. 12/470,427 (filed May 21, 2009), which claims the benefit of priority from U.S. Provisional Application No. 61/055,009 (filed May 21, 2008) and is a continuation-in-part of U.S. application Ser. No. 11/516,224 (filed Sep. 6, 2006), which claims the benefit of priority from U.S. Provisional Application No. 60/714,948 (filed Sep. 7, 2005).

STATEMENT OF GOVERNMENT FUNDING

This invention was made with support under SBIR-1R43AG029670 awarded by the National Institute on Aging and the New Jersey Commission on Science and Technology. The government has certain rights in the invention.

FIELD OF USE

The described invention relates to compositions and methods for treating progressive cognitive function disorders resulting from accumulation of neurofibrillary tangles or amyloid beta utilizing a leptin product.

BACKGROUND OF THE INVENTION

Amyloid β (Aβ)

Amyloid β is derived from its large precursor protein (APP) by sequential proteolytic cleavages. APP is a single transmembrane polypeptide that is cotranslationally translocated into the endoplasmic recticulum via its signal peptide and then posttranslationally modified throught the secretory pathway. It comprises a heterogeneous group of ubiquitously expressed polypeptides. This heterogeneity arises both from alternative splicing (yielding 3 major isoforms of 695, 751 and 770 residues) as well as from a variety of posttranslational modifications, including the addition of N- and O-linked sugars, sulfation, and phosphorylation. Its acquisition of N- and O-linked sugars occurs rapidly after biosynthesis, and its half-life is relatively brief (45 to 60 minutes). Notwithstanding this heterogeneity, APP is highly conserved in evolution and is expressed in all mammals examined for it; a partial homolog of APP has been found in Drosophilia (APPL). APP is a member of a larger gene family, the amyloid precursor-like proteins (APLPs) which have substantial homology, both within the large ectodomain and the cytoplasmic tail, but are divergent in the Aβ region.

The APP splice forms containing 751 or 770 amino acids are widely expressed in normeuronal cells throughout the body and also occur in neurons. However, neurons express even higher levels of the 695 residue isoform, which occurs at very low abundance in normeuronal cells. The difference between the 751/770-residue and 695-residue forms is the presence in the 751/770-residue isoform of an exon that codes for a 56-amino acid motif that is homologous to the Kunitz-type of serine protease inhibitors (KPI), indicating one potential function of these longer APP isoforms. The KPI-containing isoforms of APP found in human platelets serve as inhibitors of factor Xia, which is a serine protease in the coagulation cascade.

Aβ production is a normal metabolic event Both during and after the trafficking of APP through the secretory pathway, APP can undergo a variety of proteolytic cleavages to release secreted derivatives into vesicle lumens and the extracellular space. The first proteolytic cleavage identified, that made by an activity designated α-secretase, occurs 12 amino acids $NH_2$-terminal to the single transmembrane domain of APP. This processing results in the release of the large soluble ectodomain fragment (α-$APP_s$) into the lumen/extracellular space and retention of an 83-residue COOH-terminal fragment (CTF) in the membrane. Alternatively, some APP molecules not subjected to α-secretase cleavage can be cleaved by an activity designated β-secretase, which principally cuts 16 residues $NH_2$-terminal to the α-cleavage site, generating a slightly smaller ectodomain derivative (β-$APP_s$) and retaining a 99-residue CFT (C99) in the membrane that begins at residue 1 of the Aβ region. The C99 fragment is consequently cleaved in the middle of the transmembrane domain as a result of γ-secretase. Precisely where during its complex intracellular trafficking APP can undergo the α-, β- and γ-secretase remains unknown.

A number of functions have been ascribed to APP holoproteins and/or their major secreted derivative (α-$APP_s$) based on cell culture studies. Soluble α-APPs appear to be capable of acting as an autocrine factor and as a neuroprotective and perhaps neuritotropic factor. In vitro studies indicate that the 751- and 770-residue isoforms (encoding a KPI motif) inhibit serine proteases such as trypsin and chymotrypsin. The secreted APP isoforms can confer cell-cell and cell-substrate adhesive properties in culture. All of these imputed functions have not yet been confirmed in vivo.

In polarized epithelial cells, such as Madin-Darby canine kidney (MDCK) cells, APP is targeted principally to the basolateral membrane, where it can undergo α-secretase cleavage to release α-$APP_s$ basolaterally, although a small fraction is targeted and processed apically. In neurons, which are one of the cell types that express the highest levels of APP in the body (particularly APP695), APP can be transported anterogradely in the fast component of axonal transport. APP is present in vesicles in axonal terminals, although not specifically in synaptic vesicles. Cell biological studies demonstrate that APP in the axonal terminals can be transported retrogradely up the axon to the cell body, and some molecules then are fully translocated to the somatodendritic surface. During its retrograde axonal trafficking, some APP molecules can be recycled to the axolemmal surface.

Although it has been assumed that APP axonal terminals might be a principal site for the generation of Aβ, this has not been definitely determined, and APP that recycles in endosomes at various neuronal subsites may be capable of undergoing the sequential β- and γ-secretase cleavages to release the peptide. Although APP is particularly abundantly expressed in neurons and neurons have been shown to secrete substantial amounts of Aβ peptides, other brain cells, which also express APP and release variable amounts of Aβ, including astrocytes, microglia, and endothelial and smooth muscle cells, could contribute to the secreted pool of Aβ that eventually leads to extracellular deposition. Moreover, the fact that (i) virtually all peripheral cells also express APP and generate Aβ and (ii) Aβ is present in plasma raises the possibility that circulating Aβ could cross the blood-brain barrier and contribute to cerebral Aβ accumulation.

Lipid Rafts

It generally is believed that brain lipids are intricately involved in Aβ-related pathogenic pathways. The Aβ peptide is the major proteinaceous component of the amyloid plaques found in the brains of AD patients and is regarded by many as the culprit of the disorder. The amount of extracellular Aβ accrued is critical for the pathobiology of AD and depends on the antagonizing rates of its production/secretion and its clearance. Studies have shown that neurons depend on the interaction between Presenilin 1 ("PS1") and Cytoplasmic-Linker Protein 170 ("CLIP-170") to both generate Aβ and to take it up through the lipoprotein receptor related protein ("LRP") pathway. Further to this requirement, formation of Aβ depends on the assembly of key proteins in lipid rafts ("LRs"). The term "lipid rafts" as used herein refers to membrane microdomains enriched in cholesterol, glycosphingolipids and glucosylphosphatidyl-inositol-(GPI)-tagged proteins implicated in signal transduction, protein trafficking and proteolysis. Within the LRs it is believed that APP is cleaved first by the β-secretase (BACE) to generate the C-terminal intermediate fragment of APP(CFT(C99)), which remains embedded in the membrane. CFT(C99) subsequently is cleaved at a site residing within the lipid bilayer by γ-secretase, a high molecular weight multi-protein complex containing presenilin, (PS1/PS2), nicastrin, PEN-2, and APH-1 or fragments thereof. Aβ finally is released outside the cell where it may: i) start accumulating following oligomerization and exerting toxicity to neurons, or ii) be removed either by mechanisms of endocytosis (involving apolipoprotein-E (apoE) and LRP or Scavenger Receptors) or by degradation by extracellular proteases including insulin-degrading enzyme (IDE) and neprilysin.

Leptin, similarly to methyl-beta-cyclodextrin, reduces beta-secretase activity in neuronal cells. In addition, leptin increases apoE-dependent Aβ uptake in vitro. Like leptin, methyl-beta-cyclodextrin reduces beta-secretase activity in neuronal cells, possibly, but without being limited by theory, by altering the lipid composition of membrane LRs. Like leptin, inhibitors of acetyl CoA carboxylase (e.g. TOFA) and fatty acid synthase (cerulenin) mimic leptin's action, i.e., act as leptin mimics. In contrast, etoxomir, an inhibitor of carnitine palmitoyl transferase-1, is known to increase Aβ production.

Alzheimer's Disease

Alzheimer's disease (also called "AD", "senile dementia of the Alzheimer Type (SDAT)" or "Alzheimer's") is a progressive neurodegenerative disorder of the central nervous system ("CNS"). AD is usually diagnosed clinically from the patient history, collateral history from relatives, and clinical observations, based on the presence of characteristic neurological and neuropsychological features.

The pathology of AD includes, but is not limited to, (1) missense mutations in APP, PS1 and PS2 genes; (2) altered proteolysis of Aβ42; (3) progressive accumulation and aggregation of Aβ42 in brain interstitial fluid; (4) deposition of aggregated Aβ42 as diffuse plaques (in association with proteoglycans and other amyloid-promoting substrates); (5) aggregation of Aβ40 onto diffuse Aβ42 plaques and accrual of certain plaque-associated proteins (such as, for example, complement clq, etc.); (6) inflammatory response including (a) microglial activation and cytokine release, (b) astrocytosis and acute phase protein release; (7) progressive neuritic injury within amlyoid plaques and elsewhere in the neuropil; (8) disruption of neuronal metabolic and ionic homeostasis; oxidative injury; (9) altered kinase/phosphatase activities leading to hyperphosphorlyated tau which leads to PHF formation; (10) widespread neuronal/neuritic dysfunction and death in hippocampus and cerebral cortex with progressive neurotransmitter deficits; and (11) dementia. The ultimate effects that may further present in the affected cortical regions include neuritic dystrophy, synaptic loss, shrinkage of neuronal perikarya, and selective neuronal loss.

AD is further characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyms. Both amyloid plaques ("AP") and neurofibrillary tangles ("NFT") are clearly visible after silver staining by microscopy in brains of those afflicted with AD.

Plaques

Amyloid plaques are dense, mostly insoluble deposits of amyloid-beta ("Aβ") protein and cellular material outside and around neurons. Dystrophic neurites that contain amyloid precursor protein ("APP") are seen in traumatic brain injury, and "diffuse plaques" can be observed in association with dementia pugilistica, but the appearance of amyloid plaques in AD is unique. The particular appearance of neuritic plaques (i.e., Aβ peptide-containing extracellular lesions surrounded by tau neurofibrillary pathology) is considered specific for AD. It generally is believed that amyloid plaques are not a nonspecific reaction to neurofibrillary pathology because non-AD tauopathies lack amyloid plaques. Further attesting to the specificity of AD-type amyloid plaques is the fact that mutations or duplications of the APP gene as in Down's syndrome produce the specific features of AD, clinically and pathologically. Accordingly, AD involves a specific combination of neuritic amyloid plaques and NFTs where the neuritic plaques seem more specific to the disease, and the NFTs seem more likely to induce neurodegeneration.

Neuritic Plaques

Neuritic plaques comprise roughly spherical extracellular amyloid deposits that are invested by degenerating or dying back nerve cell processes. These abnormal dendrites and axons contain aberrant tau fibrils identical to those seen in NFTs. In a given neuritic plaque, axons from a variety of different sources expressing distinct neurotransmitter signatures may be present. These neurites often are dilated and tortuous and are marked by ultrastructural abnormalities that include enlarged lysosomes, numerous mitochondria, and paired helical filaments, the latter indistinguishable from those that comprise the neurofibrillary tangles. Such plaques also are intimately associated with microglia expressing surface antigens associated with activation, such as CD45 and HLA-DR; they are surrounded by reactive astrocytes displaying abundant glial filaments. The microglia usually are within and adjacent to the central amyloid core of the neuritic plaque, whereas the astrocytes often ring the outside of the plaque, with some of their processes extending centripetally toward the amyloid core. The time that it takes to develop such a neuritic plaque is unknown, but these lesions probably evolve very gradually over substantial period of time, perhaps many months or years. The surrounding neuritis that contributes to any one plaque can emanate from local neurons of diverse neurotransmitter classes. Much of the fibrillar Aβ found in the neuritic plaques is the species ending at amino acid 42 (Aβ42), the slightly longer, more hydrophobic form that is particularly prone to aggregation. However, the Aβ species ending in amino acid 40 (Aβ40), which normally is more abundantly produced by cells than is Aβ42, usually is colocalized with Aβ42 in the plaque. The cross-sectional diameter of neuritic plaques in microscopic brain sections varies widely from 10 μm to greater than 120 μm, and the density and degree of compaction of the amyloid fibrils that comprise the extracellular core also shows great variation among plaques.

Neuritic plaques represent a nidus in which the extracellular amyloid plaque pathology induces intracellular neurofibrillary pathology and apparent structural and functional disruption.

Diffuse Plaques (Preamyloid Deposits)

Many Aβ deposits lack the compacted, fibrillar appearance of the classical neuritic plaques. Studies have indicated that many of the plaques found in limbic and association cortices, and virtually all of those found in brain regions not clearly implicated in the typical symptomatology of AD (for example, thalamus, caudate, putamen, cerebellum), show relatively light, amorphous Aβ immunoreactivity to diagnostic antibodies developed to endogenous Aβ or synthetic Aβ that occurs in a finely granular pattern, without a clearly fibrillar, compacted center. The detection of these plaques in regions that also contain many neuritic plaques led to the hypothesis that these plaques represent precursor lesions of neuritic plaques, and thus are referred to as "diffuse plaques" or "preamyloid deposits." The Aβ peptides deposited in AD brain principally ends at either Aβ40 or Aβ42. Studies have indicated that peptides that end at Aβ42 are subunits of the material comprising the diffuse plaques, with little or no Aβ40 immunoreactivity, in contrast to the mixed (Aβ42 plus Aβ40) deposits that generally are found in the fibril-rich neuritic plaques.

Neurofibrillary Tangles

Many neurons in the brain regions typically affected in AD (entorrhinal cortex, hippocampus, parahippocampus gyms, amygdale, frontal, temporal, parietal and occipital association cortices, and certain subcortical nuclei projecting to these regions) contain large, nonmembrane-bound bundles of abnormal fibers that occupy much of the perinuclear cytoplasm. Most of these fibers consist of pairs of 10 nm filaments wound into helices (paired helical filaments (PHF)), with a helical period of about 160 nm. Some tangle-bearing neurons also contain skeins of straight, 10 nm to 15 nm filaments interspersed with the PHF. Neurofibrillary tangles (NFTs) are aggregates of the microtubule-associated protein "tau", which have become hyperphosphorylated and accumulate inside the cells themselves. Tau is relatively abundant in neurons but is present in all nucleated cells and functions physiologically to bind microtubules and to stabilize microtubule assembly for polymerization. The tau gene, comprised of over 100 kilobases and containing 16 exons, contains consensus binding sites for transcription factors such as AP2 and SP1. In the adult brain, alternative splicing of tau nuclear RNA transcribed on exons 2, 3 and 10, results in six tau isoforms, each (i) having either 3 or 4 peptide repeats of 31 or 32 residues in the C terminal region encoded on exon 10, (ii) comprising the microtubule binding domain or (iii) differing in the expression of 0, 1 or 2 inserts encoded on exons 2 and 3. These tau isoforms, as well as their phosphorylation status, change during development such that 3 repeat ("3R") tau with no inserts is expressed in the fetus and early postnatal infant, while heterogeneous isoforms are expressed in the adult brain. This switch in RNA splicing also corresponds to a reduction in tau phosphorylation.

During neurodegeneration, tau is phosphorylated abnormally at proline directed serine/threonine phosphorylation sites, which can be detected using specific antisera. These serine/threonine (Ser/Thr) phoshorylation sites include Ser-202/Thr-205 (AT8 site), Ser-214 and/or Ser-214, Ser-181, and/or Ser-212 (AT100 site), Thr-231 and/or Ser-235 (TG3 site), and Ser-396/Ser-404 (PHF-1 site). The profile of alternative tau splicing differs among pathological phenotypes, such that tau accumulation in AD is a mixture of 3R and 4R tau, Pick disease tends to be 3R tau, corticobasal degeneration and progressive supranuclear palsy tends to be 4R tau, and so-called agryrophilic grain disease accumulates small inclusions comprised of 3R tau. The general term "tauopathy" encompasses the broad classification of neurodegenerative diseases that accumulate phosphorylated tau.

A variety of kinases have been shown to be capable of phosphorylating tau in vitro at various sites. Nevertheless, it has not become clear whether one or more kinases are principally responsible for initiating the hyperphosphorylation of tau in vivo that leads to its apparent dissociation from microtubules and aggregation into insoluble paired helical filaments.

The correlation between regional distribution of phosphorylated tau and clinical signs suggests a close relationship between tau and AD pathogenesis. The increased tau phosphorylation that accompanies AD may result in separation of tau from the microtubule, possibly aided by other factors (such as, for example, Aβ, oxidative stress, inflammatory mediators), and sequestration of NFTs and neuropil threads. Without being limited by theory, the loss of normal tau function (stabilization and maintenance of microtubules), combined with a toxic gain of function, could compromise axonal transport and contribute to synaptic degeneration. The role of NFT toxicity, however, remains unclear. Studies have indicated that mice models expressing a repressible human tau still developed NFTs, neuronal loss, and behavioral impairments; after tau suppression, the behavioral deficits stabilized, yet NFTs continued to accumulate. In another AD-like model, axonal pathology with accumulation of tau proceeded plaque deposition. NFTs (and presumable "intermediates") exist within the cytoplasm of viable neurons. Only in advanced disease are large numbers of extracellular NFTs identified.

NFTs are not specific for AD, particularly if a broader definition of NFTs includes different tau isoforms or if one expands the expectation of the morphological characteristics of NFTs. The two classical lesions of AD, neuritic plaques and NFTs, can occur independently of each other. Tangles composed of tau aggregates that are biochemically similar to, or in some cases, indistinguishable from those in AD have been described in more than a dozen less common neurodegenerative diseases, in almost all of which one finds no Aβ deposits and neuritic plaques.

NFTs appear in multiple brain diseases, and may contribute to neurodegeneration in more than one disease state. In addition to AD, NFTs also are found in some frontotemporal dementias, myotonic dystrophy, viral panencephalitis, dementia pugilistica, some prion diseases, and other brain diseases. For many of these disorders, the severity of NFT pathology is less than that observed in end-stage AD. Further, no condition characterized by widespread neocortical NFTs lacks extensive neurodegeneration and clinical dementia. On the other hand, there are many subtypes of chronic brain diseases in which there are extensive neurodegeneration and clinical dementia without NFTs, such as many subtypes of frontotemporal dementias, synucleinopathies, subacute or chronic infarcts, metabolic, demyelinating, developmental, and trinucleotide repeats diseases. Tau protein itself can directly trigger neurodegeneration: many germ line mutations in tau produce clinical dementia with NFTs. These tauopathies are distinct from AD, but common pathways may be involved. NFTs appear in multiple brain diseases, and may contribute to neurodegeneration in more than one disease state.

Dystrophic Cortical Neurites Within and Outside Neuritic Plaques

Many of the dilated and tortuous neurites found within and immediately surrounding amyloid plaques contain PHF that are structurally, biochemically and immunocytochemically indistinguishable from those that comprise the NFTs. In addition, plaques often contain numerous dystrophic neurites that are not immunoreactive for PHF tau. Tau-positive dystrophic neurites also are present in a more widespread distribution in the cortical neuropil outside of the neuritic plaques. The prevalence and density of dystrophic cortical neurites that contain altered forms of tau varies substantially among AD patients. Studies have shown that AD patients particularly rich in NFTs also are those that show widespread tau-immunoreactive dystrophic cortical neurites. Some of the intraplaque and extraplaque dystrophic neurites are immunoreactive for phosphorylated forms of the neurofilament subunit proteins; thus phosphorylated forms of the neurofilament subunit proteins can coexist with phosphotau reactivity. These observations suggest that there may be several substrates for the altered kinase and phosphatase activities that occur in tangle-bearing neurons and dystrophic neurites.

Amyloid Microangiopathy

Aβ originally was isolated from amyloid-laden meningeal arterioles and venules that often are found just outside of the brains of patients with AD or Down's syndrome. Similarly, small arterioles, venules, and capillaries within cerebral cortex also frequently bear amyloid deposits. This microvascular angiopathy is characterized at the ultrastructural level by amyloid fibrils found in the abluminal basement membrane of the vessels, sometimes with apparent extension of the fibrils into the surrounding perivascular neuropil (dyshorric angiopathy). The Aβ peptides that occur as filaments in the microvessel basement membranes appear, on the basis of immunoreactivity, to be principally Aβ40 species, although evidence has been presented that the initially deposited species in vessels destined to develop amyloid angiopathy may be Aβ42. The extent of amyloid angiopathy varies widely among AD brains that have relatively similar burdens of parenchmyal Aβ. The contribution of this microvascular amyloidosis to the cortical dysfunction that occurs in AD and the mechanism by which amyloid alters microvascular function remains unknown. Amyloid-bearing vessels composed of Aβ deposits essentially indistinguishable from those of AD can occur in the virtual absence of parenchymal Aβ deposits in the brains of elderly subjects without AD. Such amyloid-bearing vessels in this condition (congophilic amyloid angiopathy (CAA)) as well as those in AD can occasionally rupture, leading to one or multiple cerebral hemorrhages. Nevertheless, the large majority of AD patients do not experience cerebral hemorrhages, despite the presence of some or many microvascular amyloid deposits.

The Principal Underlying Cause of Alzheimer's Disease Remains Unknown

The principal underlying cause of AD remains unknown. Disagreements persist as to whether Aβ peptide-rich plaques or NFTs are the principal neuordegenerative element and whether they are etiologically related. There is a high degree of disparity among research efforts to address whether there are earlier biochemical events that ultimately lead to the characteristic pathology. It generally is believed that soluble Aβ oligomers, prior to plaque buildup, exert neurotoxic effects leading to neurodegeneration, synaptic loss and dementia. Further, increased Aβ levels may result from abnormal lipid accumulation, thereby producing altered membrane fluidity and lipid raft composition. However, for sporadic AD, representing the overwhelming majority of AD cases, there still is no convincing evidence for a particular cause that triggers the Aβ cascade.

Leptin

Leptin is a helical protein, secreted by adipose tissue, which acts on a receptor site in the ventromedial nucleus of the hypothalamus to curb appetite and increase energy expenditure as body fat stores increase. Leptin levels are 40% higher in women, and show a further 50% rise just before menarche, later returning to baseline levels. Leptin levels are lowered by fasting and increased by inflammation.

Ablation of leptin or of leptin signaling is sufficient to cause obesity as exemplified by leptin-deficient obese, hyperinsulinemic mice having the genotype ob/ob; diabetic mice with a mutation in the leptin receptor gene having the genotype db/db, which produce but are non-responsive to leptin; rats of the genotype fa/fa, which have the "fatty" obesity gene, which is a mutated leptin receptor; and in a few rare genetic cases (Schwartz et al., Nature. 404: 661-71 (2000)). Laboratory mice having mutations on the ob gene, which encodes leptin, become morbidly obese, diabetic, and infertile; administration of leptin to these mice improves glucose tolerance, increases physical activity, reduces body weight by 30%, and restores fertility. Mice with mutations of the db gene, which encodes the leptin receptor, also become obese and diabetic but do not improve with administration of leptin. Human genes encoding both leptin and the leptin receptor site have been identified. Although mutations in both the leptin and leptin receptor genes have been found in a small number of morbidly obese human subjects with abnormal eating behavior, the majority of obese persons do not show such mutations, and have normal or elevated circulating levels of leptin. An immune deficiency seen in starvation may result from diminished leptin secretion. Mice lacking the gene for leptin or its receptor show impairment of T-cell function, and, in laboratory studies, leptin has induced a proliferative response in human CD4 lymphocytes.

Leptin binding to its functional receptor recruits Janus tyrosine kinases and activates the receptor, which then serves as a docking site for cytoplasmic adaptors such as STAT (Baumann, H., et al. Proc. Natl. Acad. Sci. USA 93:8374 1996)). According to the general model for JAK/STAT activation, STAT proteins initially are present in inactive forms in the cytoplasm. Following ligand stimulation and receptor dimerization, the JAK/STAT pathway is activated by activation of receptor-bound JAK kinases. These JAK kinases subsequently phosphorylate the receptor at tyrosine residues, which recruits STATs to the receptor. STATs then are phosphorylated to form phosphoSTATs, dimerized, and translocated to the nucleus, where the phosphoSTAT dimers bind to specific sequences in the promoter regions of their target genes, and stimulate the transcription of these genes (Schindler et al., Ann. Rev. Biochem. 64: 621-51 (1995)), including negative regulators, such as the suppressor of cytokine signaling 3 (Bjorbaek, C., K. et al. J. Biol. Chem. 274:30059 (1999)) and the protein tyrosine phosphatase 1B (Cheng, A. N. et al. Dev. Cell 2:497 (2002), Schwartz et al., Nature, 404:661-71 (2000), Louis A. Tartaglia, J. Biol. Chem. Minireview, 272:6093-6096 (March 1997)).

In addition to the JAK-2-STAT-3 pathway, other pathways also are involved in mediating leptin's effect in the brain and on the immune cells. For example, the mitogen-activated protein kinase (MAPK) pathways, the insulin receptor substrate 1 (IRS1) pathway, and the phosphatidylinositol 3'-kinase (PI3'K) pathway (Martin-Romero, C., V. Sanchez-Margalet. Cell. Immunol. 212:83 (2001)) also mediate leptin's action (Sanchez-Margalet, V., C. Martin-Romero, Cell. Immunol. 211:30 (2001)).

Leptin also may have a physiologic role as a liporegulatory hormone responsible for maintaining intracellular homeostasis in the face of wide variations in caloric intake (Unger R H.2003. Annu Rev Physiol. 65:333-47). This is achieved by directly stimulating lipolysis, (meaning fat breakdown), and inhibiting lipogenesis (meaning fat synthesis) (Lee Y, et al., J. Biol. Chem. 276(8):5629-35 (2001)). Leptin also can improve insulin resistance and hyperglycemia by a mechanism not completely understood (Toyoshima et al., Endocrinology 146: 4024-35 (2005)), despite insulin's ability to stimulate lipogenesis (Kersten, EMBO Reports 2(4): 282-286 (2001). This aspect of leptin's physiological role is important, because insulin and Aβ share a mechanism for their clearance, namely degradation by insulin degrading enzyme (IDE).

Leptin also controls insulin sensitivity. Within the central nervous system (CNS), leptin crosses the blood brain barrier to bind specific receptors in the brain to mediate food intake, body weight and energy expenditure. In general, (i) leptin circulates at levels proportional to body fat; (ii) leptin enters the CNS in proportion to its plasma concentration; (iii) leptin receptors are found in brain neurons involved in regulating energy intake and expenditure; and (iv) leptin controls food intake and energy expenditure by acting on receptors in the mediobasal hypothalmus.

It generally is believed that leptin inhibits the activity of neurons that contain neuropeptide Y (NPY) and agouti-related peptide (AgRP), and increases the activity of neurons expressing α-melanocyte-stimulating hormone (α-MSH). The NPY neurons are a key element in the regulation of appetite; small doses of NPY injected into the brains of experimental animals stimulates feeding, while selective destruction of the NPY neurons in mice causes them to become anorexic. Conversely, α-MSH is an important mediator of satiety, and differences in the gene for the receptor at which α-MSH acts in the brain are linked to obesity in humans.

AMP-Activated Protein Kinase (AMPK)

AMP-activated protein kinase (AMPK) is a phylogenetically conserved serine/threonine protein kinase that exists as a heterotrimeric complex consisting of a catalytic subunit α and two regulatory β and γ subunits. The conventional serine/threonine activity of AMPK is supported by its α subunit, which is characterized by the presence (in the activation loop) of a threonine residue (Thr172) whose phosphorylation is required for activation. The C-terminal region of α subunit is required for association with the other two β and γ subunits. The β subunit contains a C-terminal region required for the association with α and γ subunits and a central region that allowed AMPK complex to bind glycogen. The γ subunit contains four tandem repeats known as cystathionine β-synthase ("CBS") motifs which bind, together, two molecules of AMP or ATP in a mutally exclusive manner. Binding of AMP (on γ subunit) activates AMPK via a complex mechanism involving direct allosteric activation and phosphorylation of α subunit on Thr172 by upstream kinases such as the protein kinase LKB1 (a tumor suppressor whose germline mutations in humans are the cause of Peutz-Jeghers syndrome), the CaMKKIIβ (calmodulin-dependent protein kinase kinase IIβ) and potentially TAK1 (mammalian transforming growth factor β-activated kinase).

Homologues of all three subunits have been identified in mammals, fruitfly (Drosophila melanogaster), worm (Caenorhabditis elegans), yeast (Saccharomyces cerevisiae), plants (Arabidopsis thaliana) and the primitive protozoan Giardia lamblia, with a high degree of conservation that suggests that this protein evolved at least a billion years ago to regulate a wide spectrum of actions on metabolic homeostasis. In mammals, two to three isoforms of each subunit (α1, β2, β1, β2, γ1, γ2, γ3) encoded by different genes are known giving rise to a large variety of heterotrimeric combinations, with splice variants (for the γ2 and γ3 genes) adding to the diversity. Furthermore, differences in the tissue distribution of the expression patterns of catalytic and regulatory isoforms have been reported.

Studies of isoform composition of AMPK complexes in human skeletal muscle found that only 3 of the 12 theoretically possible AMPK complexes were present (α2β2γ1>>α2β2γ3=α1β2γ1) and were activated differently depending on exercise intensity and duration. Moreover, specificity of each catalytic isoform has been shown for its preferentially upstream kinase in both skeletal muscle and heart; indeed, in LKB1−/− mice, ischemia in the heart and contraction in skeletal muscle were not able to activate AMPKα2 subunit, whereas AMPKα1 activation was only slightly affected. Expression of the γ3 subunit appeared highly specific to glycolytic skeletal muscle whereas γ1 and γ2 showed broad tissue distributions. In skeletal muscle, the β2 subunits also is highly expressed but the β1 subunit predominates in the liver. AMPKα1 and α2-containing complexes account each for about half of total AMPK activity in liver. In adipose tissue, AMPK complexes containing the al catalytic subunit are mainly expressed whereas, in skeletal and cardiac muscles, AMPK complexes containing the α2 catalytic subunit are predominant.

In addition to differences in tissue distribution, it generally is believed that distribution of AMPK complexes also is regulated at the intracellular level. AMPKα2-containing complexes have been found in both the nucleus and the cytoplasm; this raises the possibility of the direct phosphorylation of co-activators and transcription factors. In contrast, AMPKα1-containing complexes are predominantly localized in the cytoplasm but also have been observed at the plasma membrane in airway epithelial cells and cartoid body cells. Although the functional significance of different AMPK isoform combination, as well as the function of each heterotrimeric AMPK complex in relation with its particular sensitivity to AMP and ATP, subcellular localization and/or specific targets remains unclear; it has been hypothesized that regulation of exercise-induced glucose transport in human skeletal muscle could be associated with α2β1 rather than α2β2γ3 heterotrimeric complex activation. It has been further suggested that isoform combination also may determine subcellular targeting of AMPK and hence targeting substrates. Studies have shown that the post-translational modification of the β1 subunit may target AMPK complexes to the plasma membrane. In addition, it was found that plectin, a cytoskeleton linker protein which has been shown to bind the γ1 subunit, affects the subunit composition of AMPK complexes in differentiated myotubes. Thus, the selective expression of a particular AMPK complex could determine a specialized cellular and systemic response to different metabolic stresses.

There have been very few studies of the metabolic pathways triggered by leptin in AD pathobiology, and the role of 5-adenosine monophosphate protein kinase (AMPK) in AD pathobiology remains unclear.

The described invention, which provides methods related to treating progressive cognitive dysfunction resulting from accumulations of NFTs or Aβ, also provides methods and compositions for treating AD utilizing leptin and its role in the regulation of two major AD pathways via distinct AMPK-dependent mechanisms in neuronal cells. This bimodal action of leptin, and potentially of AMPK activators, provides a novel therapeutic approach to AD treatment. Currently approved therapies fail to target any of the AMPK-related facets of the disease and provide only symptomatic relief. Further, current investigational drugs address, at most, only one AMPK-related aspect.

SUMMARY OF THE INVENTION

The present disclosure provides compositions and methods of clinical therapy and diagnostic methods for progressive cognitive disorders.

According to one aspect, the described invention provides a method for treating a progressive cognitive disorder, the method comprising the steps: (a) providing a therapeutically effective amount of a leptin composition, wherein the leptin composition comprises (i) a leptin or a leptin analog as a first therapeutic agent; (ii) optionally, at least one a second therapeutic agent; and (iii) a pharmaceutically acceptable carrier; (b) administering to a subject in need thereof the composition of (a); and (c) reducing or preventing progression of at least one pathology of the progressive cognitive disorder. According to one embodiment, the composition decreases production of Aβ, increases uptake of Aβ, or decreases phosphorylation of tau protein. According to another embodiment, a site of phosphorylation of the tau protein comprises at least one of Ser-202/Thr-205 (AT8 site), Ser-214, Ser-181, Ser-212 (AT100 site), Thr-231, Ser-235 (TG3 site), and Ser-396/Ser-404 (PHF-1 site). According to another embodiment, the progressive cognitive disorder is Alzheimer's Disease, progressive supranuclear palsy; a dementia; Creutzfeldt-Jacob disease, frontotemporal dementia, Pick's disease, Frontotemporal Dementia with Parkinsonism-17 corticobasal degeneration, frontotemporal lobe degeneration; Huntington's Disease; or Parkinson's Disease. According to another embodiment, the progressive cognitive disorder is Alzheimer's disease. According to another embodiment, the pathology comprises at least one selected from the group of phosphorylation of a tau protein; neurofibrillary tangles; an altered proteolysis of APP; an accumulation of Aβ42 in brain interstitial fluid; an aggregation of Aβ42 in brain interstitial fluid; an accumulation of Aβ40 in brain interstitial fluid; an aggregation of Aβ40; an inflammatory response; a neuritic injury; a disruption of neuronal metabolic homeostasis; a disruption of neuronal ionic homeostasis; an oxidative injury; an altered kinase activity; an altered phosphatase activity; .neuronal dysfunction; neuronal cell death; a neurotransmitter deficit; a dementia; a neuritic dystrophy; shrinkage of neuronyl perikarya, and synaptic loss. According to another embodiment, the optional at least one second therapeutic agent is selected from the group consisting of an antibiotic agent, an anti-fungal agent, a kinase inhibitor an anti-viral agent, an anti-protozoal agent, a steroidal anti-inflammatory agent, an anti-oxidant, a hormone, a vitamin, an antihistamine, and a chemotherapeutic agent. According to another embodiment, the optional second therapeutic agent is at least one kinase inhibitor. According to another embodiment, the at least one kinase inhibitor is selected from the group consisting of a kinase inhibitor of calcium/calmodulin-dependent protein kinase II; a kinase inhibitor of protein kinase A; a kinase inhibitor of GSK-3β; a kinase inhibitor of cAMP-dependent protein kinase; a kinase inhibitor of 5-adenosine monophosphate protein kinase; Myr-AIP, LiC1 KT5720, 6-bromoindirubin-3'-oxime ((2'Z,3'E)-6-bromoindirubin-3'-oxime); KT5720; K252a; staurosporine; KT5252b; chelerythrine; and TDZD-8 (4-Benzyl-2-methyl-1,2,4-thiadiazolidine-3,5-dione-8). According to another embodiment, the composition provides kinase inhibition at levels greater than the sum of composition components (i), (ii), and (iii). According to another embodiment, the therapeutically effective amount of the leptin or leptin analog in the leptin composition is an amount from about 0.0001 mg/kg body weight to about 100 g/kg body weight. According to another embodiment, the composition improves at least one cognitive function. According to another embodiment, the at least one cognitive function is memory. According to another embodiment, the at least one cognitive function is learning.

According to another aspect, the described invention provides a method for improving resilience of cognitive function in a subject in need thereof, the method comprising the steps: (a) administering to the subject in need thereof a leptin composition comprising: (i) a cognitive function enhancing amount of a leptin or a leptin analog as a first therapeutic agent; (ii) optionally, at least one second therapeutic agent, and (ii) a pharmaceutically acceptable carrier; wherein the composition decreases Aβ production, increases uptake of Aβ, or decreases a level of phosphorylated tau; and (b) improving resilience of a cognitive function in the subject. According to one embodiment, a serine/threonine phoshorylation site of the phosphorylated tau comprises at least one of Ser-202/Thr-205 (AT8 site), Ser-214, Ser-181, Ser-212 (AT100 site), Thr-231, Ser-235 (TG3 site), and Ser-396/Ser-404 (PHF-1 site). According to another embodiment, the cognitive function is memory. According to another embodiment, the memory is a conditioned memory. According to another embodiment, the memory is a contextual memory. According to another embodiment, the cognitive function is memory retention. According to another embodiment, the cognitive function is learning. According to another embodiment, the learning is a contextual learning. According to another embodiment, the learning is a conditioned learning. According to another embodiment, the optional second therapeutic agent is selected from the group consisting of an antibiotic agent, an anti-fungal agent, a kinase inhibitor an anti-viral agent, an anti-protozoal agent, a steroidal anti-inflammatory agent, an anti-oxidant, a hormone, a vitamin, an antihistamine, and a chemotherapeutic agent. According to another embodiment, the optional second therapeutic agent is at least one kinase inhibitor. According to another embodiment, the at least one kinase inhibitor is selected from the group consisting of a kinase inhibitor of calcium/calmodulin-dependent protein kinase II; a kinase inhibitor of protein kinase A; a kinase inhibitor of GSK-3β; a kinase inhibitor of cAMP-dependent protein kinase; a kinase inhibitor of 5-adenosine monophosphate protein kinase; Myr-AIP, LiC1 KT5720, 6-bromoindirubin-3'-oxime ((2'Z,3'E)-6-bromoindirubin-3'-oxime); KT5720; K252a; staurosporine; KT5252b; chelerythrine; and TDZD-8 (4-Benzyl-2-methyl-1,2,4-thiadiazolidine-3,5-dione-8). According to another embodiment, the composition provides kinase inhibition at levels greater than the sum of composition components (i), (ii), and (iii). According to another embodiment, the cognitive function-enhancing amount of the leptin or leptin analog in the leptin composition is an amount from about 0.0001 mg/kg body weight to about 100 g/kg body weight.

According to another aspect, the described invention provides a method for identifying an effective therapeutic agent for treating a progressive cognitive dysfunction disease or disorder that results from at least one of an accumulation of Aβ, a phosphorylation of tau protein, or an accumulation of neurofibrillary tangles, the method comprising the steps: (a) providing a cell culture comprising neuronal cells, (b) contacting the cell culture comprising neuronal cells with a putative therapeutic agent, (c) determining whether the putative therapeutic agent associates with an active portion of a protein kinase protein such that it affects activity of the protein kinase; and (d) identifying the putative therapeutic agent as an effective therapeutic agent for treating the progressive cognitive dysfunction disease or disorder. According to one embodiment, the protein kinase is 5-adenosine monophosphate protein kinase or GSK-3β. According to another embodiment, the putative therapeutic agent or effective therapeutic agent is a recombinant protein. According to another embodiment, the putative therapeutic agent or effective therapeutic agent is an inhibitor. According to another embodiment, the putative therapeutic agent or effective therapeutic agent is an antagonist. According to another embodiment, the putative therapeutic agent or effective therapeutic agent is an agonist. According to another embodiment, the putative therapeutic agent or effective therapeutic agent is an antibody. According to another embodiment, the putative therapeutic agent or effective therapeutic agent prevents a leptin or a leptin analog from associating with the protein kinase. According to another embodiment, determining step (c) comprises measuring secretion of amyloid-beta by the neuronal cells, relative to controls. According to another embodiment, the measuring secretion of amyloid-beta by the neuronal cells, relative to controls is by ELISA or immunoblot. According to another embodiment, the method further comprises the step of using the effective therapeutic agent for treating an amyloid beta pathology. According to another embodiment, the amyloid beta pathology comprises at least one selected from the group of phosphorylation of a tau protein; neurofibrillary tangles; an altered proteolysis of APP; an accumulation of Aβ42 in brain interstitial fluid; an aggregation of Aβ42 in brain interstitial fluid; an accumulation of Aβ42 in brain interstitial fluid; an aggregation of Aβ40; an inflammatory response; a neuritic injury; a disruption of neuronal metabolic homeostasis; a disruption of neuronal ionic homeostasis; an oxidative injury; an altered kinase activity; an altered phosphatase activity; .neuronal dysfunction; neuronal cell death; a neurotransmitter deficit; a dementia; a neuritic dystrophy; shrinkage of neuronyl perikarya, and synaptic loss. According to another embodiment, the effective therapeutic agent improves at least one cognitive function. According to another embodiment, the at least one cognitive function is memory. According to another embodiment, the at least one cognitive function is learning.

DETAILED DESCRIPTION

Glossary

Figure 1:
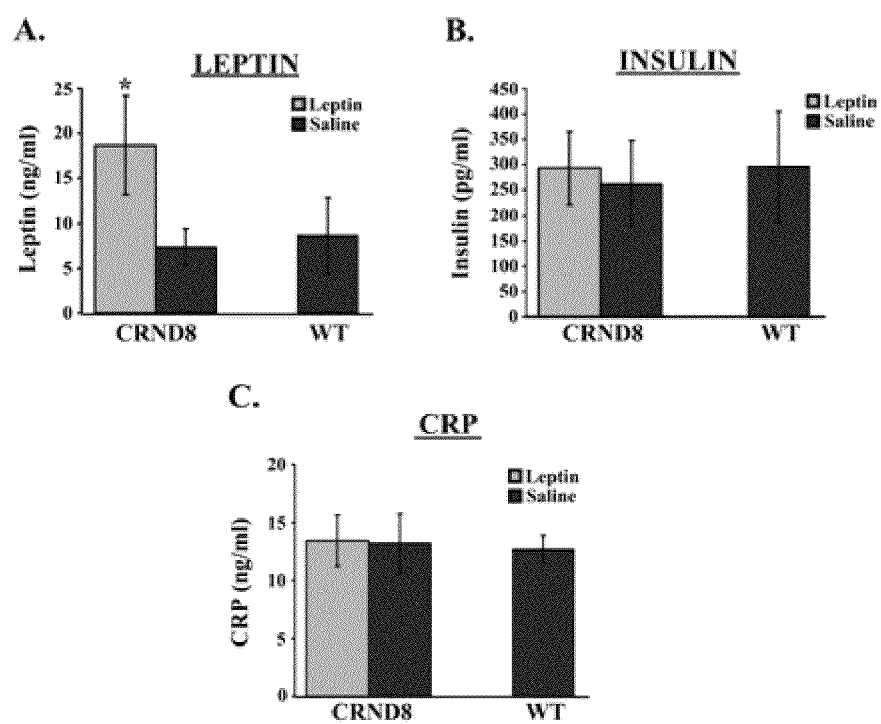
FIG. 1 shows serum concentrations of leptin, insulin and CRP in CRND8 and wt mice. Circulating levels of (A) leptin, (B) insulin and (C) CRP were assessed in serum from leptin- or saline-treated CRND8 or wild type ("wt") mice by ELISA. Results (n=6) are presented as the mean concentration (ng/ml or pg/ml)±SD. * vs. saline-treated CRND8.

The term "active portion" as used herein refers to the region of a peptide or protein that enables the function of the peptide or protein.

The term "administering" as used herein refers to causing to take or apportioning and includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The term "affect" in its various grammatical forms as used herein refers to having or producing an impact, material influence, or alteration.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "allosteric" relates to a change in conformation upon binding of an effector. The term "allosteric regulation" refers to the regulation of an enzyme or other protein by binding an effector molecule at the enzyme's or protein's allosteric site. The regulatory site of an allosteric protein generally is physically distinct from its active site. Effectors that enhance the protein's activity are referred to as "allosteric activators", whereas those that decrease the protein's activity are called "allosteric inhibitors." Thus, "allosteric activation" occurs when the binding of one ligand enhances the attraction between substrate molecules and other binding sites; "allosteric inhibition" occurs when the binding of one ligand decrease the affinity for substrate at other active sites.

The term "allosteric modulation" as used herein refers to the process whereby a receptor is regulated, altered, adapted or adjusted (modulated) by the binding of allosteric modulators at a regulatory site, different from the binding site of the endogenous ligand (orthosteric ligand) and enhances or inhibits the effects of the endogenous ligand. An allosteric modulator normally acts by causing a conformational change in a receptor molecule, which results in a change in the binding affinity of the ligand. Thus, an allosteric ligand "modulates" activation of a receptor by a primary "ligand" and can adjust the intensity of the receptor's activation. Many allosteric enzymes are regulated by their substrate; such a substrate is considered a "homotropic allosteric modulator." Non-substrate regulatory molecules are called "heterotropic allosteric modulators."

The term "ameliorate" as used herein means to make better or to become better, or to improve.

The terms "amyloid peptide" "amyloid β peptide" and "Aβ" are used interchangeably herein to refer to the family of peptides generated through proteolytic processing of amyloid precursor protein (APP).

The term "anatagonist" as used herein refers to a substance that counteracts the effects of another substance.

The phrase "anchorage dependent (attached) cells" as used herein refers to cells which require a substratum to divide and produce a monolayer.

The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin ; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate ; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

Antibodies are serum proteins, the molecules of which possess small areas of their surface that are complementary to small chemical groupings on their targets. These complementary regions (referred to as the antibody combining sites or antigen binding sites), of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins ($IgG_1$, $IgG_2$, $IgG_3$, $IgG_4$) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

An antigenic determinant or epitope is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy ($V_H$) and light ($V_\kappa$ and $V_\lambda$) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgGl, λ antibody molecule in the mouse myeloma.

The term "antigen" and its various grammatical forms refers to any substance that can stimulate the production of antibodies and can combine specifically with them. The terms "antigenic determinant" or "epitope" as used herein refers to an antigenic site on a molecule.

The term "anti-fungal agent" as used herein means any of a group of chemical substances having the capacity to inhibit the growth of or to destroy fungi. Anti-fungal agents include, but are not limited to, Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

"Antihistamine agent" as used herein refers to any of various compounds that counteract histamine in the body and that are used for treating allergic reactions (such as hay fever) and cold symptoms. Non-limiting examples of antihistamines usable in context of the described invention include chlorpheniramine, brompheniramine, dexchlorpheniramine, tripolidine, clemastine, diphenhydramine, promethazine, piperazines, piperidines, astemizole, loratadine and terfenadine.

The term "anti-oxidant agent" as used herein refers to a substance that inhibits oxidation or reactions promoted by oxygen or peroxides. Non-limiting examples of anti-oxidants that are usable in the context of the described invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

The term "anti-protozoal agent" as used herein means any of a group of chemical substances having the capacity to inhibit the growth of or to destroy protozoans used chiefly in the treatment of protozoal diseases. Examples of antiprotozoal agents, without limitation, include pyrimethamine (Daraprim®) sulfadiazine, and Leucovorin.

The term "anti-viral agent" as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscamet, Indinavir, Interferons (e.g., IFN-alpha), Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid.

The term "associate" and its various grammatical forms as used herein refers to joining, connecting, or combining to, either directly, indirectly, actively, inactively, inertly, non-inertly, completely or incompletely.

The term "blocker" as used herein refers to a substance that inhibits the physiological action of another substance.

The term "carry" as used herein refers to maintaining a cell line by subculturing the cell line in tissue culture medium containing nutrients that will maintain the phenotype and genotype of the cell line.

The term "cell culture" as used herein refers to establishment and maintenance of cultures derived from dispersed cells taken from original tissues, primary culture, or from a cell line or cell strain.

The term "cell line" as used herein refers to a population of immortalized cells that have undergone transformation and can be passed indefinitely in culture.

The term "cell strain" as used herein refers to cells that can be passed repeatedly but only for a limited number of passages.

The term "clone" as used herein refers to a cell, cell product, or organism that is genetically identical to the unit or individual from which it was derived. "Clonality" as used herein refers to the state of a cell or a substance being derived from one source or the other. Thus, the terms "polyclonal" refers to derived from many clones; "oligoclonal" refers to derived from a few clones; and "monoclonal" refers to derived from one clone.

The term "primary culture" as used herein refers to cells resulting from the seeding of dissociated tissues. Primary cultures often lose their phenotype and genotypes within several passages. Most primary cell cultures have limited lifespan, with the exception of some derived from tumors.

The term "cell passage" as used herein refers to the splitting (dilution) and subsequent redistribution of a monolayer or cell suspension into culture vessels containing fresh media.

The term "confluency" as used herein refers to a measure of the proliferation of cells in a culture medium. Generally, the confluency of a culture in a T flask or in a plate or dish is based on the amount of space between the cells. For example, 100% confluency means the culture plate or dish is completely covered by the cells and there is no more room left for cells to grow; 50% confluency means approximately half of the culture dish or plate is covered by the cells and room remains to grow.

The term "chemotherapeutic agent" refers to chemicals useful in the treatment or control of a disease. Non-limiting examples of chemotherapeutic agents usable in context of the described invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

The term "cognitive function" refers to the intellectual processes resulting in an understanding, perception, or awareness of one's ideas as well as the ability to perform mental tasks, such as thinking, learning, judging, remembering, computing, controlling motor functions, and the like.

The term "cognitive-function enhancing amount" as used herein refers to a therapeutically effective dosage (i.e., dose and frequency of administration) that adds to, improves, or increases mental performance (e.g., perception, memory, judgment, reasoning) in a subject as compared to a subject that has not been administered a cognitive-function enhancing amount of a composition or material. A cognitive function enhancing amount is from about 0.01 mg/kg body weight to about 100 g/kg body weight. This amount includes prophylatic or preventive amounts of compositions of the described invention.

The phrase "original cognitive function level" as used herein refers to the cognitive function demonstrated by a normal, healthy subject.

The term "condition" as used herein refers to a variety of health states and is meant to include disorders or diseases caused by any underlying mechanism or disorder, injury, and the promotion of healthy tissues and organs.

The term "conditioned" as used herein refers to prepared for a specific action, event or process; acquired by learning or experience.

The term "contact" and its various grammatical forms as used herein refers to a state or condition of touching or of being in immediate or local proximity. Contacting a composition to a target destination, such as, but not limited to, an organ, a tissue, a cell, or a tumor, may occur by any means of administration known to the skilled artisan.

The term "context" and its various grammatical forms as used herein refers to a setting or the circumstances in which an event occurs.

The term "dementia" as used herein refers to a decline or a progressive decline in cognitive function due to damage or disease in the brain beyond what might be expected from normal aging.

The phrase "density-dependent inhibition of growth" as used herein refers to the reduced growth response of cells upon reaching a threshold density by which cells recognize the boundaries of neighbor cells upon confluence and respond in vitro, depending on growth patterns, by forming a monolayer. Usually these cells transit through the cell cycle at reduce rate (grow slower).

The term "differentiation" as used herein refers to the process by which a less specialized cell becomes a more specialized cell type.

The terms "disease" or "disorder" or "dysfunction" as used herein refer to an impairment of health or a condition of abnormal functioning.

The term "drug" as used herein refers to a therapeutic agent or any substance, other than food, used in the prevention, diagnosis, alleviation, treatment, or cure of disease.

The term "effector" as used herein refers to a molecule that binds to a protein and thereby alters the activity of that protein.

The terms "epitope" and "antigenic determinant" are used interchangeably herein to refer to the site on a molecule that an antigen combining site (ACS) recognizes and to which that antibody binds/attaches itself. In some embodiments, an epitope may be an antigenic determinant/antigen binding site on a kinase inhibiting peptide. The epitope may be primary, secondary, or tertiary-sequence related.

The term "fragment" as used herein refers to an isolated portion of a protein, protein complex, peptide, peptide complex, nucleic acid, antibody or other substance.

The term "functional equivalent" as used herein refers to substances, molecules, proteins, peptides or polypeptides having similar or identical effects or use.

The term "half maximal inhibitory concentration" ("IC", "$IC_{50}$", "50% IC") as used herein refers to the amount or concentration that results in a 50% inhibition of a biological or biochemical activity. The $IC_{50}$ is a quantitative measure that indicates how much of a particular drug, agent, or other substance (inhibitor) is needed to inhibit a given biological process, or component of a process such as, for example, an enzyme, a cell, a cell receptor, or a microorganism, by half.

The term "hatch" ("thaw" or "defreeze") as used herein refers to bringing cells out of the freezer, or, to starting a culture from a freezer stock.

The term "hormone" as used herein refers to natural substances produced by organs of the body that travel by blood to trigger activity in other locations or their synthetic analogs. Suitable hormones for use in the context of the described invention include, but are not limited to, any hormone produced by neurosecretory cells, including gonadotropin releasing hormone (GnRH), corticotropin releasing hormone (CRH), thyrotropin releasing hormone (TRH), prolactin inhibiting hormone (dopamine) and orexin (hypocretin), as well as recombinant hormones, meaning hormones produced by a process using DNA engineered to contain sequences that normally would not occur together and introducing that DNA into the cells of a host.

The term "inhibitor" as used herein refers to a molecule that binds to an enzyme thereby decreasing enzyme activity. Enzyme inhibitors are molecules that bind to enzymes thereby decreasing enzyme activity. The binding of an inhibitor may stop a substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury" as used herein refers to damage or harm to a structure or function of the body caused by an outside agent or force, which may be physical or chemical.

The compositions described herein contain isolated molecules. An "isolated molecule" is a molecule that is substantially pure and is free of other substances with which it is ordinarily found in nature or in in vivo systems to an extent practical and appropriate for its intended use. In particular, the compositions are sufficiently pure and are sufficiently free from other biological constituents of host cells so as to be useful in, for example, producing pharmaceutical preparations or sequencing if the composition is a nucleic acid, peptide, or polysaccharide. Because compositions may be admixed with a pharmaceutically-acceptable carrier in a pharmaceutical preparation, the compositions may comprise only a small percentage by weight of the preparation. The composition is nonetheless substantially pure in that it has been substantially separated from the substances with which it may be associated in living systems or during synthesis. As used herein, the term "substantially pure" refers purity of at least 75%, at least 80%, at least 85%, at least 90%, at least 95% or at least 99% pure as determined by an analytical protocol. Such protocols may include, for example, but are not limited to, FACS, HPLC, gel electrophoresis, chromatography, and the like.

The term "isoform" refers to a version of a protein that has the same function as another protein but that has some small difference(s) in its sequence.

The leptin receptor (OB-R), a member of the class I cytokine receptor superfamily, has at least six isoforms as a result of alternative splicing. All isoforms of OB-R share an identical extracellular ligand-binding domain. Leptin's functional receptor (OB-Rb), the b isoform, is expressed not only in the hypothalamus, where it regulates energy homeostasis and neuroendocrine function, but also in other brain regions and in the periphery, including all cell types of innate and adaptive immunity. The full-length b isoform (OB-Rb) lacks intrinsic tyrosine kinase activity and is involved in several downstream signal transduction pathways.

The term "leptin agonist" refers to a compound capable of activating the leptin receptor and/or downstream effectors and of modulating amyloid peptide levels or tau phosphorylation in a subject. Such effectors may include, for example, but are not limited to, AMP-dependent protein kinase ("AMPK"), sterol regulatory element binding proteins ("SREBP"), and GSK-3β.

The term "modulate" as used herein means to regulate, to alter, to adapt or to adjust to a certain measure or proportion.

The terms "modulator molecule" or "modulator" as used herein refer to a molecule that binds to a regulatory site during allosteric modulation and that allosterically modulates the shape of the protein.

The term "monolayer" as used herein refers to a layer of cells one cell thick, grown in a culture.

The term "neurofibrillary tangles" ("NFT") generally refer to aggregates of the microtubule-associated protein "tau", which have become hyperphosphorylated and accumulate inside the cells themselves.

The phrase "non-steroidal anti-inflammatory agents" refers to a large group of agents that are aspirin-like in their action, including ibuprofen (Advil)®, naproxen sodium (Aleve®), and acetaminophen (Tylenol®). Additional examples of non-steroidal anti-inflammatory agents that are usable in the context of the described invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

The term "normal" refers to a standard, model, median or average of a large group.

The term "normal healthy subject" refers to a subject having no symptoms or other clinical evidence of a cognitive disorder.

The term "peptide" is used herein to refer to two or more amino acids joined by a peptide bond.

The term "polypeptide" is used in its broadest sense to refer to a sequence of subunit amino acids, amino acid analogs, or peptidomimetics. The subunits are linked by peptide bonds, except where noted. The leptin or leptin analog polypeptides of the described invention may be chemically synthesized or recombinantly expressed.

The term "protein" is used herein to refer to a large complex molecule or polypeptide composed of amino acids. The sequence of the amino acids in the protein is determined by the sequence of the bases in the nucleic acid sequence that encodes it.

The terms "peptide", "polypeptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The terms "residue" or "amino acid residue" or "amino acid" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The terms "variants", "mutants", and "derivatives", when used the context of a nucleic acid, are used herein to refer to nucleotide sequences with substantial identity to a reference nucleotide sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "substitution" is used herein to refer to that in which a base or bases are exchanged for another base or bases in the DNA. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The terms "deletion" and "deletion mutation" are used interchangeably herein to refer to that in which a base or bases are lost from the DNA.

The term "addition", when used the context of a nucleic acid sequence, as used herein refers to the insertion of one or more bases, or of one or more amino acids, into a sequence.

The following represent groups of amino acids that are conservative substitutions for one another:
1) Alanine (A), Serine (S), Threonine (T);
2) Aspartic Acid (D), Glutamic Acid (E);
3) Asparagine (N), Glutamic Acid (Q);
4) Arginine (R), Lysine (K); 5) Isoleucine (I), Leucine (L), Methionine (M), Valine (V); and
6) Phenylalanine (F), Tyrosine (Y), Tryptophan (W).

The term "similar" is used interchangeably with the terms analogous, comparable, or resembling, meaning having traits or characteristics in common.

In some embodiments, the leptin or leptin analog of the present invention is chemically synthesized. Such a synthetic polypeptide, prepared using the well known techniques of solid phase, liquid phase, or peptide condensation techniques, or any combination thereof, may include natural and unnatural amino acids. Amino acids used for peptide synthesis may be standard Boc (N-α-amino protected N-α-t-butyloxycarbonyl)amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, J. Org. Chem. 37:3403-3409). Both Fmoc and Boc N-α-amino protected amino acids can be obtained from Sigma, Cambridge Research Biochemical, or other chemical companies familiar to those skilled in the art. In addition, the leptin or leptin analog polypeptide may be synthesized with other N-α-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers.

The term "peptidomimetic" refers to a small protein-like chain designed to mimic or imitate a peptide. A peptidomimetic may comprise non-peptidic structural elements capable of mimicking (meaning imitating) or antagonizing (meaning neutralizing or counteracting) the biological action(s) of a natural parent peptide. The terms "leptin peptidomimetic" "leptin mimic", and "leptin mimetic" are used interchangeably herein to refer to a leptin derivative comprising a functional domain of a leptin protein that produces a biological effect. In chemistry a derivative is a compound that at least theoretically may be formed from a precursor compound. These derivatives may be combined with another molecule to produce or enhance the biological effect. The biological effect may include, for example, but is not limited to, modulating amyloid peptide levels within a subject; modulating tau phosphorylation levels within a subject; decreasing amyloid peptide levels within a subject; decreasing tau phosphorylation levels within a subject, and the like. The term "leptin analog" as used herein refers to a compound or substance of similar structure or function to a wild-type leptin protein. For example, a leptin derivative, a leptin mimic, a leptin agonist, a pharmaceutically acceptable salt thereof, or a functional equivalent thereof that either binds to the leptin receptor; activates the leptin signalling cascade; decreases Aβ production, increases uptake of Aβ, or decreases phosphorylation of tau meets the requirements of a leptin analog.

The term "phosphorylated tau accumulation modulating amount" as used herein refers to a therapeutically effective amount of a leptin composition that modulates the phosphorylation of tau protein. A phosphorylated tau accumulation modulating amount includes prophylactic or preventative amounts of the compositions of the described invention.

The term "plate" as used herein refers to a process of aliquoting cells into or onto a culture medium.

The term "potency" as used herein refers to efficacy, effectiveness, strength or, typically, the dissociation constant, which indicates the concentration needed to inhibit an enzyme.

The term "recombinant protein" as used herein refers to a protein produced by genetic engineering.

The term "reduce" and its various grammatical forms as used herein refers to limiting the occurrence of a disorder in individuals at risk of developing the disorder.

The term "resilience" as used herein refers to an ability to return to an original form, position, or function after or during an illness, condition, disease, syndrome or disorder.

The term "solution" as used herein refers to a homogenous, molecular mixture of two or more substances, which may be solids, liquids, gases or a combination of these.

The term "specificity" as used herein refers to the selective attachment or influence of one substance on another.

The term "split" or "pass" as used herein refers to the subculture or passage of cells.

The term "stable cell line" as used herein refers to a cell(s) in which heterlogous DNA has integrated into the host genome and is maintained throughout many generations.

The term "suspension culture" as used herein refers to cells which do not require attachment to substratum to grow, i.e. anchorage independent. Cell cultures derived from blood typically are grown in suspension. Cells in suspension culture can grow as single cells or clumps. Cells that grow as single cells can be subcultured by diluting the cells. However, for cells that grow as clumps, clumps first must be dissociated prior to subculturing of the culture.

"Steroidal anti-inflammatory agent", as used herein, refers to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

The terms "subject" or "individual" or "patient" are used interchangeably to refer to a member of an animal species of mammalian origin, including humans.

The phrase "a subject having a progressive cognitive disease related to accumulated neurofibrillary tangles" as used herein refers to a subject who presents with diagnostic markers and/or symptoms associated with a progressive cognitive disease related to accumulated neurofibrillary tangles. The phrase "progressive cognitive diseases related to accumulated NFTs" refers to disease(s) that result, or are a consequence of, abnormal aggregation of NFTs. Progressive cognitive diseases related to accumulation of NFTs include, but are not limited to, progressive supranuclear palsy; dementia; dementia pugilistica; AD; Creutzfeldt-Jakob disease; frontotemporal dementia; Pick's disease; other tau-positive pathology including Frontotemporal Dementia with Parkinsonism-17 (FTDP-17) corticobasal degeneration; frontotemporal lobar degeneration (FTLD); and dementia lacking distinctive histology.

The phrase "a subject in need thereof" is a patient having, or at risk of having, a progressive cognitive disease related to accumulated NFTs. A progressive cognitive disease related to accumulated neurofibrillary tangles is usually diagnosed clinically from the patient history, collateral history from relatives, and clinical observations, based on the presence of characteristic neurological and neuropsychological features and the absence of alternative conditions. These criteria require that the presence of cognitive impairment, and a suspected dementia syndrome, be confirmed by neuropsychological testing. Advanced medical imaging with computed tomography (CT) or magnetic resonance imaging (MRI), and with single photon emission computed tomography (SPECT) or positron emission tomography (PET) may be used to help exclude other cerebral pathology or subtypes of dementia. Assessment of intellectual functioning including memory testing can further characterize the state of the disease. A histopathologic confirmation including a microscopic examination of brain tissue may be required for a definitive diagnosis. For AD, eight cognitive domains are most commonly impaired: memory, language, perceptual skills, attention, constructive abilities, orientation, problem solving and functional abilities. These domains are equivalent to the NINCDS-ADRDA Alzheimer's Criteria as listed in the *Diagnostic and Statistical Manual of Mental Disorders* (DSM-IV-TR) published by the American Psychiatric Association (incorporated in its entirety herein by reference).

The term "syndrome" as used herein refers to a pattern of symptoms indicative of some disease or condition.

The term "therapeutic agent" as used herein refers to a drug, molecule, nucleic acid, protein, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The active agent may be a therapeutically effective amount of at least one of a leptin, a leptin mimic, a leptin derivative, a leptin fragment, a leptin analog, or a leptin agonist or a pharmaceutically acceptable salt thereof.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The terms "therapeutically effective amount", an "amount effective", or "pharmaceutically effective amount" of one or more of the active agents are used interchangeably to refer to an amount that is sufficient to provide the intended benefit of treatment. An effective amount of the active agents that can be employed according to the described invention generally ranges from generally about 0.01 mg/kg body weight to about 100 g/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutically effective amount" and "pharmaceutically effective amount" include prophylactic or preventive amounts of the compositions of the described invention. In prophylactic or preventive applications of the described invention, pharmaceutical compositions or medicaments are administered to a patient susceptible to, or otherwise at risk of, a disease, disorder or condition resulting from at least one of accumulation of an amyloid peptide, accumulation of NFTs, or hyperphosphorylation of tau, in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "transient transfection" as used herein refers to the introduction of foreign DNA into a cell to allow the expression of the DNA into the host cell without the DNA becoming incorporated into the genome. Protocols are available for opening transient "holes" in the cell membranes allowing plasmids, or siRNA to enter the cell. Cells capable of being transfected often are referred to as "competent cells".

"Vitamin" as used herein, refers to any of various organic substances essential in minute quantities to the nutrition of most animals act especially as coenzymes and precursors of coenzymes in the regulation of metabolic processes. Non-limiting examples of vitamins usable in context of the described invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

The present disclosure provides compositions and methods of clinical therapy and diagnostic methods for progressive cognitive disorders.

(1). Method for Treating a Progressive Cognitive Disorder

According to one aspect, the described invention provides a method for treating a progressive cognitive disorder, the method comprising the steps:

(a) providing a therapeutically effective amount of a leptin composition, wherein the leptin composition comprises
  (i) a leptin or a leptin analog as a first therapeutic agent;
  (ii) optionally a second therapeutic agent; and
  (ii) a pharmaceutically acceptable carrier;
(b) administering to a subject in need thereof the composition of step (a); and
(c) reducing or preventing progression of at least one pathology of the progressive cognitive disorder.

According to some embodiments, the progressive cognitive disorder is progressive supranuclear palsy; dementia; dementia pugilistica; Creutzfeldt-Jakob disease; frontotemporal dementia; Pick's disease; other tau-positive pathology including FTDP-17 corticobasal degeneration; frontotemporal lobar degeneration (FTLD); or dementia lacking distinctive histology.

According to some such embodiments, the pathology is neurofibrillary tangles.

According to some embodiments, the progressive cognitive disorder is Alzheimer's Disease (AD).

According to some such embodiments, the pathology of AD comprises a missense mutation in APP, presenilin 1 (PS1) or presenilin 2 (PS2) gene.

According to another embodiment, the pathology of AD comprises an altered proteolysis of $A\beta_{42}$.

According to another embodiment, the pathology of AD comprises a progressive accumulation and aggregation of $A\beta_{42}$ in brain interstitial fluid.

According to another embodiment, the pathology of AD comprises deposition of aggregated $A\beta_{42}$ as diffuse plaques. According to some such embodiments, the deposition further comprises proteoglycans and other amyloid-promoting substrates.

According to another embodiment, the pathology of AD comprises an aggregation of $A\beta_{40}$ onto diffuse $A\beta_{42}$ plaques and accrual of certain plaque-associated proteins.

According to another embodiment, the pathology of AD comprises an inflammatory response. Inflammatory reponses include, but are not limited to, microglial activation and cytokine release, and astrocytosis and acute phase protein release.

According to another embodiment, the pathology of AD comprises a progressive neuritic injury within amlyoid plaques and elsewhere in the neuropil.

According to another embodiment, the pathology of AD comprises a disruption of neuronal metabolic and ionic homeostasis. According to another embodiment, the pathology of AD comprises an oxidative injury.

According to another embodiment, the pathology of AD comprises altered kinase/phosphatase activities leading to hyperphosphorylated tau which leads to PHF formation.

According to another embodiment, the pathology of AD comprises a widespread neuronal/neuritic dysfunction and death in hippocampus and cerebral cortex with progressive neurotransmitter deficits.

According to another embodiment, the pathology of AD comprises dementia.

According to another embodiment, the pathology of AD involves the cortical regions. According to some such embodiments, the pathology is neuritic dystrophy. According to some such embodiments, the pathology is synaptic loss. According to some such embodiments, the pathology is shrinkage of neuronal perikarya. According to some such embodiments, the pathology is selective neuronal loss.

According to one embodiment, the leptin or leptin analog thereof is at least one of a leptin fragment, a therapeutically active leptin fragment, a leptin mimic or leptin mimetic, or a leptin derivative. According to some such embodiments, the leptin composition comprises a leptin mimetic, or pharmaceutically acceptable salt thereof. According to some such embodiments, the leptin composition comprises a leptin derivative, or pharmaceutically acceptable salt thereof. According to some such embodiments, the leptin derivative is a leptin peptide, or leptin peptide fragment. According to some such embodiments, the leptin peptide or leption peptide fragment is therapeutically active.

According to another embodiment, the leptin or leptin analog thereof is a pharmaceutically acceptable salt of the leptin or leptin analog.

According to another embodiment, the leptin composition is administered daily. According to another embodiment, the leptin composition is administered weekly. According to another embodiment, the leptin composition is administered monthly.

According to another embodiment, the described invention provides a method for treating Alzheimer's Disease in a subject with uninterrupted cycles of a therapeutically effective amount of a leptin composition. The term "uninterrupted" as used herein means than leptin doses are repetitively administered to a subject for at least 2 cycles, 4 cycles, 12 cycles, 24 cycles, and/or 52 cycles or greater, wherein the periodicity of the cycles is constant, and wherein the greatest duration between the last dose of one cycle and the first dose of the next cycle does not exceed 21 days, 14 days, 7 days, and/or 1 day. Within this definition, the phrase "periodicity of the cycles is constant" means that the duration between corresponding doses in consecutive is constant to within a 12 hour range. For example, if the periodicity is denoted to be 7 days (i.e., 168 hours), then according to the described invention the phrase "periodicity of the cycles is constant" will be construed to mean that the duration between the corresponding doses in consecutive cycles may range from 162 to 174 hours. In some embodiments, the number of leptin composition doses in each cycle can range from 1 to 5, and each individual dose may comprise taking one or a plurality of individual dosage forms. In some embodiments, the number of leptin composition doses in each cycle can range from 1 to 6, and each individual dose may comprise taking one or a plurality of individual dosages forms.

According to another embodiment, the periodicity is daily (i.e., one day). According to another embodiment, the thereapeutically effective amount of the leptin composition is administered in a single cycle. According to some such embodiments, the number of doses in the cycle is one.

According to another embodiment, 1 dose of leptin composition is administered to a subject every 7 days for at least 2 cycles (i.e., bimonthly). According to another embodiment, 1 dose of leptin composition is administered to a subject every 7 days for at least 4 cycles (i.e., monthly). According to another embodiment, 1 dose of leptin composition is administered to a subject every 7 days for at least 52 cycles (i.e., a year). In this case, the number of doses per cycle is only a single dose, the periodicity is 7 days, and the greatest duration between the last dose of one cycle and the first dose of the next cycle is 6 days. In another embodiment, for example, one dose of leptin composition is administered on Monday and one on Tuesday for at least 52 cycles. In this case, the number of doses per cycle is 2, the periodicity is 7 days, and the greatest duration between the last dose of one cycle and the first dose of the next cycle is 5 days (i.e. Wednesday through Sunday). In another embodiment, for example, a dose of leptin composition is administered in the morning and another at night on a particular day of the week by taking two tablets with each dose, this cycle is then repeated for at least 52 cycles. In this case, the number of doses per cycle is 2 where each dose comprises taking 2 dosage forms, the periodicity is 7 days, and the greatest duration between the last dose of one cycle and the first dose of the next cycle is 6 days (i.e. the days between the day of the week the doses are given). It will be understood that other schedules are within the embodiments of the invention. For example, in one embodiment, one dose of leptin composition is administered on Monday and one on Wednesday for at least 52 cycles. In this case, the number of doses per cycle is 2, the periodicity is 7 days, and the greatest duration between the last dose of one cycle and the first dose of the next cycle is 4 days (i.e. Thursday through Sunday). In another embodiment, the periodicity is weekly (i.e. 7 days).

In some embodiments, the inventive composition can be combined with other therapeutic agents and administered locally. In some such embodiments, the inventive composition and the other therapeutic agent(s) are administered simultaneously. When the other therapeutic agents are administered simultaneously, they can be administered in the same or separate formulations, but are administered at the same time. In some such embodiments, the inventive composition and the other therapeutic agent(s) are administered sequentially. The other therapeutic agents are administered sequentially with one another and with inventive composition when the administration of the other therapeutic agents and the inhibitor is temporally separated. The separation in time between the administration of these agents may be a matter of minutes or it may be longer.

According to some embodiments, the leptin composition further comprises at least one second therapeutic agent. According to some such embodiments, the second therapeutic agent is a kinase inhibitor. According to some such embodiments, the second therapeutic agent is an antibiotic agent. According to some such embodiments, the second therapeutic agent is an anti-fungal agent. According to some such embodiments, the second therapeutic agent is an antiviral agent. According to some such embodiments, the second therapeutic agent is an anti-protozoal agent. According to some such embodiments, the second therapeutic agent is a steroidal anti-inflammatory agent. According to some such embodiments, the second therapeutic agent is a non-steroidal anti-inflammatory agent. According to some such embodiments, the second therapeutic agent is an anti-oxidant agent. According to some such embodiments, the second therapeutic agent is a hormone. According to some such embodiments, the second therapeutic agent is a vitamin. According to some such embodiments, the second therapeutic agent is an antihistamine agent. According to some such embodiments, the second therapeutic agent is a chemotherapeutic agent.

According to some embodiments, the leptin composition comprises:

(a) a leptin or leptin analog thereof as a first therapeutic agent;

(b) an optional second therapeutic agent comprising at least one kinase inhibitor, wherein the at least one kinase inhibitor is in a kinase inhibiting amount, and (c) a carrier;

whereby the composition provides kinase inhibition at levels greater than sum of components (a), (b) and (c).

According to one embodiment, the at least one kinase inhibitor is a kinase inhibitor selected from the group consisting of: calcium/calmodulin-dependent protein kinase II, protein kinase A and GSK-3β.

According to another embodiment, the at least one kinase inhibitor is an inhibitor of calcium/calmodulin-dependent protein kinase II (CAMK2A; Myr-AIP). Calcium signaling is crucial for several aspects of plasticity at glutamatergic synapses. Calciuim/calmodulin-dependent kinase II is a kinase enzyme belonging to the serine/threonine protein kinase family, and to the calcium/calmodulin-dependent protein subfamily. This enzyme is composed of four different chain: α, β, Δ and γ. The α chain is required for hippocampal long-term potentiation and spatial learning. In addition to its calcium-calmodulin (CaM)-dependent activity, calcium/calmodulindependent kinase II can undergo autophosphorylation, resulting in CaM-independent activity.

According to another embodiment, the at least one kinase inhibitor is a kinase inhibitor of protein kinase A. Protein kinase A (PKA, cAMP-dependent protein kinase) refers to a family of enzymes whose activity is dependent on the level of cyclic adenosine monophosphate (cAMP) in the cell. PKA has several functions in the cell, including regulation of glycogen, sugar and lipid metabolism. Each PKA is a holoenzyme that consists of two regulatory and two catalytic subunits. Under low levels of cAMP, the holoenzyme remains intact and is catalytically inactive. When the concentration of cAMP increases, cAMP binds to the two binding sites on the regulatory subunits, which leads to the release of catalytic subunits. The free catalytic subunits then can catalzye the transfer of ATP terminal phosphates to protein substrates at serine or threonine residues. This phosphorylation usually results in a change in activity of the substrate. The effects of PKA activity varies with cell type.

According to another embodiment, the at least one kinase inhibitor is a kinase inhibitor of glycogen synthase kinase-3β (GSK-3β). The function of GSK-3β is not entirely understood.

According to another embodiment, the at least one kinase inhibitor is selected from the group consisting of Myr-AIP, LiCl and KT5720.

According to another embodiment, the at least one kinase inhibitor is kinase inhibitor lithium chloride (LiCl). Lithium chloride attenuates GSK-3β activity ($IC_{50}$=5 mM) by increasing the phosphorylation of the inhibitory Ser9 residue. According to some such embodiments, the LiCl concentration is from about $5\times10^{-2}$ mol/L to about 1 mmol/L.

According to another embodiment, the at least one kinase inhibitor is kinase inhibitor 6-bromoindirubin-3'-oxime (BIO). The kinase inhibitor 6-bromoindirubin-3'-oxime ((2'Z,3'E)-6-bromoindirubin-3'-oxime) is a potent, reversible and ATP-competitive GSK-3β inhibitor and the first pharmacological agent shown to maintain self-renewal in human and mouse embryonic stem cells.

According to another embodiment, the at least one kinase inhibitor is kinase inhibitor KT5720. KT5720 is a cell-permeable, semi-synthetic derivative of K525a. It is a selective inhibitor of cAMP-dependent protein kinase (PKA; $IC_{50}$=56 nM) but has no significant effect on protein kinase C(PKC), protein kinase G (PKG) or myosin light chain kinase (MLCK).

According to another embodiment, the at least one kinase inhibitor is a kinase inhibitor selected from the group consisting of K252a, staurosporine, KT5252b and chelerythrine.

According to another embodiment, the at least one kinase inhibitor is kinase inhibitor K252a. K252a is an alkaloid isolated from *Nocardiopisis* sp. soil fungi. This ATP analog is a highly potent cell permeable inhibitor of CaM kinase and phosphorylase kinase ($IC_{50}$=1.8 and 1.7 nM, respectively). At higher concentrations, it also is an efficient inhibitor of serine/threonine protein kinases ($IC_{50}$=10 to 30 nM).

According to another embodiment, the at least one kinase inhibitor is kinase inhibitor K252b. K252b is an alkaloid isolated from *Nocardiopisis* sp. soil fungi. It is a less potent derivative of K252a cell-permeable protein kinase inhibitor. This compound potentiates neurotrophin-3 activity in certain neurons by an unknown mechanism.

According to another embodiment, the at least one kinase inhibitor is kinase inhibitor staurosporine. Staurosporine is a member of the K252a family of fungal alkaloids produced by *Streptomyces* staurospores. It is one of the most potent, cell permeable inhibitors ($IC_{50}$=0.7-20 nM) of protein kinases.

According to another embodiment, the at least one kinase inhibitor is kinase inhibitor chelrythrine. Chelerythine is a potent, cell-permeable inhibitor of protein kinase C ($IC_{50}$=660 nM) that binds to the catalytic domain of PKC. Chelerythrine is at least 100-fold more selective for PKCs than for other kinases.

According to another embodiment, the at least one kinase inhibitor is kinase inhibitor SB216763. SB216763 (3-(2,4-dichlorophenyl)-4-(1-methyl-1H-indol-3-yl)-1H-pyrrole-2,5-dione) is a permeable, structurally distinct maleimide that inhibits GSK-3 activity. This potent and selective inhibitor of GSK-3β ($IC_{50}$=34 nM) stimulates glycogen synthesis in human liver cells and mimics other actions of insulin.

According to another embodiment, the at least one kinase inhibitor is kinase inhibitor TDZD-8 (4-Benzyl-2-methyl-1,2,4-thiadiazolidine-3,5-dione-8). TDZD-8 is a selective inhibitor of GSK-3, a thiadiazolidinone derivative, non-ATP competitive inhibitor of GSK-3β ($IC_{50}$=2 μM). It does not inhibit Cdk-1/cyclin B, CKII, PKA, or PKC at 100 μM. According to some such embodiments, the concentration of TDZD is about $2\times10^{-5}$ mol/L.

According to another embodiment, the therapeutically effective amount of the leptin composition is from about 0.0001 g of a leptin or leptin analog/kg body weight to about 100 g of a leptinor leptin analog/kg body weight. According to another embodiment, the therapeutically effective amount is from about 0.0005 g of a leptin or leptin analog/kg body weight to about 100 g of a leptin or leptin analog/kg body weight. According to another embodiment, the therapeutically effective amount is from about 0.001 g of a leptin or leptin analog/kg body weight to about 100 g of a leptin or leptin analog/kg body weight. According to another embodiment, the therapeutically effective amount is from about 0.002 g of a leptin or leptin analog/kg body weight to about 95 g of a leptin or leptin analog/kg body weight. According to another embodiment, the therapeutically effective amount is from about 0.003 g of a leptin or leptin analog/kg body weight to about 95 g of a leptin or leptin analog/kg body weight. According to another embodiment, the therapeutically effective amount is from about 0.004 g of a leptin or leptin analog/kg body weight to about 95 g of a leptin or leptin analog/kg body weight. According to another embodiment, the therapeutically effective amount is from about 0.005 g of a leptin or leptin analog/kg body weight to about 95 g of a leptin or leptin analog/kg body weight. According to another embodiment, the therapeutically effective amount is from about 0.006 g of a leptin or leptin analog/kg body weight to about 95 g of a leptin or leptin analog/kg body weight. According to another embodiment, the therapeutically effective amount is from about 0.007 g of a leptin or leptin analog/kg body weight to about 95 g of a leptin or leptin analog/kg body weight. According to another embodiment, the therapeutically effective amount is from about 0.008 g of a leptin or leptin analog/kg body weight to about 95 g of a leptin or leptin analog/kg body weight. According to another embodiment, the therapeutically effective amount is from about 0.009 g of a leptin or leptin analog/kg body weight to about 95 g of a leptin or leptin analog/kg body weight. According to another embodiment, the therapeutically effective amount is from about 0.01 g of a leptin or leptin analog/kg body weight to about 95 g of a leptin or leptin analog/kg body weight. According to another embodiment, the therapeutically effective amount is from about 0.01 g of a leptin or leptin analog/kg body weight to about 90 g of a leptin or leptin analog/kg body weight. According to another embodiment, the therapeutically effective amount is from about 0.01 g of a leptin or leptin analog/kg body weight to about 85 g of a leptin or leptin analog/kg body weight. According to another embodiment, the therapeutically effective amount is from about 0.01 g of a leptin or leptin analog/kg body weight to about 80 g of a leptin or leptin analog/kg body weight. According to another embodiment, the therapeutically effective amount is from about 0.01 g of a leptin or leptin analog/kg body weight to about 75 g of a leptin or leptin analog/kg body weight. According to another embodiment, the therapeutically effective amount is from about 0.01 g of a leptin or leptin analog/kg body weight to about 70 g of a leptin or leptin analog/kg body weight. According to another embodiment, the therapeutically effective amount is from about 0.01 g of a leptin or leptin analog/kg body weight to about 65 g of a leptin or leptin analog/kg body weight. According to another embodiment, the therapeutically effective amount is from about 0.01 g of a leptin or leptin analog/kg body weight to about 60 g of a leptin or leptin analog/kg body weight. According to another embodiment, the therapeutically effective amount is from about 0.01 g of a leptin or leptin analog/kg body weight to about 55 g of a leptin or leptin analog/kg body weight. According to another embodiment, the therapeutically effective amount is from about 0.01 g of a leptin or leptin analog/kg body weight to about 50 g of a leptin or leptin analog/kg body weight. According to another embodiment, the therapeutically effective amount is from about 0.01 g of a leptin or leptin analog/kg body weight to about 45 g of a leptin or leptin analog/kg body weight. According to another embodiment, the therapeutically effective amount is from about 0.01 g of a leptin or leptin analog/kg body weight to about 40 g of a leptin or leptin analog/kg body weight. According to another embodiment, the therapeutically effective amount is from about 0.01 g of a leptin or leptin analog/kg body weight to about 35 g of a leptin or leptin analog/kg body weight. According to another embodiment, the therapeutically effective amount is from about 0.01 g of a leptin or leptin analog/kg body weight to about 30 g of a leptin or leptin analog/kg body weight. According to another embodiment, the therapeutically effective amount is from about 0.01 g of a leptin or leptin analog/kg body weight to about 25 g of a leptin or leptin analog/kg body weight. According to another embodiment, the therapeutically effective amount is from about 0.01 g of a leptin or leptin analog/kg body weight to about 20 g of a leptin or leptin analog/kg body weight. According to another embodiment, the therapeutically effective amount is from about 0.01 g of a leptin or leptin analog/kg body weight to about 15 g of a leptin or leptin analog/kg body weight. According to another embodiment, the therapeutically effective amount is from about 0.01 g of a leptin or leptin analog/kg body weight to about 10 g of a leptin or leptin analog/kg body weight. According to another embodiment, the therapeutically effective amount is from about 0.01 g of a leptin or leptin analog/kg body weight to about 5 g of a leptin or leptin analog/kg body weight. According to another embodiment, the therapeutically effective amount is from about 0.01 g of a leptin or leptin analog/kg body weight to about 4 g of a leptin or leptin analog/kg body weight. According to another embodiment, the therapeutically effective amount is from about 0.01 g of a leptin or leptin analog/kg body weight to about 3 g of a leptin or leptin analog/kg body weight. According to another embodiment, the therapeutically effective amount is from about 0.01 g of a leptin or leptin analog/kg body weight to about 2 g of a leptin or leptin analog/kg body weight. According to another embodiment, the therapeutically effective amount is from about 0.01 g of a leptin or leptin analog/kg body weight to about 1 g of a leptin or leptin analog/kg body weight. According to another embodiment, the therapeutically effective amount is from about 0.01 g of a leptin or leptin analog/kg body weight to about 500 g of a leptin or leptin analog/kg body weight. According to another embodiment, the therapeutically effective amount is from about 0.01 g of a leptin or leptin analog/kg body weight to about 250 g of a leptin or leptin analog/kg body weight. According to another embodiment, the therapeutically effective amount is from about 0.01 g of a leptin or leptin analog/kg body weight to about 100 g of a leptin or leptin analog/kg body weight. According to another embodiment, the therapeutically effective amount is from about 0.01 g of a leptin or leptin analog/kg body weight to about 50 g of a leptin or leptin analog/kg body weight. According to another embodiment, the therapeutically effective amount is from about 0.01 g of a leptin or leptin analog/kg body weight to about 25 g of a leptin or leptin analog/kg body weight. According to another embodiment, the therapeutically effective amount is from about 0.01 g of a leptin or leptin analog/kg body weight to about 10 g of a leptin or leptin analog/kg body weight. According to another embodiment, the therapeutically effective amount is from about 0.01 g of a leptin or leptin analog/kg body weight to about 5 g of a leptin or leptin analog/kg body weight. According to another embodiment, the therapeutically effective amount is from about 0.01 g of a leptin or leptin analog/kg body weight to about 1 g of a leptin or leptin analog/kg body weight.

(2). Method for Improving Resilience of Cognitive Function

According to another aspect, the described invention provides a method for improving resilience of cognitive function in a subject in need thereof, the method comprising the steps of (a) administering to the subject a leptin composition comprising:

(i) a cognitive function-enhancing amount of a leptin or a leptin analog as a first therapeutic agent;

(ii) optionally, at least one optional second therapeutic agent; and (iii) a pharmaceutically acceptable carrier; and (b) improving resilience of cognitive function in the subject.

According to another embodiment, the leptin or leptin analog comprises a leptin, a therapeutically active leptin fragment, a leptin mimetic, a leptin derivative, or pharmaceutically acceptable salt thereof.

According to some embodiments, the leptin composition further comprises at least one optional second therapeutic agent. According to some such embodiments, the optional second therapeutic agent is a kinase inhibitor. According to another embodiment, the optional second therapeutic agent is an antibiotic. According to another embodiment, the optional second therapeutic agent is an anti-fungal agent. According to another embodiment, the optional second therapeutic agent is an anti-viral agent. According to another embodiment, the optional second therapeutic agent is an anti-protozoal agent. According to another embodiment, the optional second therapeutic agent is a steroidal anti-inflammatory agent. According to another embodiment, the optional second therapeutic agent is a non-steroidal anti-inflammatory agent. According to another embodiment, the optional second therapeutic agent is an anti-oxidant. According to another embodiment, the optional second therapeutic agent is a hormone. According to another embodiment, the optional second therapeutic agent is a vitamin. According to another embodiment, the optional second therapeutic agent is an antihistamine agent. According to another embodiment, the optional second therapeutic agent is a chemotherapetic agent.

According to another embodiment, the cognitive function-enhancing amount is from about 0.0001 g of a leptin or leptin analog/kg body weight to about 100 g of a leptin or leptin analog/kg body weight. According to another embodiment, the cognitive function-enhancing amount is from about 0.0005 g of a leptin or leptin analog/kg body weight to about 100 g of a leptin or leptin analog/kg body weight. According to another embodiment, the cognitive function-enhancing amount is from about 0.001 g of a leptin or leptin analog/kg body weight to about 100 g/kg body weight. According to another embodiment, the cognitive function-enhancing amount is from about 0.002 g of a leptin or leptin analog/kg /kg body weight to about 100 g/kg body weight. According to another embodiment, the cognitive function-enhancing amount is from about 0.003 g of a leptin or leptin analog/kg /kg body weight to about 100 g of a leptin or leptin analog/kg body weight. According to another embodiment, the cognitive function-enhancing amount is from about 0.004 g of a leptin or leptin analog/kg body weight to about 100 g of a leptin or leptin analog/kg body weight. According to another embodiment, the cognitive function-enhancing amount is from about 0.005 g of a leptin or leptin analog/kg body weight to about 100 g of a leptin or leptin analog/kg body weight. According to another embodiment, the cognitive function-enhancing amount is from about 0.006 g of a leptin or leptin analog/kg body weight to about 100 g of a leptin or leptin analog/kg body weight. According to another embodiment, the cognitive function-enhancing amount is from about 0.007 g of a leptin or leptin analog/kg body weight to about 100 g of a leptin or leptin analog/kg body weight. According to another embodiment, the cognitive function-enhancing amount is from about 0.008 g of a leptin or leptin analog/kg body weight to about 100 g of a leptin or leptin analog/kg body weight. According to another embodiment, the cognitive function-enhancing amount is from about 0.009 g of a leptin or leptin analog/kg body weight to about 100 g of a leptin or leptin analog/kg body weight. According to another embodiment, the cognitive function-enhancing amount is from about 0.01 g of a leptin or leptin analog/kg body weight to about 95 g of a leptin or leptin analog/kg body weight. According to another embodiment, the cognitive function-enhancing amount is from about 0.01 g of a leptin or leptin analog/kg body weight to about 90 g of a leptin or leptin analog/kg body weight. According to another embodiment, the cognitive function-enhancing amount is from about 0.01 g of a leptin or leptin analog/kg body weight to about 85 g of a leptin or leptin analog/kg body weight. According to another embodiment, the cognitive function-enhancing amount is from about 0.01 g of a leptin or leptin analog/kg body weight to about 80 g of a leptin or leptin analog/kg body weight. According to another embodiment, the cognitive function-enhancing amount is from about 0.01 g of a leptin or leptin analog/kg body weight to about 75 g of a leptin or leptin analog/kg body weight. According to another embodiment, the cognitive function-enhancing amount is from about 0.01 g of a leptin or leptin analog/kg body weight to about 70 g of a leptin or leptin analog/kg body weight. According to another embodiment, the cognitive function-enhancing amount is from about 0.01 g of a leptin or leptin analog/kg body weight to about 65 g of a leptin or leptin analog/kg body weight. According to another embodiment, the cognitive function-enhancing amount is from about 0.01 g of a leptin or leptin analog/kg body weight to about 60 g of a leptin or leptin analog/kg body weight. According to another embodiment, the cognitive function-enhancing amount is from about 0.01 g of a leptin or leptin analog/kg body weight to about 55 g of a leptin or leptin analog/kg body weight. According to another embodiment, the cognitive function-enhancing amount is from about 0.01 g of a leptin or leptin analog/kg body weight to about 50 g of a leptin or leptin analog/kg body weight. According to another embodiment, the cognitive function-enhancing amount is from about 0.01 g of a leptin or leptin analog/kg body weight to about 45 g of a leptin or leptin analog/kg body weight. According to another embodiment, the cognitive function-enhancing amount is from about 0.01 g of a leptin or leptin analog/kg body weight to about 40 g of a leptin or leptin analog/kg body weight. According to another embodiment, the cognitive function-enhancing amount is from about 0.01 g of a leptin or leptin analog/kg body weight to about 35 g of a leptin or leptin analog/kg body weight. According to another embodiment, the cognitive function-enhancing amount is from about 0.01 g of a leptin or leptin analog/kg body weight to about 30 g of a leptin or leptin analog/kg body weight. According to another embodiment, the cognitive function-enhancing amount is from about 0.01 g of a leptin or leptin analog/kg body weight to about 25 g of a leptin or leptin analog/kg body weight. According to another embodiment, the cognitive function-enhancing amount is from about 0.01 g of a leptin or leptin analog/kg body weight to about 20 g of a leptin or leptin analog/kg body weight. According to another embodiment, the cognitive function-enhancing amount is from about 0.01 g of a leptin or leptin analog/kg body weight to about 15 g of a leptin or leptin analog/kg body weight. According to another embodiment, the cognitive function-enhancing amount is from about 0.01 g of a leptin or leptin analog/kg body weight to about 10 g of a leptin or leptin analog/kg body weight. According to another embodiment, the cognitive function-enhancing amount is from about 0.01 g of a leptin or leptin analog/kg body weight to about 5 g of a leptin or leptin analog/kg body weight. According to another embodiment, the cognitive function-enhancing amount is from about 0.01 g of a leptin or leptin analog/kg body weight to about 4 g of a leptin or leptin analog/kg body weight. According to another embodiment, the cognitive function-enhancing amount is from about 0.01 g of a leptin or leptin analog/kg body weight to about 3 g of a leptin or leptin analog/kg body weight. According to another embodiment, the cognitive function-enhancing amount is from about 0.01 g of a leptin or leptin analog/kg body weight to about 2 g of a leptin or leptin analog/kg body weight. According to another embodiment, the cognitive function-enhancing amount is from about 0.01 g of a leptin or leptin analog/kg body weight to about 1 g of a leptin or leptin analog/kg body weight. According to another embodiment, the cognitive function-enhancing amount is from about 0.01 g of a leptin or leptin analog/kg body weight to about 500 g/kg body weight. According to another embodiment, the cognitive function-enhancing amount is from about 0.01 g/kg body weight to about 250 g/kg body weight. According to another embodiment, the cognitive function-enhancing amount is from about 0.01 g of a leptin or leptin analog/kg /kg body weight to about 100 g/kg body weight. According to another embodiment, the cognitive function-enhancing amount is from about 0.01 g of a leptin or leptin analog/kg /kg body weight to about 50 g/kg body weight. According to another embodiment, the cognitive function-enhancing amount is from about 0.01 g of a leptin or leptin analog/kg /kg body weight to about 25 g/kg body weight. According to another embodiment, the cognitive function-enhancing amount is from about 0.01 g of a leptin or leptin analog/kg /kg body weight to about 10 g/kg body weight. According to another embodiment, the cognitive function-enhancing amount is from about 0.01 g/kg body weight to about 5 g of a leptin or leptin analog/kg /kg body weight. According to another embodiment, the cognitive function-enhancing amount is from about 0.01 g/kg body weight to about 1 g/kg body weight.

According to another embodiment, the cognitive function enhancing amount of leptin composition is administered daily. According to another embodiment, the cognitive function enhancing amount of leptin composition is administered weekly. According to another embodiment, the cognitive function enhancing amount of leptin composition is administered monthly.

According to another embodiment, the cognitive function enhancing amount of leptin composition enhances a cognitive function, wherein the cognitive function is memory. According to some embodiments, the cognitive function enhancing amount of leptin composition enhances a cognitive function, wherein the cognitive function is a conditioned memory. According to some embodiments, the cognitive function enhancing amount of leptin composition enhances a cognitive function, wherein the cognitive function is a contextual memory.

According to another embodiment, the cognitive function enhancing amount of leptin composition enhances a cognitive function, wherein the cognitive function is learning. According to some embodiments, the cognitive function enhancing amount of leptin composition enhances a cognitive function, wherein the cognitive function is a contextual learning. According to some embodiments, the cognitive function enhancing amount of leptin composition enhances a cognitive function, wherein the cognitive function is a conditioned learning.

According to another embodiment, the cognitive function enhancing amount of leptin composition enhances a cognitive function, wherein the cognitive function is memory retention.

According to some embodiments, the ameliorating a cognitive function to its original cognitive function level is of at least about 10% of the original cognitive function level. According to some embodiments, the ameliorating a cognitive function to its original cognitive function level is of at least about 25% of the original cognitive function level. According to some embodiments, the ameliorating a cognitive function to its original cognitive function level is of 50% of the original cognitive function level. According to some embodiments, the ameliorating a cognitive function to its original cognitive function level is of at least about 75% of the original cognitive function level.

(1). Compositions for Decreasing Tau Phosphorylation

According to another aspect of the described invention, the composition of the invention for decreasing tau phosphorylation comprises:

(a) a leptin or leptin analog;

(b) an optional second therapeutic agent comprising at least one kinase inhibitor, wherein the at least one kinase inhibitor is in a kinase inhibiting amount; and (c) a carrier;

whereby the composition provides inhibition of at least one kinase at levels greater than sum of components (a), (b) and (c).

According to one embodiment, the leptin or leptin analog thereof is at least one of a leptin, a therapeutically active leptin fragment, a leptin mimic or leptin mimetic, or a leptin derivative. According to some such embodiments, the leptin derivative is a leptin peptide, or leptin peptide fragment.

According to another embodiment, the leptin or leptin analog thereof is a pharmaceutically acceptable salt of the leptin or leptin analog.

According to one embodiment, the at least one kinase inhibitor is at least one kinase inhibitor selected from the group consisting of a kinase inhibitor of calcium/calmodulin-dependent protein kinase II, a kinase inhibitor of protein kinase A and a kinase inhibitor of GSK-3β.

According to another embodiment, the at least one kinase inhibitor is an inhibitor of calcium/calmodulin-dependent protein kinase II (CAMK2A; Myr-AIP). According to another embodiment, the at least one kinase inhibitor is a kinase inhibitor of protein kinase A (PKA, cAMP-dependent protein kinase). According to another embodiment, the at least one kinase inhibitor is a kinase inhibitor of GSK-3β.

According to another embodiment, the at least one kinase inhibitor is at least one kinase inhibitor selected from the group consisting of Myr-AIP, LiCl and KT5720.

According to another embodiment, the at least one kinase inhibitor is kinase inhibitor lithium chloride (LiCl). Lithium chloride attenuates GSK-3β activity ($IC_{50}$=5 mM) by increasing the phosphorylation of the inhibitory Ser9 residue. According to some such embodiments, the LiCl concentration is from about $5 \times 10^{-2}$ mol/L to about 1 mmol/L.

According to another embodiment, the at least one kinase inhibitor is kinase inhibitor 6-bromoindirubin-3'-oxime ((2'Z,3'E)-6-bromoindirubin-3'-oxime) (BIO), a potent, reversible and ATP-competitive GSK-3β inhibitor.

According to another embodiment, the at least one kinase inhibitor is kinase inhibitor KT5720, a cell-permeable, semi-synthetic derivative of K525a, and a selective inhibitor of cAMP-dependent protein kinase (PKA; $IC_{50}$=56 nM).

According to another embodiment, the at least one kinase inhibitor is a kinase inhibitor selected from the group consisting of K252a, staurosporine, KT5252b and chelerythrine.

According to another embodiment, the at least one kinase inhibitor is kinase inhibitor K252a, an ATP analog and a highly potent cell permeable inhibitor of CaM kinase and phosphorylase kinase ($IC_{50}$=1.8 nM and 1.7 nM, respectively), and, at higher concentrations, also an efficient inhibitor of serine/threonine protein kinases ($IC_{50}$=10 nM to 30 nM).

According to another embodiment, the at least one kinase inhibitor is kinase inhibitor K252b, an alkaloid isolated from *Nocardiopisis* sp. soil fungi and a less potent derivative of K252a cell-permeable protein kinase inhibitor that potentiates neurotrophin-3 activity in certain neurons by an unknown mechanism.

According to another embodiment, the at least one kinase inhibitor is kinase inhibitor staurosporine, a cell permeable inhibitor ($IC_{50}$=0.7 nM to 20 nM) of protein kinases.

According to another embodiment, the at least one kinase inhibitor is kinase inhibitor chelrythrine, a potent, cell-permeable inhibitor of protein kinase C(PKC) ($IC_{50}$=660 nM) that binds to the catalytic domain of PKC. According to another embodiment, the at least one kinase inhibitor is kinase inhibitor SB216763 (3-(2,4-dichlorophenyl)-4-(1-methyl-1H-indol-3-yl)-1H-pyrrole-2,5-dione), a permeable, structurally distinct maleimide that selectively inhibits GSK-3β ($IC_{50}$=34 nM), stimulates glycogen synthesis in human liver cells and mimics other actions of insulin.

According to another embodiment, the at least one kinase inhibitor is kinase inhibitor TDZD-8 (4-Benzyl-2-methyl-1,2,4-thiadiazolidine-3,5-dione-8), a selective, non-ATP competitive inhibitor of GSK-3β ($IC_{50}$=2 μM) that does not inhibit Cdk-1/cyclin B, CKII, PKA, or PKC at ? 100 μM. According to some such embodiments, the concentration of TDZD is about $2 \times 10^{-5}$ mol/L.

According to another embodiment, the carrier is a pharmaceutical carrier.

Compositions

The compositions described herein are delivered in therapeutically effective amounts. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular therapeutically active leptin or leptin analog and optional second therapeutic agent, being administered, the size of the subject, or the severity of the disease or condition. One of ordinary skill in the art may determine empirically the effective amount of a particular leptin composition and/or other therapeutic agent without necessitating undue experimentation. It generally is preferred that a maximum dose be used, that is, the highest safe dose according to some medical judgment. "Dose" and "dosage" are used interchangeably herein.

For any compound described herein the therapeutically effective amount initially may be determined from preliminary in vitro studies and/or animal models. A therapeutically effective dose may also be determined from human data for a leptin or leptin analog and optional second therapeutic agent, which has been tested in humans and for compounds which are known to exhibit similar pharmacological activities, such as other related active agents. The applied dose may be adjusted based on the relative bioavailability and potency of the administered compound or composition. Adjusting the dose to achieve maximal efficacy based on the methods described above and other methods as are well-known in the art is well within the capabilities of the ordinarily skilled artisan.

The formulations of a leptin composition comprising a leptin or leptin analog and optional second therapeutic agent, may be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the leptin composition comprising a leptin or leptin analog and optional second therapeutic agent, may be administered to a subject by any mode that delivers the leptin composition to the desired surface. Administering the pharmaceutical composition may be accomplished by any means known to the skilled artisan. Routes of administration include, but are not limited to, intrathecal, intra-arterial, parenteral (e.g. intravenous), or intramuscular, orally, buccally, intranasally, rectally, or topically.

The inhibitors and other therapeutics may be delivered to a subject during surgery to treat an underlying condition or symptom of a pathology resulting from accumulation of NFTs or Aβ.

Oral Compositions

The compositions of the described invention may be in a form suitable for oral use, for example, as tablets, troches, lozenges, aqueous or oily suspensions, dispersible powders or granules, emulsions, hard or soft capsules or syrups or elixirs. As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually). Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled release.

Compositions of the described invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the described invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the described invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Compositions of the described invention may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, for example, sweetening, flavoring and coloring agents, also may be present.

The compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the described invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded (meaning torn or cut) tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

Buccal Compositions

For buccal administration, the compositions of the described invention may take the form of tablets or lozenges formulated in a conventional manner.

Parenteral Compositions

The compositions of the described invention may be in the form of a sterile injectable aqueous or oleaginous suspension. The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the described invention is delivered using a needle, e.g., a surgical needle. The term "surgical needle" as used herein, refers to any needle adapted for delivery of fluid (i.e., capable of flow) compositions of the described invention into a selected anatomical structure. Injectable preparations, such as sterile injectable aqueous or oleaginous suspensions, may be formulated according to the known art using suitable dispersing or wetting agents and suspending agents.

The leptin composition, when it is desirable to deliver it locally, may be formulated for parenteral administration by injection, e.g., by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The leptin composition comprising leptin or leptin analog and an optional second therapeutic agent may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the described invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids also may be made.

The formulations may be presented conveniently in unit dosage form and may be prepared by any of the methods well known in the art of pharmacy. All methods include the step of bringing into association a leptin composition comprising leptin or leptin analog and an optional second therapeutic agent ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly (orthoesters) and poly(anhydrides). Depot injectable formulations are also prepared by entrapping the drug in liposomes or microemulsions which are compatible with body tissues.

Locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The leptin composition comprising a leptin or leptin analog and an optional second therapeutic agent may be provided in particles. The term "particles" as used herein refers to nano- or microparticles (or in some instances larger) that may contain in whole or in part the leptin composition comprising a leptin or leptin analog and an optional second therapeutic agent. The particles may contain the leptin or leptin analog and an optional second therapeutic agent in a core surrounded by a coating. The leptin or leptin analog and an optional second therapeutic agent also may be dispersed throughout the particles. The leptin or leptin analog and an optional second therapeutic agent also may be adsorbed into the particles. The particles may be of any order release kinetics, including zero order release, first order release, second order release, delayed release, sustained release, immediate release, etc., and any combination thereof. The particle may include, in addition to the leptin or leptin analog and an optional second therapeutic agent, any of those materials routinely used in the art of pharmacy and medicine, including, but not limited to, erodible, nonerodible, biodegradable, or nonbiodegradable material or combinations thereof. The particles may be microcapsules that contain the leptin or leptin analog and an optional second therapeutic agent in a solution or in a semi-solid state. The particles may be of virtually any shape.

Both non-biodegradable and biodegradable polymeric materials may be used in the manufacture of particles for delivering the leptin or leptin analog and an optional second therapeutic agent. Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

Insufflation Compositions

The compositions of the described invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. Spray drying, for example, is a process in which a homogeneous aqueous mixture of drug and the carrier is introduced via a nozzle (e.g., a two fluid nozzle), spinning disc or an equivalent device into a hot gas stream to atomize the solution to form fine droplets. The aqueous mixture may be a solution, suspension, slurry, or the like, but needs to be homogeneous to ensure uniform distribution of the components in the mixture and ultimately the powdered composition. The solvent, generally water, rapidly evaporates from the droplets producing a fine dry powder having particles from about 1 μm to 5 μm in diameter. The spray drying is done under conditions that result in a substantially amorphous powder of homogeneous constitution having a particle size that is respirable, a low moisture content and flow characteristics that allow for ready aerosolization. Preferably the particle size of the resulting powder is such that more than about 98% of the mass is in particles having a diameter of about 10 μm or less with about 90% of the mass being in particles having a diameter less than 5 μm. Alternatively, about 95% of the mass will have particles with a diameter of less than 10 μm with about 80% of the mass of the particles having a diameter of less than 5 μm. Dry powder compositions also may be prepared by lyophilization and jet milling, as disclosed in International Patent Publication No. WO 91/16038, the disclosure of which are incorporated by reference.

The term "dispersibility" or "dispersible" means a dry powder having a moisture content of less than about 10% by weight (% w) water, usually below about 5% w and less than about 3% w; a particle size of about 1.0-5.0 µm mass median diameter (MMD), of about 1.0-4.0 µm MMD, and of about 1.0-3.0 µm MMD; a delivered dose of about >30%, about >40%, about >50%, and about >60%; and an aerosol particle size distribution of about 1.0-5.0 µm mass median aerodynamic diameter (MMAD), about 1.5-4.5 µm MMAD, and about 1.5-4.0 µm MMAD. Methods and compositions for improving dispersibility are disclosed in U.S. application Ser. No. 08/423,568, filed Apr. 14, 1995, the disclosure of which is hereby incorporated by reference.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 microns (µm) in diameter with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content such that the particles are readily dispersible in an inhalation device to form an aerosol. This moisture content is generally below about 10% by weight (% w) water, usually below about 5% w and preferably less than about 3% w.

The amount of the pharmaceutically acceptable carrier is that amount needed to provide the necessary stability, dispersibility, consistency and bulking characteristics to ensure a uniform pulmonary delivery of the composition to a subject in need thereof. Numerically the amount may be from about 0.05% w to about 99.95% w, depending on the activity of the drug being employed. Preferably about 5% w to about 95% will be used. The carrier may be one or a combination of two or more pharmaceutical excipients, but generally will be substantially free of any "penetration enhancers." Penetration enhancers are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. The dry powder compositions of the described invention described invention are readily absorbed in the lungs without the need to employ penetration enhancers.

The types of pharmaceutical excipients that are useful as carriers for pulmonary delivery include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable for pulmonary delivery include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, trehalose, raffinose, maltodextrins, and mannitol. Suitable polypeptides include aspartame. Amino acids include alanine and glycine, with glycine being preferred.

Additives, which are minor components of the composition for pulmonary delivery, may be included for conformational stability during spray drying and for improving dispersibility of the powder. These additives include hydrophobic amino acids such as tryptophan, tyrosine, leucine, phenylalanine, and the like.

For delivery by inhalation or insufflation, the composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (for example, air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

The compositions of the described invention may be used in the form of drops or sprays (e.g., a nasal spray, aerosol spray, or pump spray) or other vehicles for nasal administration (intranasal delivery). Aerosol spray preparations can be contained in a pressurized container with a suitable propellant such as a hydrocarbon propellant. Pump spray dispensers can dispense a metered dose or a dose having a specific particle or droplet size. Any dispensing device can be arranged to dispense only a single dose, or a multiplicity of doses. More generally, compositions of the invention, especially those formulated for intranasal administration, can also be provided as solutions, suspensions, or viscous compositions (e.g., gels, lotions, creams, or ointments).

Rectal Compositions

The compositions of the described invention may be in the form of suppositories for rectal administration of the composition. "Rectal" or "rectally" as used herein refers to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

Topical Compositions

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system," "transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for post-menopausal indications, and nicotine for smoking cessation.

Patches suitable for use in the described invention include, but are not limited to, (1) the matrix patch; (2) the reservoir patch; (3) the multi-laminate drug-in-adhesive patch; and (4) the monolithic drug-in-adhesive patch; Transdermal and Topical Drug Delivery Systems, pp. 249-297 (Tapash K. Ghosh et al. eds., 1997), hereby incorporated herein by reference. These patches are well known in the art and generally available commercially.

Carriers and Other Components

In some embodiments, the compositions of the described invention may be formulated with an excipient, vehicle or carrier selected from solvents, suspending agents, binding agents, fillers, lubricants, disintegrants, and wetting agents/surfactants/solubilizing agents. The terms "excipient", "vehicle", or "carrier" refer to substances that facilitate the use of, but do not deleteriously react with, the active compound(s) when mixed with it. The term "active" refers to the ingredient, component or constituent of the compositions of the described invention responsible for the intended therapeutic effect. Carriers must be of sufficiently high purity and of sufficiently low toxicity to render them suitable for administration to the subject being treated. The carrier can be inert, or it can possess pharmaceutical benefits.

The carrier can be liquid or solid and is selected with the planned manner of administration in mind to provide for the desired bulk, consistency, etc., when combined with an active and the other components of a given composition. Typical pharmaceutical carriers include, but are not limited to, binding agents (including, but not limited to, pregelatinized maize starch, polyvinylpyrrolidone or hydroxypropyl methylcellulose); fillers (including, but not limited to, lactose and other sugars, microcrystalline cellulose, pectin, gelatin, calcium sulfate, ethyl cellulose, polyacrylates or calcium hydrogen phosphate.); lubricants (including, but not limited to, magnesium stearate, talc, silica, sollidal silicon dioxide, stearic acid, metallic stearates, hydrogenated vegetable oils, corn starch, polyethylene glycols, sodium benzoate, sodium acetate); disintegrants (including, but not limited to, starch, sodium starch glycolate) and wetting agents (including, but not limited to, sodium lauryl sulfate). Additional suitable carriers for the compositions of the described invention include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, for example, lubricants, preservatives, stabilizers, wetting agents, emulsifiers, salts for influencing osmotic pressure, buffers, colorings, flavoring and/or aromatic substances and the like which do not deleteriously react with the active compounds.

The term "pharmaceutically acceptable carrier" as used herein refers to any substantially non-toxic carrier conventionally useful for administration of pharmaceuticals in which the active component will remain stable and bioavailable. In some embodiments, the pharmaceutically acceptable carrier of the compositions of the described invention include a release agent such as a sustained release or delayed release carrier. In such embodiments, the carrier can be any material capable of sustained or delayed release of the leptin or leptin analog and optional second therapeutic agent active ingredient to provide a more efficient administration, resulting in less frequent and/or decreased dosage of the active ingredient, ease of handling, and extended or delayed effects. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

In some embodiments, the compositions of the described invention can further include one or more compatible active ingredients aimed at providing the composition with another pharmaceutical effect in addition to that provided by the leptin or leptin analog and optional second therapeutic agent. "Compatible" as used herein means that the active ingredients of such a composition are capable of being combined with each other in such a manner so that there is no interaction that would substantially reduce the efficacy of each active ingredient or the composition under ordinary use conditions. In another aspect of the described invention, the composition also may be administered serially or in combination with other compositions for treating diseases, conditions or disorders resulting from accumulation of amyloid peptides. For example, without limitation, such other compositions may include monoclonal antibodies (such as monoclonal anti-β-Amyloids and monoclonal anti-β-secretases); and anti-inflammatory compounds (including, but not limited to nonsteroidal anti-inflammatory drugs (NSAIDs), such as ibuprofen, indomethacin, and flurbiprofen). Anti-inflammatory compounds have been shown to direct Aβ-lowering properties in cell cultures as well as in transgenic models of AD-like amyloidosis.

The concentration of the active substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the described invention to be used for an intended purpose. Additionally, in therapeutic applications of the described invention, compositions or medicants are administered to a patient suspected of, having, or already suffering from, such a disease, disorder or condition in an amount sufficient to cure, or at least partially arrest, the symptoms of the disease, disorder or condition, including its complications and intermediate pathological phenotypes in development of the disease, disorder or condition. In some methods, administration of the composition of the described invention reduces or eliminates cognitive impairment in patients that have not yet developed characteristic pathology of the disease, disorder or condition.

An amount adequate to accomplish therapeutic or prophylactic treatment is defined herein as a therapeutically-effective dose. In both prophylactic and therapeutic regimes, an amount of the compositions of the described invention is usually administered in several dosages until a sufficient beneficial response has been achieved. Typically, the response is monitored and repeated dosages are given if the response starts to wane. A skilled artisan can determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual $ED_{50}$. The use of the term "individual" distinguishes the $ED_{50}$ based on the intensity of effect as used herein from the median effective dose, also abbreviated $ED_{50}$, determined from frequency of response data in a population. "Efficacy" as used herein refers to the property of the compositions of the described invention to achieve the desired response, and "maximum efficacy" refers to the maximum achievable effect. The amount of compounds in the compositions of the described invention which will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, N.Y., 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the described invention are those large enough to produce the desired therapeutic effect. The therapeutically effective amount of the compositions of the described invention may be administered one or more times per day on a regular basis. A typical dose administered to a subject is between about 0.0001 mg of the composition per kg (of body weight) per day and about 10 g of the composition per kg (of body weight) per day. For example, without limitation, the minimum dose of the composition is contemplated as about 0.0001 mg/kg/day, about 0.0005 mg/kg/day, about 0.001 mg/kg/day, about 0.002 mg/kg/day, about 0.004 mg/kg/day, about 0.004 mg/kg/day, about 0.005 mg/kg/day, about 0.006 mg/kg/day, about 0.007 mg/kg/day, about 0.008 mg/kg/day, about 0.009 mg/kg/day, about 0.01 mg/kg/day, about 0.025 mg/kg/day, about 0.05 mg/kg/day, about 0.075 mg/kg/day, about 0.08 mg/kg/day, about 0.1 mg/kg/day, about 0.125 mg/kg/day, about 0.15 mg/kg/day, about 0.175 mg/kg/day, about 0.2 mg/kg/day, about 0.225 mg/kg/day, about 0.25 mg/kg/day, about 0.275 mg/kg/day, about 0.3 mg/kg/day, about 0.325 mg/kg/day, about 0.35 mg/kg/day, about 0.375 mg/kg/day, about 0.4 mg/kg/day, about 0.45 mg/kg/day, about 0.475 mg/kg/day, or about 0.5 mg/kg/day and the maximum dose is contemplated as about 10 g/kg/day, about 9 g/kg/day, about 8 g/kg/day, about 7 g/kg/day, about 6 g/kg/day, about 5 g/kg/day, about 4 g/kg/day, about 3 g/kg/day, about 2 g/kg/day, about 1 g/kg/day, about 0.5 g/kg/day, about 0.2 g/kg/day, about 0.175 g/kg/day, about 0.15 g/kg/day, about 0.125 g/kg/day, about 0.1 g/kg/day, about 0.08 g/kg/day, about 0.075 g/kg/day, about 0.05 g/kg/day, about 0.025 g/kg/day, or about 0.01 g/kg/day. In some embodiments of the invention in humans, the dose may be about 0.0001 mg to about 10 g of the composition per kg (of body weight) per day, and in other embodiments in humans, between 0.0001 and 10 g of the composition per kg (of body weight) per day.

Additional compositions of the described invention can be prepared readily using technology is known in the art, such as that which is described in Remington's Pharmaceutical Sciences, 18th or 19th editions, published by the Mack Publishing Company of Easton, Pa., which is incorporated herein by reference.

According to another embodiment of the method, the method comprises the step of implanting surgically or injecting a leptin composition in gel, slow-release solid or semi-solid form into the patient to deliver drug substance at the site of interest. Because this leptin composition is delivered specifically (locally) to the site, the dosage required to treat the progressive cognitive disorder may reduce, prevent or circumvent any toxicity that may prevent the administration of higher systemic doses.

Controlled Release Systems

The leptin composition of the described invention may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form.

The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. The term "long-term" release, as used herein, means that the implant is constructed and arranged to deliver therapeutic levels of the active ingredient for at least about 7 days, at least about 10 days, at least about 14 days, at least about 21 days, at least about 30, at least about 45 days, to about 60 days. Long-term sustained release implants are well-known to those of ordinary skill in the art and include some of the release systems described above.

According to another embodiment, the pharmaceutically acceptable carrier of the described invention includes a sustained release or delayed release carrier. The carrier can be any material capable of sustained or delayed release of the compound to provide a more efficient administration resulting in less frequent and/or decreased dosage of the compound, ease of handling, and extended or delayed effects on epithelial-related conditions.

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment, it is preferred that the therapeutic dosage be close to the maximum tolerated dose. For chronic preventive use, lower dosages may be desirable because of concerns about long term effects.

The effectiveness of the compositions and methods of the described invention can be assayed by a variety of protocols. The effects of increasing cognitive function in a human subject can be determined by methods routine to those skilled in the art including, but not limited to, both paper and pencil and computer tests. One of skill in the art also can directly measure amyloid peptide accumulation levels, neurofibrillary tangle formation and neurodegeneration in animal models. Furthermore, amyloid peptide may be measured in a sample of a subject's cerebrospinal fluid (CSF) obtained by spinal tap. One measure of accumulation of an amyloid peptide is an increase in levels circulating in the blood of a subject. Such levels may be measured by Sandwich Enzyme-linked-Immunoabsorbent-Assays (ELISAs), using a pair of antibodies, one for capture and the other for detection. These methods are well known by those of ordinary skill in the art.

III. Drug Discovery

Since there have been few studies of the metabolic pathways triggered by leptin in AD pathobiology, the described invention further provides drug discovery methods related to treating a progressive cognitive dysfunction disease or disorder resulting from accumulations of NFTs or Aβ utilizing the discovery that 5-adenosine monophosphate protein kinase (AMPK), which physiologically functions as a metabolic and stress sensor, mediates leptin's ability to reduce tau phosphorylation and Aβ release.

(1). Method for the Identification of Therapeutic Agents to Treat or Prevent a Cognitive Dysfunction Disease or Disorder According to another aspect, the described invention provides a method for identifying an effective therapeutic agent for treating or preventing a progressive cognitive dysfunction disease or disorder that results from at least one of Aβ acumulation, tau hyperphosphorylation, or NFT accumulation, the method comprising the steps:

a) providing a cell culture comprising neuronal cells;
b) contacting the cell culture comprising neuronal cells with a putative therapeutic agent;
c) determining whether the putative therapeutic agent associates with an active portion of an AMPK protein such that it affects activity of the AMPK protein contacted by the putative therapeutic agent; and
d) identifying the putative therapeutic agent as an effective therapeutic agent for treating the progressive cognitive dysfunction disease or disorder that results from at least one of Aβ acumulation, tau hyperphosphorylation, or NFT accumulation by measuring secretion of amyloid-beta by the neuronal cells in the culture relative to controls.

According to one embodiment, the progressive cognitive dysfunction results from accumulation of neurofibrillary tangles. According to another embodiment, the progressive cognitive dysfunction results from accumulation of amyloid β.

According to some embodiments, the progressive cognitive disease or disorder that results from at least one of Aβ acumulation, tau hyperphosphorylation, or NFT accumulation includes, but is not limited to, Alzheimer's disease, progressive supranuclear palsy; dementia; dementia pugilistica; Creutzfeldt-Jakob disease; frontotemporal dementia; Pick's disease; other tau-positive pathology including FTDP-17 corticobasal degeneration; frontotemporal lobar degeneration (FTLD); and dementia lacking distinctive histology. According to another embodiment, the progressive cognitive disorder is Alzheimer's disease. According to another embodiment, the progressive cognitive disorder is progressive supranuclear palsy. According to another embodiment, the progressive cognitive disorder is dementia. According to another embodiment, the progressive cognitive disorder is dementia pugilistica. According to another embodiment, the progressive cognitive disorder is Creutzfeldt-Jakob disease. According to another embodiment, the progressive cognitive disorder is frontotemporal dementia. According to another embodiment, the progressive cognitive disorder is Pick's disease. According to another embodiment, the progressive cognitive disorder is FTDP-17 corticobasal degeneration. According to another embodiment, the progressive cognitive disorder is frontotemporal lobar degeneration (FTLD). According to another embodiment, the progressive cognitive disorder is dementia lacking distinctive histology.

According to another embodiment, the putative therapeutic agent is of an amount sufficient for inhibiting AMPK protein. According to another embodiment, the putative therapeutic agent is of an amount from about 1 ng/ml to about 100 μg/ml. According to some such embodiments, the putative therapeutic agent is of an amount of about 5 ng/ml. According to some such embodiments, the putative therapeutic agent is of an amount of about 25 ng/ml. According to some such embodiments, the putative therapeutic agent is of an amount of about 50 ng/ml. According to some such embodiments, the putative therapeutic agent is of an amount of about 75 ng/ml. According to some such embodiments, the putative therapeutic agent is of an amount of about 100 ng/ml. According to some such embodiments, the putative therapeutic agent is of an amount of about 250 ng/ml. According to some such embodiments, the putative putative therapeutic agent is of an amount of about 500 ng/ml. According to some such embodiments, the putative therapeutic agent is of an amount of about 750 ng/ml. According to some such embodiments, the putative therapeutic agent is of an amount of about 1 μg/ml. According to some such embodiments, the putative therapeutic agent is of an amount of about 25 μg/ml. According to some such embodiments, the putative therapeutic agent is of an amount of about 50 μg/ml. According to some such embodiments, the putative therapeutic agent is of an amount of about 75 μg/ml. According to some such embodiments, the putative therapeutic agent is of an amount of about 100 μg/ml.

According to another embodiment, the putative therapeutic agent is a recombinant protein. According to another embodiment, the putative therapeutic agent that is a recombinant protein is expressed by recombinant DNA. The term "expressed" as used herein refers to a process by which inheritable information from a gene, such as a DNA sequence, is made into a functional gene product. Recombinant DNA (rDNA) is a DNA sequence formed by the joining, usually in vitro, of two non-homologous DNA molecules. According to some embodiments, the recombinant protein is a protein that associates with AMPK. According to some such embodiments, the recombinant protein is an inhibitor of AMPK. According to some such embodiments, the recombinant protein is an AMPK antagonist. According to some such embodiments, the recombinant protein is an AMPK agonist.

According to another embodiment, the putative therapeutic agent is an inhibitor. According to some such embodiments, the inhibitor is an AMPK inhibitor. According to another embodiment, the putative therapeutic agent is an antagonist. According to some such embodiments, the putative therapeutic agent is an AMPK antagonist.

According to some embodiments, the antagonist may be identified using a functional antagonist assay. In a functional antagonist assay, the $IC_{so}$ of a drug can be determined by constructing a dose-response curve and examining the effect of different concentrations of antagonist on reversing agonist activity. $IC_{50}$ values can be calculated for a given antagonist by determining the concentration needed to inhibit half of the maximum biological response of the agonist. $IC_{50}$ values are dependent on conditions under which they are measured. In general, $IC_{50}$ value increases as enzyme concentration increases, and the higher the concentration of inhibitor, the more that agonist activity will be lowered. According to some embodiments, the $IC_{50}$ value of the antagonist identified is from about 0.001 nM to about 25 µM. According to some embodiments, the $IC_{50}$ value of the antagonist is from about 0.001 nM to about 10 µM. According to some embodiments, the $IC_{50}$ value of the antagonist is from about 0.001 nM to about 1 µM. According to some embodiments, the $IC_{50}$ value of the antagonist is from about 0.001 nM to about 500 nM. According to some embodiments, the $IC_{50}$ value of the antagonist is from about 0.001 nM to about 250 nM. According to some embodiments, the $IC_{50}$ value of the antagonist is from about 0.001 nM to about 100 nM. According to some embodiments, the $IC_{so}$ value of the antagonist is from about 0.001 nM to about 50 nM. According to some embodiments, the $IC_{50}$ value of the antagonist is from about 0.001 nM to about 25 nM.

According to some embodiments, the anatagonist may be identified using a competition binding assay. In a competition binding assay, a single concentration of a radioligand (usually an agonist) is used in each assay well. The ligand is used at a low concentration, usually at or below its dissociation constant (Kd) value. The level of specific binding of the radioligand then is determined in the presence of a range of concentrations of other competing non-radioactive compounds (usually antagonists), in order to measure the potency with which they compete for the binding of the radioligand. Competition curves also may be computer-fitted to a logistic function as described under direct fit. In this situation, the $IC_{50}$ is the concentration of competing ligand which displaces 50% of the specific binding of the radioligand. The $IC_{50}$ value is converted to an absolute inhibition constant (Ki) using the Cheng-Prusoff equation $K_i=((IC_{50})/(1+([S]/Km)))$ where Ki is the binding affinity of the inhibitor, $IC_{50}$ is the functional strength of the inhibitor, [S] is substrate concentration, and Km is the affinity of the substrate for the enzyme. The $IC_{50}$ value for a compound may vary between experiments, depending upon the radioligand concentration, however, the Ki is an absolute value. The $K_i$ is the inhibition constant for the drug; the concentration of competing ligand in a competition assay which would occupy 50% of the receptors if no radioligand were present. According to some embodiments, the $IC_{50}$ value of the antagonist is from about 0.001 nM to about 25 µM. According to some embodiments, the $IC_{50}$ value of the antagonist is from about 0.001 nM to about 10 µM. According to some embodiments, the $IC_{50}$ value of the antagonist is from about 0.001 nM to about 1 µM. According to some embodiments, the $IC_{50}$ value of the antagonist is from about 0.001 nM to about 500 nM. According to some embodiments, the $IC_{50}$ value of the antagonist is from about 0.001 nM to about 250 nM. According to some embodiments, the $IC_{50}$ value of the antagonist is from about 0.001 nM to about 100 nM. According to some embodiments, the $IC_{50}$ value of the antagonist is from about 0.001 nM to about 50 nM. According to some embodiments, the $IC_{50}$ value of the antagonist is from about 0.001 nM to about 25 nM.

According to another embodiment, the putative therapeutic agent is an agonist. According to some such embodiments, the putative therapeutic agent is an AMPK agonist. According to some such embodiments, the AMPK agonist is a AICAR peptidomimetic. For agonist and stimulator assays, the most common summary measure is the $EC_{50}$. The potency of an agonist is inversely related to its half maximal effective concentration ($EC_{50}$). Concentration measures typically follow a sigmoidal curve, increasing rapidly over a relatively small change in concentration. According to some embodiments, the $EC_{50}$ value of the antagonist is from about 0.001 nM to about 25 nM. According to some embodiments, the $EC_{50}$ value of the antagonist is from about 0.001 nM to about 50 nM. According to some embodiments, the $EC_{50}$ value of the antagonist is from about 0.001 nM to about 100 nM. According to some embodiments, the $EC_{50}$ value of the antagonist is from about 0.001 nM to about 250 nM. According to some embodiments, the $EC_{50}$ value of the antagonist is from about 0.001 nM to about 500 nM. According to some embodiments, the $EC_{50}$ value of the antagonist is from about 0.001 nM to about 1 µM. According to some embodiments, the $EC_{50}$ value of the antagonist is from about 0.001 nM to about 10 µM. According to some embodiments, the $EC_{50}$ value of the antagonist is from about 0.001 nM to about 25 µM.

According to another embodiment, the putative therapeutic agent is an antibody. According to some such embodiments, the antibody is an antibody against AMPK. According to another embodiment, the measuring secretion of amyloid-beta by the neuronal cells in the culture relative to controls in step (c) is by an ELISA assay. According to another embodiment, measuring secretion of amyloid-beta by the neuronal cells in the culture relative to controls in step (c) is by immunoblot.

According to another embodiment, the method further comprises the step of using the effective therapeutic agent for treating an amyloid-beta pathology.

According to one such embodiment, the amyloid-beta (Aβ) pathology is Alzheimer's Disease. According to some embodiments, the amyloid-beta pathology of AD comprises a missense mutation in APP, presenilin 1 (PS1) or presenilin 2 (PS2) gene.

According to some embodiments, the amyloid-beta pathology of AD comprises an altered proteolysis of $Aβ_{42}$.

According to some embodiments, the amyloid-beta pathology of AD comprises a progressive accumulation and aggregation of $Aβ_{42}$ in brain interstitial fluid.

According to some embodiments, the amyloid-beta pathology of AD comprises a deposition of aggregated $Aβ_{42}$ as diffuse plaques. According to some such embodiments, the deposition further comprises proteoglycans and other amyloid-promoting substrates.

According to some embodiments, the amyloid-beta pathology of AD comprises an aggregation of $Aβ_{40}$ onto diffuse Aβ$_{42}$ plaques. According to some embodiments, the amyloid-beta pathology of AD comprises an accrual of certain plaque-associated proteins.

According to some embodiments, the amyloid-beta pathology of AD comprises an inflammatory response. According to some such embodiments, the inflammatory response is at least one of microglial activation, cytokine release, astrocytosis, and acute phase protein release.

According to some embodiments, the amyloid-beta pathology of AD comprises a progressive neuritic injury. In some such embodiments, the progressive neuritic injury is within amlyoid plaques. In some such embodiments, the progressive neuritic injury is within amyloid plaques and elsewhere in the neuropil.

According to some embodiments, the amyloid-beta pathology of AD comprises a disruption of neuronal metabolic homeostasis. According to some embodiments, the amyloid-beta pathology of AD comprises a disruption of ionic homeostasis. According to some embodiments, the amyloid-beta pathology of AD comprises oxidative injury.

According to some embodiments, the amyloid-beta pathology of AD comprises at least one altered kinase/phosphatase activity leading to hyperphosphorlyated tau which leads to PHF formation.

According to some embodiments, the pathology of AD comprises widespread neuronal/neuritic dysfunction and death in the hippocampus and the cerebral cortex with progressive neurotransmitter deficits.

According to some embodiments, the amyloid-beta pathology of AD comprises dementia.

According to some embodiments, the amyloid-beta pathology of AD affects the cortical regions. According to some such embodiments, the amyloid-beta pathology of AD comprises neuritic dystrophy. According to some such embodiments, the amyloid-beta pathology of AD comprises synaptic loss. According to some such embodiments, the amyloid-beta pathology of AD comprises shrinkage of neuronal perikarya. According to some such embodiments, the amyloid-beta pathology of AD comprises selective neuronal loss.

According to another embodiment, the Aβ pathology is Huntington's disease. McGowan, D P, et al, Neuroscience 100(4): 677-80 (2000). Huntington's disease (chorea) is a neurodegenerative disorder that affects muscle coordination and some cognitive functions. A physical examination, sometimes combined with a psychological examination, can determine whether the onset of the disease has begun. Excessive unintentional movements of any part of the body are often the reason for seeking medical consultation. If these are abrupt and have random timing and distribution, it suggests a diagnosis of HD. Cognitive or psychiatric symptoms rarely are the first diagnosed; they are usually only recognized in hindsight or when they develop further. How far the disease has progressed can be measured using the unified Huntington's disease rating scale which provides an overall rating system based on motor, behavioral, cognitive, and functional assessments. Medical imaging, such as computerized tomography (CT) and magnetic resonance imaging (MRI), generally shows visible cerebral atrophy in the advanced stages of the disease. Functional neuroimaging techniques such as fMRI and PET can show changes in brain activity before the onset of physical symptoms. The most characteristic initial physical symptoms are jerky, random, and uncontrollable movements called chorea. Chorea may be initially exhibited as general restlessness, small unintentionally initiated or uncompleted motions, lack of coordination, or slowed saccadic eye movements. These minor motor abnormalities usually precede more obvious signs of motor dysfunction by at least three years. The clear appearance of symptoms such as rigidity, writhing motions or abnormal posturing appear as the disorder progresses. These are signs that the system in the brain that is responsible for movement is affected. Psychomotor functions become increasingly impaired, such that any action that requires muscle control is affected. Common consequences are physical instability, abnormal facial expression, and difficulties chewing, swallowing and speaking Eating difficulties commonly cause weight loss and may lead to malnutrition. Sleep disturbances are also associated symptoms. Juvenile HD differs from these symptoms in that it generally progresses faster and chorea is exhibited briefly, if at all, with rigidity being the dominant symptom. Seizures also are a common symptom of this form of HD. Cognitive abilities are impaired progressively. Especially affected are executive functions which include planning, cognitive flexibility, abstract thinking, rule acquisition, initiating appropriate actions and inhibiting inappropriate actions. As the disease progresses, memory deficits tend to appear. Reported impairments range from short-term memory deficits to long-term memory difficulties, including deficits in episodic (memory of one's life), procedural (memory of the body of how to perform an activity) and working memory. Cognitive problems tend to worsen over time, ultimately leading to dementia. This pattern of deficits has been called a "subcortical dementia" syndrome to separate it from the typical effects of "cortical dementias" such as Alzheimer's disease.

According to another embodiment, the Aβ pathology is Parkinson's disease. (See, e.g., Conway, K A, et al, Biochemistry 39: 2552-63 (2000); Hardy, J. and Selkoe, D J, Science 297: 353-56 (2002)). Parkinson's disease (PD) is a degenerative disorder of the central nervous system. PD affects movement, producing motor symptoms. Non-motor symptoms include autonomic dysfunction, cognitive and neurobehavioral problems, and sensory and sleep difficulties. Four major symptoms of PD include: tremor, rigidity, bradykinesia and akinesia, and postural instability. Additional symptoms include, but are not limited to, slowed reaction time, executive dysfunction, dementia, and short term memory loss.

According to another embodiment, the effective therapeutic agent is of an amount sufficient for inhibiting AMPK protein. According to some such embodiments, the effective therapeutic agent is of an amount from about 1 ng/ml to about 100 µg/ml. According to some such embodiments, the effective therapeutic agent is of an amount of about 5 ng/ml. According to some such embodiments, the effective therapeutic agent is of an amount of about 25 ng/ml. According to some such embodiments, the effective therapeutic agent is of an amount of about 50 ng/ml. According to some such embodiments, the effective therapeutic agent is of an amount of about 75 ng/ml. According to some such embodiments, the effective therapeutic agent is of an amount of about 100 ng/ml. According to some such embodiments, the effective therapeutic agent is of an amount of about 250 ng/ml. According to some such embodiments, the effective therapeutic agent is of an amount of about 500 ng/ml. According to some such embodiments, the effective therapeutic agent is of an amount of about 750 ng/ml. According to some such embodiments, the effective therapeutic agent is of an amount of about 1 µg/ml. According to some such embodiments, the effective therapeutic agent is of an amount of about 25 µg/ml. According to some such embodiments, the effective therapeutic agent is of an amount of about 50 µg/ml. According to some such embodiments, the effective therapeutic agent is of an amount of about 75 µg/ml. According to some such embodiments, the effective therapeutic agent is of an amount of about 100 µg/ml.

According to another embodiment, the effective therapeutic agent is a recombinant protein. According to some embodiments, the recombinant protein is a protein that associates with AMPK. According to some such embodiments, the recombinant protein is an inhibitor of AMPK. According to some such embodiments, the recombinant protein is an AMPK agonist. According to some such embodiments, the recombinant protein is an AMPK antagonist.

According to another embodiment, the effective therapeutic agent is an inhibitor. According to some such embodiments, the effective therapeutic agent is an AMPK inhibitor.

According to another embodiment, the effective therapeutic agent is an antagonist. According to some such embodiments, the effective therapeutic agent is an AMPK antagonist.

According to some embodiments, the antagonist may be identified using a functional antagonist assay. According to some embodiments, the $IC_{50}$ value of the antagonist identified is from about 0.001 nM to about 25 µM. According to some embodiments, the $IC_{50}$ value of the antagonist identified is from about 0.001 nM to about 10 µM. According to some embodiments, the $IC_{50}$ value of the antagonist identified is from about 0.001 nM to about 1 µM. According to some embodiments, the $IC_{50}$ value of the antagonist identified is from about 0.001 nM to about 500 nM. According to some embodiments, the $IC_{50}$ value of the antagonist identified is from about 0.001 nM to about 250 nM. According to some embodiments, the $IC_{50}$ value of the antagonist identified is from about 0.001 nM to about 100 nM. According to some embodiments, the $IC_{50}$ value of the antagonist identified is from about 0.001 nM to about 50 nM. According to some embodiments, the $IC_{50}$ value of the antagonist identified is from about 0.001 nM to about 25 nM.

According to some embodiments, the anatagonist may be identified using a competition binding assay. According to some embodiments, the $IC_{50}$ value of the antagonist identified is from about 0.001 nM to about 25 µM. According to some embodiments, the $IC_{50}$ value of the antagonist identified is from about 0.001 nM to about 10 µM. According to some embodiments, the $IC_{50}$ value of the antagonist identified is from about 0.001 nM to about 1 µM. According to some embodiments, the $IC_{50}$ value of the antagonist identified is from about 0.001 nM to about 500 nM. According to some embodiments, the $IC_{50}$ value of the antagonist identified is from about 0.001 nM to about 250 nM. According to some embodiments, the $IC_{50}$ value of the antagonist identified is from about 0.001 nM to about 100 nM. According to some embodiments, the $IC_{50}$ value of the antagonist identified is from about 0.001 nM to about 50 nM. According to some embodiments, the $IC_{50}$ value of the antagonist identified is from about 0.001 nM to about 25 nM.

According to another embodiment, the effective therapeutic agent is an agonist. According to some such embodiments, the effective therapeutic agent is an AMPK agonist.

According to another embodiment, the effective therapeutic agent is an antibody.

According to some such embodiments, the effective therapeutic agent is an antibody against AMPK.

According to another embodiment, the effective therapeutic agent inhibits at least one AMPK function.

(2). Method for the Identification of Effectors of Tau Phosphorylation

NFTs are a prominent hallmark of AD and are composed primarily of hyperphosphorylated tau protein that has polymerized into straight and PHFs. Tau protein is normally very soluble and functions to regulate neuronal microtuble dynamics. Although tau's function is normally modulated via controlled phosphorylation and dephosphorylation, the pathological deregulation of tau phosphorylation generally is believed to correlate with dementia in AD, and further appears to precede polymerization and NFT formation. The kinase(s) responsible for the hyperphosphorylation of tau in AD has (have) not been identified, although tau is phosphorylated readily by numerous kinases.

Glycogen synthase kinase 3β (GSK3β) is a constitutively active proline-directed serine-threonine kinase that mediates the addition of phosphate molecules in certain serine and threonine amino acids in a particular cellular substrate. It generally is believed that GSK-3β inhibits these substrates via phosphorylation. Most GSK-3β substrates are under negative regulation, which is relieved by Ser9 phosphorylation through other kinases such as protein kinase C(PKC), protein kinase A (PKA) and protein kinase B (Akt).

In addition to being abnormally polymerized, tau has been shown to be hyperphosphorylated in AD pathology. It is not known how hyperphosphorylated tau is generated, although GSK-3β may have a role.

According to another aspect, the described invention provides a method to identify at least one effector of tau phosphorylation, the method comprising the steps:

a) providing a cell culture comprising neuronal cells;
b) contacting the cell culture with an effector-candidate,
c) determining whether the effector-candidate associates with an active portion of a GSK-3β protein such that it affects activity of the GSK-3β protein contacted by the effector-candidate; and
d) identifying the effector-candidate as an effector of tau phosphorylation by measuring GSK-3β protein activity by the neuronal cells in the culture relative to controls;

According to one embodiment, the effector is of an amount sufficient for inhibiting GSK-3β protein. According to another embodiment, the effector is of an amount from about 1 ng/ml to about 100 µg/ml. According to some such embodiments, the effector is of an amount of about 5 ng/ml. According to some such embodiments, the effector is of an amount of about 25 ng/ml. According to some such embodiments, the effector is of an amount of about 50 ng/ml. According to some such embodiments, the effector is of an amount of about 75 ng/ml. According to some such embodiments, the effector is of an amount of about 100 ng/ml. According to some such embodiments, the effector is of an amount of about 250 ng/ml. According to some such embodiments, the effector is of an amount of about 500 ng/ml. According to some such embodiments, the effector is of an amount of about 750 ng/ml. According to some such embodiments, the effector is of an amount of about 1 µg/ml. According to some such embodiments, the effector is of an amount of about 25 µg/ml. According to some such embodiments, the effector is of an amount of about 50 µg/ml. According to some such embodiments, the effector is of an amount of about 75 µg/ml. According to some such embodiments, the effector is of an amount of about 100 µg/ml.

According to another embodiment, the effector is a recombinant protein. According to some embodiments, the recombinant protein is an effector that associates with GSK-3β. According to some such embodiments, the recombinant protein is an effector that inhibits GSK-3β. According to some such embodiments, the recombinant protein is an effector that is an agonist of GSK-3β. According to some such embodiments, the recombinant protein is an effector that is an antagonist of GSK-3β.

According to another embodiment, the effector is an inhibitor. According to some such embodiments, the effector is an inhibitor of GSK-3β.

According to another embodiment, the effector is an antagonist. According to some such embodiments, the effector is an GSK-3β antagonist.

According to some embodiments, the antagonist may be identified using a functional antagonist assay. According to some embodiments, the $IC_{50}$ value of the antagonist identified is from about 0.001 nM to about 25 μM. According to some embodiments, the $IC_{50}$ value of the antagonist identified is from about 0.001 nM to about 10 μM. According to some embodiments, the $IC_{50}$ value of the antagonist identified is from about 0.001 nM to about 1 μM. According to some embodiments, the $IC_{50}$ value of the antagonist identified is from about 0.001 nM to about 500 nM. According to some embodiments, the $IC_{50}$ value of the antagonist identified is from about 0.001 nM to about 250 nM. According to some embodiments, the $IC_{50}$ value of the antagonist identified is from about 0.001 nM to about 100 nM. According to some embodiments, the $IC_{50}$ value of the antagonist identified is from about 0.001 nM to about 50 nM. According to some embodiments, the $IC_{50}$ value of the antagonist identified is from about 0.001 nM to about 25 nM.

According to some embodiments, the anatagonist may be identified using a competition binding assay. According to some embodiments, the $IC_{50}$ value of the antagonist identified is from about 0.001 nM to about 25 μM. According to some embodiments, the $IC_{50}$ value of the antagonist identified is from about 0.001 nM to about 10 μM. According to some embodiments, the $IC_{50}$ value of the antagonist identified is from about 0.001 nM to about 1 μM. According to some embodiments, the $IC_{50}$ value of the antagonist identified is from about 0.001 nM to about 500 nM. According to some embodiments, the $IC_{50}$ value of the antagonist identified is from about 0.001 nM to about 250 nM. According to some embodiments, the $IC_{50}$ value of the antagonist identified is from about 0.001 nM to about 100 nM. According to some embodiments, the $IC_{50}$ value of the antagonist identified is from about 0.001 nM to about 50 nM. According to some embodiments, the $IC_{50}$ value of the antagonist identified is from about 0.001 nM to about 25 nM.

According to another embodiment, the effector is an agonist. According to some such embodiments, the effector is an GSK-3β agonist.

According to another embodiment, the effector is an antibody. According to some such embodiments, the effector is an antibody against GSK-3β.

According to another embodiment, identifying step (c) is by an ELISA assay. According to another embodiment, identifying step (c) is by immunoblot.

(4). Method for Identifying a Leptin Blocking Agent

Synthetic peptides may be used as probes to see where protein- peptide interactions occur Inhibitory peptides (blocking agents) may be used in clinical research to examine the effects of peptides on the inhibition of protein kinases, cancer proteins and other disorders.

For example, extracellular signal-regulated kinase (ERK), a MAPK protein kinase [meaning any of a group of protein serine/threonine kinases that respond to extracellular stimuli (antigens) and regulate various cellular activities], is essential for cellular proliferation and differentiation. The activation of MAPKs requires a cascade mechanism whereby MAPK is phosphorylated by an upstream MAPKK (MEK) which then, in turn, is phosphorylated by a third kinase MAPKKK (MEKK). MAPK, which contains the amino-terminal 13 amino acids of MEK1 and binds to ERK, functions as a MEK decoy by binding to ERK. MAPK binding blocks ERK activation by MEK, since ERK is unable to interact with MEK.

Autocamtide-2 related inhibitory peptide (AIP) is another example of a blocking peptide. This synthetic peptide is a highly specific and potent inhibitor of $Ca^{2+}$/calmodulin-dependent protein kinase II (CaMKII). AIP is a non-phosphorylatable analog of autocamtide-2, a highly selective peptide substrate for CaMKII. AIP inhibits CaMKII with an $IC_{50}$ of 100 nM ($IC_{50}$ is a concentration of the inhibitor required to obtain 50% inhibition). The AIP inhibition is non-competitive with respect to syntide-2 (CaMKII Peptide Substrate) and ATP but competitive with respect to autocamtide-2. AIP inhibition is unaffected by the presence or absence of $C\alpha 2+$/calmodulin. CaMKII activity is completely inhibited by 1 μM AIP; PKA, PKC and CaMKIV are not affected.

Cyclin-dependent kinase 5 (Cdk5) inhibitory peptides (CIPs) are another example of blocking peptides. Cdk5 phosphorylates tau at Alzheimer's Disease (AD)-specific phospho-epitopes when it associates with the p25 regulatory component. p25 is a truncated activator of the Cdk-p25 heterodimer (a microtubule associated protein), which is produced from the physiological Cdk5 activator p35 upon exposure to amyloid-beta peptides. CIPs selectively inhibit p25/Cdk5 activity and suppress the aberrant tau phosphorylation in cortical neurons. The reasons for the specificity demonstrated by CIP are not fully understood.

Additional blocking peptides have been identified for ERK2, ERK3, p38/HOG1, protein kinase C, casein kinase II, $Ca^{2+}$/calmodulin kinase IV, casein kinase II, Cdk4, Cdk5, DNA-PK, PAK3, PI-3 kinase, PI-5 kinase, PSTAIRE, ribosomal S6 kinase, GSK-4, GCK, SAPK, SEK1, and FAK.

According to another aspect, the described invention provides a method for identifying a blocking agent of leptin, the method comprising the steps of:

(a) providing a cell culture comprising neuronal cells;

(b) contacting the neuronal cells in the cell culture with a leptin or leptin analog;

(c) contacting the neuronal cells in the cell culture with a putative blocking agent of leptin, wherein the putative blocking agent associates with an active portion of the leptin or leptin analog, and (d) identifying the putative blocking agent as an active blocking agent of leptin by measuring the neuronal cell GSK-3β activity;

(d) According to one embodiment, the blocking agent is of an amount sufficient for inhibiting leptin. According to another embodiment, the blocking agent is of an amount from about 1 ng/ml to about 100 μg/ml. According to some such embodiments, the blocking agent is of an amount of about 5 ng/ml. According to some such embodiments, the blocking agent is of an amount of about 25 ng/ml. According to some such embodiments, the blocking agent is of an amount of about 50 ng/ml. According to some such embodiments, the blocking agent is of an amount of about 75 ng/ml. According to some such embodiments, the blocking agent is of an amount of about 100 ng/ml. According to some such embodiments, the blocking agent is of an amount of about 250 ng/ml. According to some such embodiments, the blocking agent is of an amount of about 500 ng/ml. According to some such embodiments, the blocking agent is of an amount of about 750 ng/ml. According to some such embodiments, the blocking agent is of an amount of about 1 μg/ml. According to some such embodiments, the blocking agent is of an amount of about 25 μg/ml. According to some such embodiments, the blocking agent is of an amount of about 50 μg/ml. According to some such embodiments, the blocking agent is of an amount of about 75 μg/ml. According to some such embodiments, the blocking agent is of an amount of about 100 μg/ml.

According to another embodiment, the blocking agent is a recombinant protein. According to some embodiments, the recombinant protein is a blocking agent that associates with a leptin. According to some such embodiments, the recombinant protein is a blocking agent that inhibits a leptin. According to some such embodiments, the recombinant protein is a blocking agent that is an agonist of a leptin. According to some such embodiments, the recombinant protein is a blocking agent that is an antagonist of a leptin.

According to another embodiment, the blocking agent is an inhibitor. According to some such embodiments, the blocking agent is an inhibitor of a leptin.

According to another embodiment, the blocking agent is an antagonist. According to some such embodiments, the blocking agent is a leptin antagonist.

According to some embodiments, the antagonist may be identified using a functional antagonist assay. According to some embodiments, the $IC_{50}$ value of the antagonist identified is from about 0.001 nM to about 25 µM. According to some embodiments, the $IC_{50}$ value of the antagonist identified is from about 0.001 nM to about 10 µM. According to some embodiments, the $IC_{50}$ value of the antagonist identified is from about 0.001 nM to about 1 µM. According to some embodiments, the $IC_{50}$ value of the antagonist identified is from about 0.001 nM to about 500 nM. According to some embodiments, the $IC_{50}$ value of the antagonist identified is from about 0.001 nM to about 250 nM. According to some embodiments, the $IC_{50}$ value of the antagonist identified is from about 0.001 nM to about 100 nM. According to some embodiments, the $IC_{50}$ value of the antagonist identified is from about 0.001 nM to about 50 nM. According to some embodiments, the $IC_{50}$ value of the antagonist identified is from about 0.001 nM to about 25 nM.

According to some embodiments, the anatagonist may be identified using a competition binding assay. According to some embodiments, the $IC_{50}$ value of the antagonist identified is from about 0.001 nM to about 25 µM. According to some embodiments, the $IC_{50}$ value of the antagonist identified is from about 0.001 nM to about 10 µM. According to some embodiments, the $IC_{50}$ value of the antagonist identified is from about 0.001 nM to about 1 µM. According to some embodiments, the $IC_{50}$ value of the antagonist identified is from about 0.001 nM to about 500 nM. According to some embodiments, the $IC_{50}$ value of the antagonist identified is from about 0.001 nM to about 250 nM. According to some embodiments, the $IC_{50}$ value of the antagonist identified is from about 0.001 nM to about 100 nM. According to some embodiments, the $IC_{50}$ value of the antagonist identified is from about 0.001 nM to about 50 nM. According to some embodiments, the $IC_{50}$ value of the antagonist identified is from about 0.001 nM to about 25 nM.

According to another embodiment, the blocking agent is an agonist. According to some such embodiments, the blocking agent is a leptin agonist.

According to another embodiment, the blocking agent is an antibody. According to some such embodiments, the blocking agent is an antibody against a leptin or leptin analog.

According to another embodiment, the measuring the neuronal cell GSK-3β activity in step (d) is by an ELISA assay. According to another embodiment, measuring the neuronal cell GSK-3β activity in step (d) is by immunoblot.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

The described invention may be embodied in other specific forms without departing from the spirit or essential attributes thereof and, accordingly, reference should be made to the appended claims, rather than to the foregoing specification, as indicating the scope of the invention.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Effects of Chronic Leptin-Treatment on AD-Like Pathobiology and Cognitive Decline Using a Transgenic CRND8 Mouse Model System 1.1. Materials and Methods
1.1(a). Reagents and Antibodies
Alzheimer precursor protein (APP) 643-695 monoclonal antibody (mAb) was purchased from Millipore (Billerica, Mass.). Rabbit anti-PPARγ and —SOCS3, Tau (pSer$^{396}$) mAb and tau (tau46) mAb were purchased from Cell Signaling. PHF-tau mAb (clone AT8) was purchased from Pierce Biotechnology (Rockford, Ill.). PHF-1 mAb was a gift from Dr. Peter Davies, Albert Einstein College of Medicine (Bronx, N.Y.). Rabbit anti-tau (pThr$^{181}$) was purchased from Sigma-Aldrich. Rabbit anti-α-tubulin, -Leptin and -Leptin receptor (OB-R) were purchased from Affinity BioReagents (Golden, Colo.).

1.1(b). Animals and Housing CRND8 mice (n=22) carrying the APP695 gene with double mutations at KM670/671/NL (Swedish mutation), along with V717F (Indiana mutation) on a C3H/He-057BL/6 background and wild-type mice (n=20) were used in this study. All animals were group housed upon arrival and provided ad libitum access to food and water, and maintained on a 12 hour light/dark cycle. All animals were treated following approved protocols by The Institutional Animal Care and Use Committee (IACUC) of Case Western Reserve University and experimental groups were determined in a random fashion. All animals were weighed 3 times during the study as a general measure of health status.

1.1(c). Leptin Pump Implantation

Pump implantations were carried out as follows. Briefly, mice were anesthetized with intraperitoneal injection of Avertin, and then surgically fitted with a subcutaneous Alzet miniosmotic pump (model 2004, Durect Corp., Cupertino, Calif., USA). 13 of the CRND8 animals received a daily dose of 20 μg Leptin in PBS (0.25 μl/h of 3.33 mg/ml recombinant murine Leptin); and 9 were infused with PBS; all wild-type mice were infused with PBS. Refilled osmotic pumps replaced old ones at 4 weeks for a total of 8 weeks of treatment.

1.1(d). ELISAs

All assays were performed according to manufacturer's specific instructions. Levels of all serum markers were calculated from a standard curve developed with OD at 450 nm versus serial dilutions of known concentration.

Mouse insulin levels in serum were determined using the Mouse Insulin ELISA Kit (Millipore). Briefly, this assay is a Sandwich ELISA based, sequentially, on: 1) capture of insulin molecules from samples to the wells of a microtiter plate coated by pre-titered amount of a monoclonal mouse anti-rat insulin antibodies and the binding of biotinylated polyclonal antibodies to the captured insulin, 2) wash-away of unbound materials from samples, 3) binding of horseradish peroxidase to the immobilized biotinylated antibodies, 4) wash-away of free enzyme conjugates, and 5) quantification of immobilized antibody-enzyme conjugates by monitoring horseradish peroxidase activities in the presence of the substrate 3,3',5,5'-tetramethylbenzidine. Enzyme activity is measured spectrophotometrically by increased absorbency at 450 nm, corrected from the absorbency at 590 nm, after acidification of formed products. Since the increase in absorbency is directly proportional to the amount of captured insulin in the unknown sample, the latter can be derived by interpolation from a reference curve generated in the same assay with reference standards of known concentrations of rat insulin.

Mouse α-TNF levels in serum were determined using the Mouse TNFα ELISA kit (R&D Systems; Minneapolis, Minn.). Briefly, this assay employs the quantitative sandwich enzyme immunoassay technique. A microplate is precoated with a polyclonal antibody specific for mouse TNF-α. Standards, controls, and samples are pipetted into the wells and any mouse TNF-α present is bound by the immobilized antibody. After washing away any unbound substances, an enzyme-linked polyclonal antibody specific for mouse TNF-α is added to the wells. Following a wash to remove any unbound antibody-enzyme reagent, a substrate solution is added to the wells. The enzyme reaction yields a blue product that turns yellow when the Stop Solution is added. The intensity of the color measured is in proportion to the amount of mouse TNF-α bound in the initial step. The sample values are then read off the standard curve.

Mouse C-reactive protein (CRP) levels in serum were determined using a Mouse C-Reactive Protein ELISA Quantitation Kit (Genway; San Diego, Calif.). Briefly, CRP present in serum sample reacts with anti-CRP antibodies which have been adsorbed to the surface of polystyrene microtitre wells. After removal of unbound serum proteins by washing, anti-CRP antibodies conjugated with horseradish peroxidase (HRP), are added. These enzyme-labeled antibodies form complexes with the previously bound serum CRP. Following another washing step, the enzyme bound to the immunosorbent is assayed by the addition of a chromogenic substrate, 3,3',5,5'-tetramethylbenzidine (TMB). The quantity of bound enzyme varies directly with the concentration of CRP in the sample tested; thus, the absorbance, at 450 nm, is a measure of the concentration of CRP in the test sample. The quantity of CRP in the test sample can be interpolated from the standard curve constructed from the standards, and corrected for serum dilution.

Mouse leptin levels in serum were determined using the Quantikine Mouse Leptin Immunoassay (R&D Systems; Minneapolis, Minn.). Briefly, the Quantikine Mouse Leptin Immunoassay employs the quantitative sandwich enzyme immunoassay technique. Microplates are precoated with an affinity purified polyclonal antibody specific for mouse leptin. Standards, controls, and samples are pipetted into the wells and any mouse leptin present is bound by the immobilized antibody. After washing away any unbound substances, an enzyme-linked polyclonal antibody specific for mouse leptin is added to the wells. Following a wash to remove any unbound antibody-enzyme reagent, a substrate solution is added to the wells. The enzyme reaction yields a blue product that turns yellow when the Stop Solution is added. The intensity of the color measured is in proportion to the amount of mouse leptin bound in the initial step. The sample values are then read off the standard curve.

Human $A\beta_{1-40}$ serum levels were determined using the $A\beta_{1-40}$ Colorimetric Immunoassay kit (Invitrogen; Carlsbad, Calif.). Briefly, a monoclonal antibody specific for the $NH_2$ terminus of human amyloid β (Hu Aβ) is pre-coated onto the well of a microtiter strip. During the first incubation, standards of known Hu Aβ content, controls, and unknown samples are pipetted into the wells and co-incubated with a rabbit antibody specific for the COOH-terminus of the 1-40 Aβ sequence. This COOH-terminal sequence is created upon cleavage of the analyzed precursor. Bound rabbit antibody is detected by the use of a horseradish peroxidase-labeled anti-rabbit antibody. After washing, horseradish peroxidase-labeled anti-rabbit antibody (enzyme) is added. After a second incubation and washing to remove all the unbound enzyme, a substrate solution is added, which is acted upon by the bound enzyme to produce color. The intensity of this colored product is directly proportional to the concentration of the Hu Aβ40 present in the original specimen.

1.1(e). Tissue Collection, Processing, Extraction and Immunoassays

At necropsy, the brain was removed and divided along the midline into two halves. One half was frozen on dry ice and the other half was immersion fixed in 10% neutral buffered formalin and processed in paraffin wax.

1.1 (e)(i) Immunochemistry

Brains in paraffin blocks were sagitally sectioned serially (50 μm) across the hippocampus and were immunostained using 4G8 (which recognizes the 17-24-amino acid segment within Aβ) as the primary antibody After washing, a goat anti-mouse secondary antibody was incubated for an additional 30 minutes at room temperature and sections were visualized with avidin-biotin-HRP complex (Vectastain Elite ABC kit, Vector, Burlingame, Calif.) and diaminobenzidine tetrahydrachloride (DAB) in $H_2O_2$. Quantification of Aβ deposition was carried out using a Zeiss Axiocam (Munchen-Hallbergmoss, Germany) and compatible image analysis software, Axiovision (Carl Zeiss Vision GmbH, Munchen-Hallbergmoss, Germany). Each animal was quantified for Aβ deposition. Briefly, using a 5× objective, a single field encompassing the entire hippocampus was manually selected and positive staining was expressed as the percent area stained across the field. The values obtained from all sections per animal were averaged. Sections were analyzed for the number of plaques, the size of plaques, and the amyloid burden, defined as the percentage of the area stained by the antibody.

1.1(e)(ii) Immunoblotting

Frozen brain samples were weighed, minced with a scapel and then transferred to an equal volume of 10% PBS (pH 7.4). Tissues were homogenized using a dounce homogenizer and proteins extracted using the T-PER tissue extraction reagent (Pierce), supplemented with protease/phosphatase inhibitors (Pierce), at a ratio of 1 gram tissue per 10 mL extraction reagent. Samples were briefly centrifuged at 10,000 rpm for 5 minutes and supernatant was transferred to a fresh tube. DNase (Pierce) was added to each sample and incubated at 37° C. for 30 minutes. Total protein was determined with the Coomassie (Bradford) Protein Assay Kit (Pierce) and samples (25 μg) were analyzed by immunoblot. All primary antibodies, except tau-pSer$^{396}$, total tau (all 1:500), and PHF-tau AT8 (1:200), and secondary antibodies were used at final dilutions of 1:10,000, respectively.

1.1(f) Behavioral Assessment

Behavioral testing for established measures of cognitive performance was performed after 4 and 8 weeks of treatment.

1.1(f)(i) Trace Fear Conditioning

The contextual and cued fear conditioning tests measure the ability to remember an unpleasant (conditioned) stimulus and to connect it with a certain environment (context). Contextual fear conditioning is a form of learning that is generally believed to be hippocampus-dependent whereas cued fear conditioning is generally believed to be hippocampus-independent. This protocol is carried out over 2 days.

Day 1—Training: On the first day animals are allowed to habituate in the chamber (Med Associates, Burlington, Vt.) for 2 minutes and are then presented with a white noise (80 dB) for 30 seconds, this stimulus is designated as the conditioned stimulus (CS). After a 2 second interval the animals are administered a 0.5 mA shock; this is designated as the unconditioned stimulus (US). This procedure is repeated 4 times.

Day 2—Contextual/Altered Context/Cued Testing: 24 hours after training, animals are placed back in the original chamber and freezing bouts are scored during 5 minutes to determine the associations of the US with the context (contextual). Freezing is measured automatedly using appropriate software (Med Associates, Burlington Vt.) designed to gather 30 observations in 5 minutes. After contextual freezing is measured, animals are returned to their home cage for 1 hour. The chamber environment is modified (new walls, flooring and odor cues) and the animal is introduced in the "new" chamber for 6 minutes. Freezing rate is quantified as described in the contextual test for 3 minutes in the absence of the CS (altered context). For the remaining 3 minutes the animal is presented with the CS in the altered context and scored for freezing behavior as described previously, to determine the cued fear conditioning score.

1.1(f)(ii) Novel Object Recognition

The novel object recognition test was carried out in a multiple open-field box (20"×20"×17"×4) (San Diego Instruments, San Diego, Calif.). Before training, mice were individually habituated by allowing them to explore the open-field box for 5 minutes on the day prior to testing. During the training session, two identical novel objects were placed into the open-field 16" away from each other and the animals were allowed to explore for 10 minutes. Exploration of the object was considered to be when the head of the animal was facing ½ cm from the object or touching the object. If the animal used the object as a prop to explore the environment, this was not considered an exploration. The time each animal spent exploring each object was recorded. The animals were returned to their home cages immediately after training. One hour after the training the animals were re-introduced into the open-field that contained one novel object and one previously explored object. The objects were of similar exploratory level/physical complexity (i.e., if the old object had a hole, the new one did also) and similar size. During the retention test, animals were introduced into the open-field box and allowed to explore freely for 5 minutes. Time spent and frequency spent with both objects was recorded in addition to rearing and grooming frequency and duration. The open-field box and objects were thoroughly cleaned with 70% ethanol after each session to avoid possible instinctive odorant. A discrimination index (total time spent with new object/total time of object exploration) was used to measure recognition memory.

1.1(g) Statistical Analysis

Statistical data analyses were performed with analysis of variance and Tukey-Kramer multiple comparisons test. Densitometric analyses were performed using the UN-SCAN-IT gel 6.1 software (Silk Scientific; Orem, Utah). $p<0.05$ was considered statistically significant.

Example 1.2

Effect of Leptin Administration on Insulin and Pro-inflammatory Proteins

The first set of studies examined the levels of leptin detectable in the serum of TgCRND8 mice. FIG. 1 shows bar graphs of serum concentrations (ng/ml) of leptin, insulin and CRP in CRND8 and wt mice assessed in serum from leptin- or saline-treated CRND8 or wt mice by ELISA. Leptin-treated transgenic animals showed significantly ($p<0.05$) elevated levels of leptin (FIG. 1A; left, light gray bar) compared to saline-treated animals (left, dark gray bar). The levels detectable in the saline-treated TgCRND8 were compatible to wild-type (wt) littermates (right bar). There was no significant difference in insulin levels observed in leptin- or saline-treated mice (FIG. 1B).

C-reactive protein (CRP), a protein whose levels rise dramatically during inflammatory processes occurring in the body, served as a biomarker for inflammation. There was no detectable difference in CRP levels observed in Leptin- or saline-treated animals (FIG. 1C). These results were similar to findings with other inflammatory proteins, specifically TNFα and cortisol (data not shown) which did not change in response to Leptin treatment.

Example 1.3

Pathways Regulated by Leptin Administration in Brain

It generally is believed that the post-receptor binding of Leptin triggers the JAK/STAT pathway to induce gene transcriptional changes via activation of Janus tyrosine kinase 2 (JAK2), the signal transducer and activator 3 (STAT3), and the suppressor of cytokine signaling 3 (SOC3) in central and peripheral tissues. The levels of Leptin in the brains of Leptin-treated and saline-treated mice were investigated and the putative downstream effectors of Leptin, specifically SOCS3 and peroxisome proliferator-activated receptor-γ (PPARγ), were examined to determine whether they increased.

Figure 2:
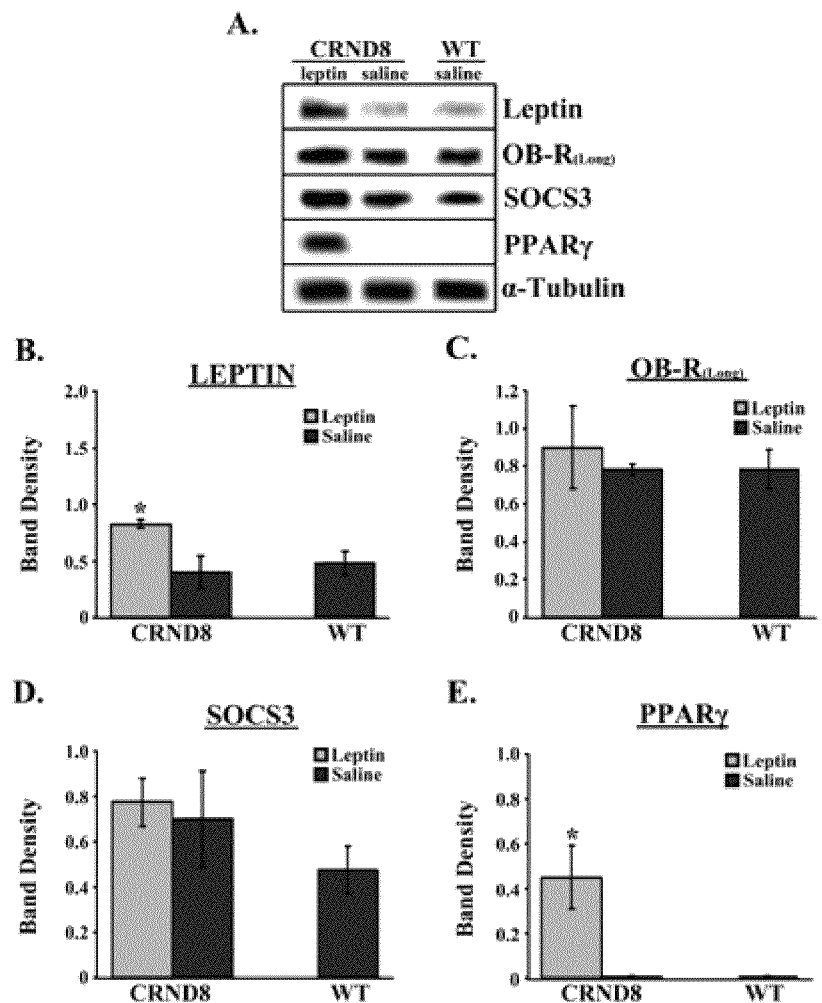
FIG. 2 shows expression of Leptin, Leptin receptor (OB-R) and downstream signaling targets in CRND8 and wt mouse brains. A. Brains from Leptin- or saline-treated CRND8 or wt mice were harvested, and expression of (B) Leptin, (C) Leptin receptor and (D, E) downstream signaling targets (SOCS3, PPARγ) were determined by immunoblot.

FIG. 2 shows an immunoblot showing leptin, OB-R(long), SOCS3, PPARγ and α-tubulin from brains from leptin-treated or saline-treated CRND8 or wild-type (wt) mice. Membranes were stripped and re-probed with α-tubulin antibody for normalization. Representative blots are shown (n=3). Normalized bands were analyzed by densitometry and are presented as the mean density±SD. * vs. like saline-treated. The Leptin levels were significantly (p<0.05) higher in the brains of Leptin-treated animals compared to saline-treated (FIG. 2A, top row; FIG. 2B, light gray bar). There was no significant change in expression of the long isoform of the Leptin receptor (OB-R) in Leptin-treated brains compared to control (FIG. 2A, second row; FIG. 2C). There was a non-significant increase (p>0.05) (FIG. 2D) in expression of SOCS3 in Leptin-treated TgCRND8 animals (FIG. 2A, third row).

PPARγ, a transcription factor known to regulate β-secretase (BACE), is a key enzyme in amyloid precursor protein (APP) processing and generally is believed to be involved in modulating Leptin's action. Leptin-treated transgenic animals displayed a significant (p<0.05) increase in PPARγ levels compared to control (FIG. 2A, fourth row; FIG. 2E, light gray bar).

Example 1.4

Aβ Levels and Plaque Deposition in Leptin-Treated TgCRND8 Mice

The extracellular accumulation of Aβ in the form of plaques is a hallmark pathological feature of AD and the amount deposited depends on the rates of its production, secretion, aggregation and clearance.

TgCRND8 mice overexpress the human APP gene containing the Swedish (K670N and M671L) and the Indiana (V717F) familial AD (FAD) mutations. The aforementioned Leptin treatments were initiated at 10 months of age, when typically the levels of total brain Aβ start rising and were completed by 12 months of age, just when the first Aβ deposits make appearance in the Tg2576 mice. In these studies with the TgCRND8 mice, the entire treatment (4 months to 6 months of age) was performed during the post-plaque period which starts around 3 months of age.

Figure 3:
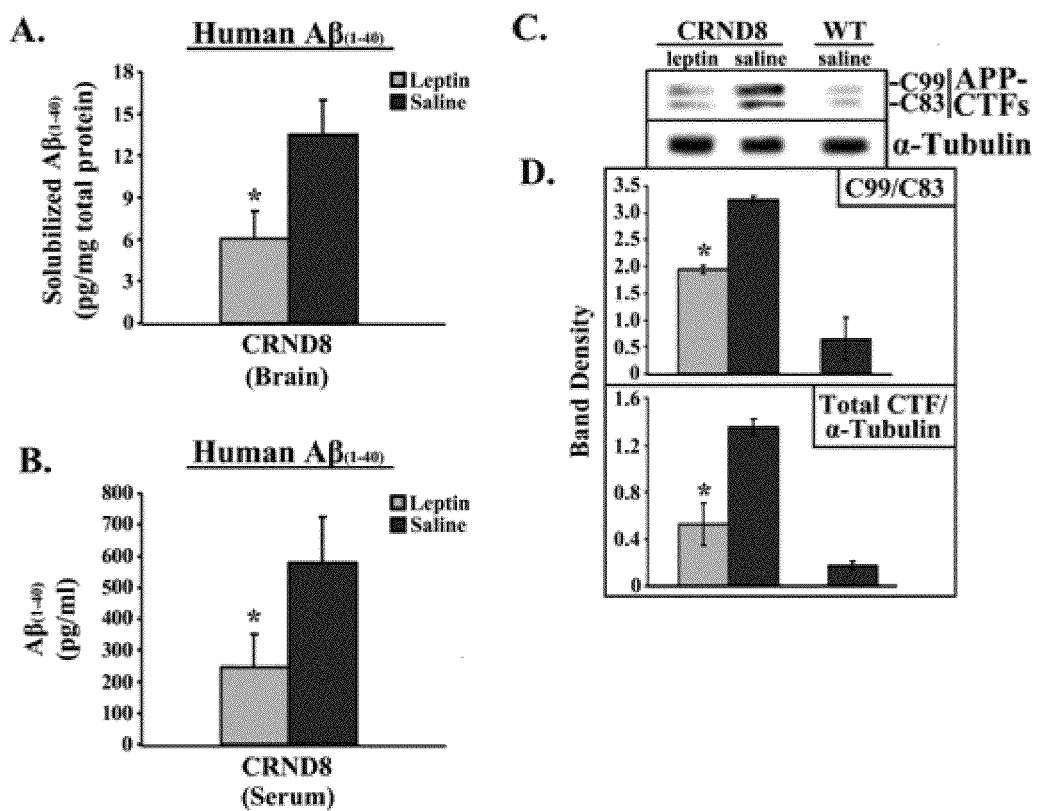
FIG. 3 shows expression of APP C-terminal fragments (CTFs) and soluble $A\beta_{1-40}$ in CRND8 and wt mice. A. Brains from Leptin- or saline-treated CRND8 or wt mice were harvested, and expression of APP CTFs (C99, C83) was determined by immunoblot. B. Normalized bands (ratios of C99/C83 and total CTFs/α-tubulin) were analyzed by densitometry and are presented as the mean density±SD. C. Levels of soluble $A\beta_{1-40}$ present in the brains or (D) serum of Leptin- or saline-treated CRND8 or wt mice were determined by ELISA.

FIG. 3 shows expression of APP C-terminal fragments (CTFs) and soluble $A\beta_{1-40}$ in CRND8 and wt mice. In (A) brains from Leptin- or saline-treated CRND8 or wt mice were harvested, and expression of APP CTFs (C99, C83) was determined by immunoblot. Membranes were stripped and re-probed with α-tubulin antibody for normalization. Representative blots are shown, n=3. In (B), normalized bands (ratios of C99/C83 and total CTFs/α-tubulin) were analyzed by densitometry and are presented as the mean density±SD. In (C), levels of soluble $A\beta_{1-40}$ present in the brains or in (D) serum of Leptin- or saline-treated CRND8 or wt mice, were determined by ELISA. Levels of soluble brain $A\beta_{1-40}$ were normalized to the total amount of soluble brain protein. Results are presented as the mean concentration (brain—µg/mg total protein, n=5; serum—pg/ml, n=10)±SD. * vs. saline-treated TgCRND8 cells. A significant (p<0.05) reduction in $A\beta_{1-40}$ levels in both brain (FIG. 3A, gray bar) and serum (FIG. 3B, gray bar) of the Leptin-treated TgCRND8 mice was found.

Leptin treatment was studied to determine whether the leptin treatment altered the processing of brain APP into the C99 C-terminal fragment (CTF) of APP, derived by the action of BACE and which is a direct precursor of Aβ (FIG. 3C), or the C83 CTF of APP, which is a non-amyloidogenic product derived by the action of α-secretase. A significant (p<0.05) reduction in the ratio of C99 fragment to the C83 species (FIG. 3D, top panel) and total CTFs (bottom panel) was observed in Leptin-treated animals versus saline-treated controls. This is consistent with Leptin's involvement in modulating BACE activity.

Figure 4:
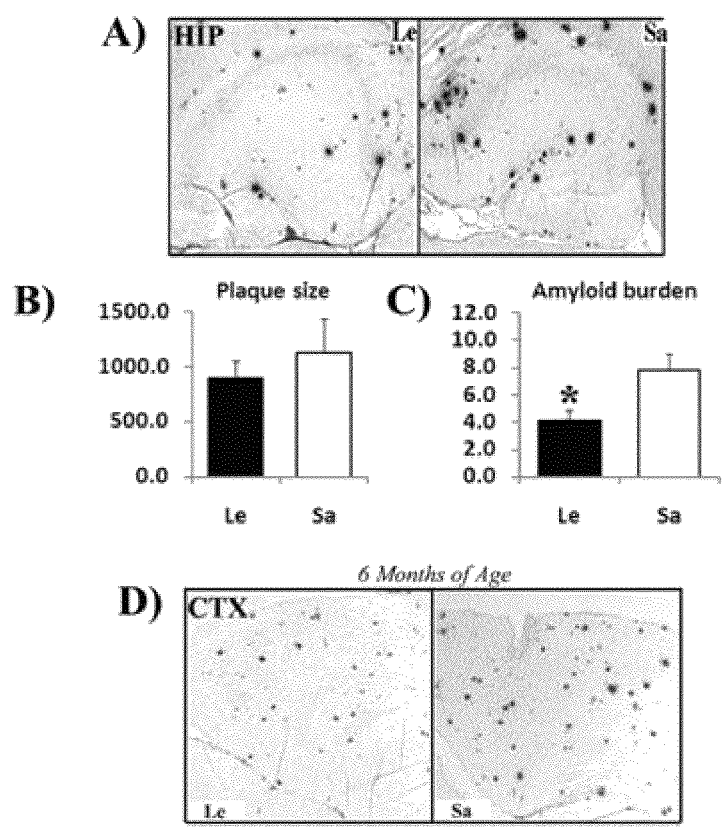
FIG. 4 shows amyloid plaque deposition in Leptin-treated TgCRND8 mice. A. Brain slices were stained with the 4G8 antibody in the hippocampal region; Le—transgenic animals treated with Leptin; Sa—transgenic animals treated with Saline. B. Bars represent average size of plaque (μmm$^2$) ±S.E.M. or (C) % area stained in the region±S.E.M.; n=8-9 per bar. D. Cortical region stained with 4G8 antibody.

FIG. 4 shows amyloid plaque deposition in Leptin-treated TgCRND8 mice. In A, brain slices were stained with the 4G8 antibody in the hippocampal region; Le—transgenic animals treated with Leptin; Sa—transgenic animals treated with Saline. In B, bars represent average size of plaque (µmm$^2$) ±S.E.M. or in (C) % area stained in the region±S.E.M.; n=8-9 per bar. D. Cortical region stained with 4G8 antibody.

Immunohistochemical examination of paraffin-imbedded brain sections (FIG. 4) revealed that 8 weeks of Leptin treatment significantly (p<0.05) reduced the amyloid burden in the hippocampus (FIG. 4A) of 6-month old TgCRND8 mice, compared to age and gender matched saline-treated transgenic mice. This is a region particularly enriched in functional (OB-Rb) Leptin receptors. The significantly decreased amyloid burden in the hippocampus (quantified as % area stained with 4G8 antibody) was parallel to a decrease in the average size of plaques (FIGS. 4B and 4C); there was an insignificant change in the overall number of plaques in that region (data not shown). Examination of other brain regions, such as the cortex (FIG. 4D), suggested a similar pattern of staining.

Example 1.5

Leptin-Treated Transgenic Animals Show Reduced Tau Phosphorylation

Neurofibrillary tangles (NFT) are intra-neuronal aggregates of highly phosphorylated tau protein that correlate closely with cognitive loss in AD. It generally is believed that the abnormal phosphorylation of tau protein leads to disrupted microtubule function, abnormal protein trafficking, the formation of NFTs and eventual neuronal death.

Figure 5:
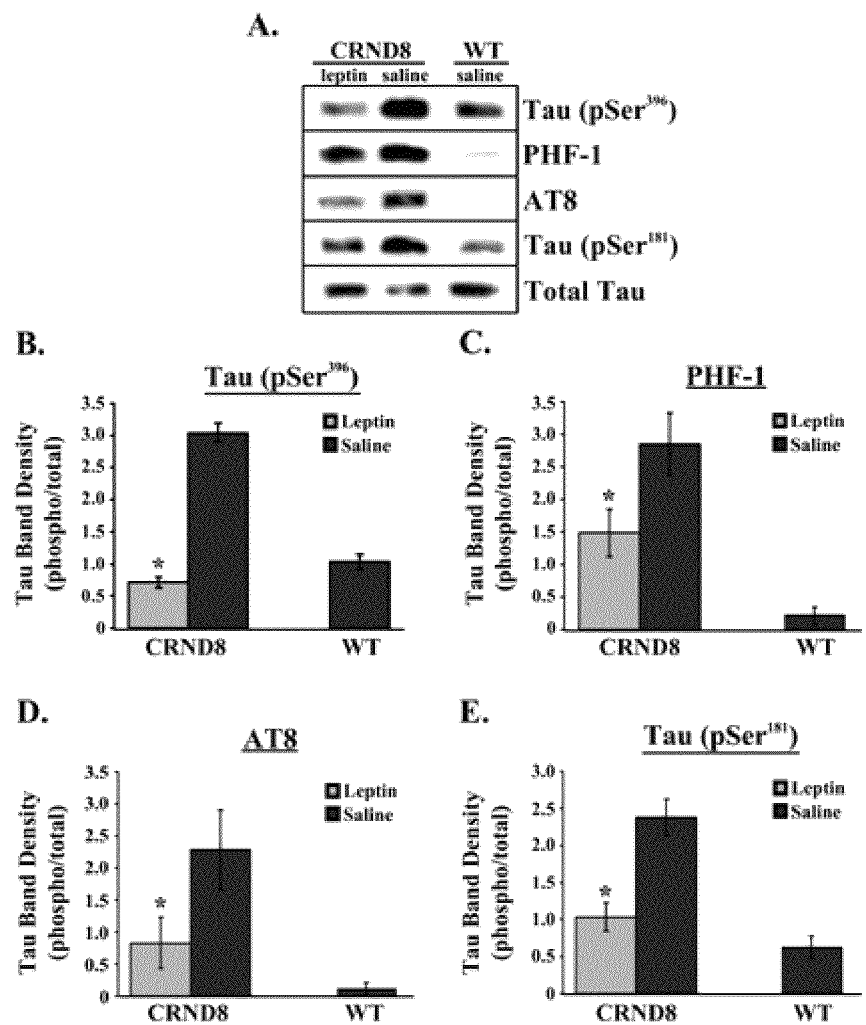
FIG. 5 shows AD-related tau phosphorylation in TgCRND8 and wt mouse brain. A. Brains from Leptin- or saline-treated CRND8 or wt mice were harvested, and tau phosphorylation at (B) Ser$^{396}$, (C) PHF-1 (Ser$^{396/404}$), (D) AT8 (Ser$^{202/204}$) and (E) Ser$^{181}$ were determined by immunoblot.

TgCRND8 or Tg2576 mice do not develop NFTs; some studies have reported increased brain tau phosphorylation in Tg2576 mice. The phospho-tau levels in the brains of Leptin-treated or saline-treated transgenic or wild-type (wt) mice were assessed . FIG. 5 shows AD-related tau phosphorylation in TgCRND8 and wt mouse brain. In A, brains from Leptin- or saline-treated CRND8 or wt mice were harvested, and tau phosphorylation at (B) Ser$^{396}$, (C) PHF-1 (Ser$^{396/404}$), (D) AT8 (Ser$^{202/204}$) and (E) Ser$^{181}$ were determined by immunoblot. Membranes were stripped and re-probed with total tau antibody for normalization. Representative blots are shown, n=3. Normalized bands were analyzed by densitometry and are presented as the mean density±SD. * vs. saline-treated CRND8 mice.

The saline-treated, transgenic mice expressed relatively high levels of phospho-tau at all epitopes examined (FIG. 5A; FIGS. 5B-5E, left dark gray bars). Leptin-treatment significantly (p<0.05) reduced phospho-tau (left light gray bars) at each AD-relevant epitope to levels observed in the brains of wt animals (right bars). These results show that tau is hyperphosphorylated in TgCRND8 mice.

Example 1.6

Behavioral Improvements of TgCRND8 Mice Treated With Leptin 1.6(i) Novel Object Recognition Animals of the three groups: a) TgCRND8 treated with Leptin, b) TgCRND8 treated with saline and c) wild-type treated with saline, were tested in the Novel object recognition test after 4 and 8 weeks treatment duration.

Figure 6:
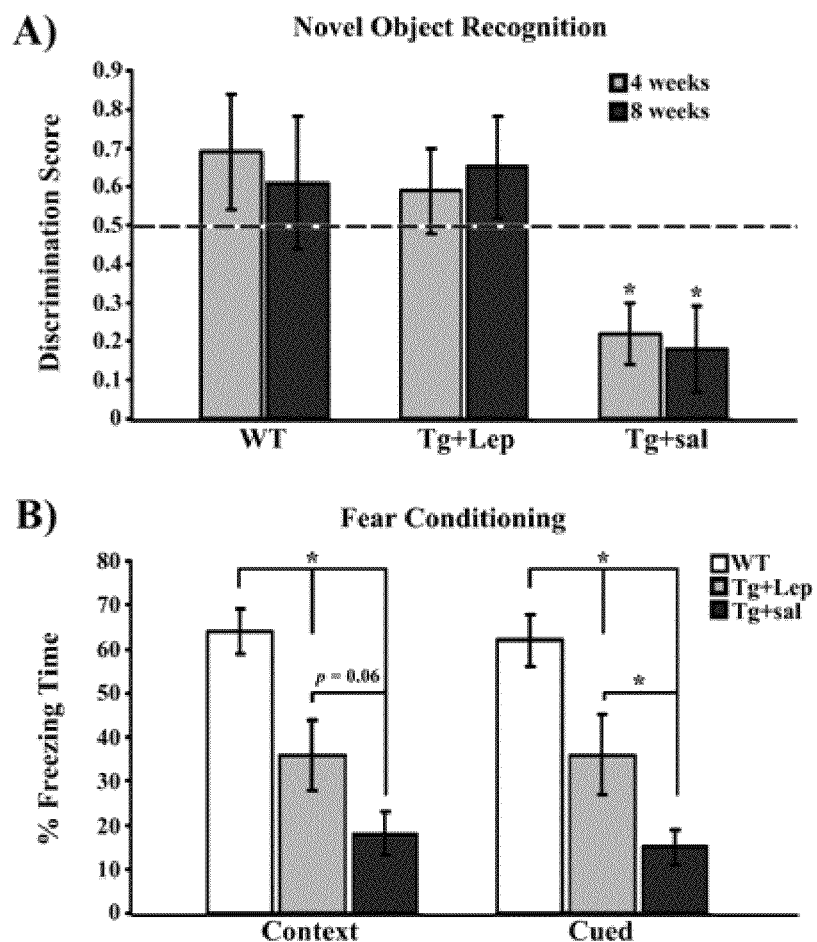
FIG. 6 shows cognitive assessment of CRND8 and wt mice. A. object recognition test, B. fear conditioning test. Context: *p=0.009 for WT vs Tg+Lep; *p=0.0001 for WT vs Tg+Sal; Cued: *p=0.012 for WT vs Tg+Lep; *p=0.0001 for WT vs Tg+Sal; *p=0.04 for Tg+Lep vs Tg+sal.

FIG. 6 shows cognitive assessment of CRND8 and wt mice. In the novel object recognition test (A), working memory was scored in wt and 4- or 8-week, Leptin- or saline-treated transgenic mice as time spent exploring familiar versus novel objects. The dotted line indicates animals remembering (more than ½ of the total time spent between the two objects is with the new object); anything below the line shows memory impairment. *p=0.01 for Tg-Lep vs Tg-saline; *p=0.003 for Tg-sal vs WT. In the fear conditioning test (B), aversive learning tasks were used to measure fear response to an unpleasant stimulus in wt and Leptin- or saline-treated transgenic mice. Freezing was quantified in the original chamber before and after several training sessions (mild footshocks) for contextual fear conditioning or in a novel environment containing an auditory cue that was previously paired with a footshock. Context: *p=0.009 for WT vs Tg+Lep; *p=0.0001 for WT vs Tg+Sal; Cued: *p=0.012 for WT vs Tg+Lep; *p=0.0001 for WT vs Tg+Sal; *p=0.04 for Tg+Lep vs Tg+sal.

Leptin-treated TgCRND8 and wild-type mice spent statistically (p<0.05) more time with the novel object compared to the transgenic treated with saline (FIG. 6A). This indicated that there was an improvement in working memory performance of the TgCRND8 mice after 4-8 weeks of Leptin treatment, compared to saline treated TgCRND8. Leptin-treated transgenic animals were indistinguishable from the wild-type mice in this test, while saline-treated TgCRND8 mice performed very poorly (FIG. 6A) compared to both other groups. Thus, 1-2 month chronic Leptin treatment abrogates impaired performance in this cognitive task in the 6-month old TgCRND8 mice.

1.6(ii) Fear Conditioning (FC)

In this test, an aversive training chamber was used for training and measurement of contextual and cued fear associated memory after repeated pairings of CS (auditory cue) and US (mild footshock). Animals were placed in the original chamber 24 hours after training to test contextual fear conditioning or in a novel environment in the presence of the CS to test for cued fear conditioning. As shown in FIG. 6B, where the x-axis represents % freezing time, TgCRND8 mice performed better in the contexual fear conditioning test after 8 weeks of Leptin treatment as compared to saline-treated animals. This finding approached statistical significance (p<0.06). Additionally, Leptin treatment resulted in a statistically significant (p<0.05) improvement in performance in the cued fear conditioning. There was no statistical significance when tested in the altered context and low freezing response (data not shown), indicating that the animals did not recognize the altered context.

1.7. Summary:

The results demonstrate the effects of chronic Leptin-treatment on AD-like pathobiology and cognitive decline using a transgenic CRND8 mouse model system when compared to saline controls. Leptin-treated animals were found to have reduced levels of $A\beta_{1-40}$ in both brain and serum. In the brain, a reduction in the processing of APP through the amyloidogenic pathway was observed. Further, Leptin-treated animals showed a significant decrease in amyloid burden in the hippocampus, which was associated with a decrease in the average size (but not number) of 4G8-stained amyloid plaques (FIG. 4). Cortical areas were less affected by the treatment, despite the significant drop in the amount of total solubilized $A\beta_{1-40}$ in brain extracts (52% reduction in detergent-extractable $A\beta_{1-40}$ after 8 weeks of Leptin treatment).

Leptin did not significantly alter the levels of CRP (FIG. 1C), TNFα or cortisol (data not shown) compared to saline treatment.

It generally is believed that Leptin forms a feedback loop with SOCS3, a negative cytokine regulator that inhibits Jak2/STAT3 signaling following prolonged receptor (OB-R) activation. Overactivation of SOCS3 signaling could lead to prolonged repression of inflammatory pathways and thus increase the risk for immunosuppression. Leptin-treated TgCRND8 and wt animals did not show elevated SOC3 expression (FIG. 2D), suggesting that chronic administration of Leptin is unlikely to lead to immune defects.

PPARγ is a downstream target of Leptin signaling. Leptin-treated transgenic mice displayed a large increase in PPARγ expression (FIG. 2E). Leptin-treated TgCRND8 mice displayed reduced levels of the amyloidogenic C99 APP fragment and $A\beta_{1-40}$ levels in both brain and serum (FIG. 3).

Leptin treatment of TgCRND8 mice significantly reduced the levels of phospho-tau at all examined epitopes (FIG. 5). It generally is believed that induction of hyperphosphorylation of tau but not tau oligomerization is common in transgenic mice expressing APP.

Leptin-treated TgCRND8 mice showed improved cognitive performance in novel object recognition and fear conditioning tests compared to saline-treated littermates (FIG. 6). A reduced amyloid load was found within the hippocampus of Leptin-treated transgenic mice (FIG. 4A).

The present disclosure demonstrates Leptin's (i) ability to ameliorate AD-like pathological pathways; and (ii) efficacy for reverting or preventing the cognitive deterioration of the TgCRND8 mouse. Leptin treatment was not associated with inflammation.

Example 2

2.1. Materials and Methods 2.1(a). Media

Minimum essential medium (MEM) was purchased from ATCC (Manassas, Va.). Neurobasal medium, B27 supplement and L-glutamine were purchased from Gibco (Carlsbad, Calif.). Trypsin-EDTA and penicillin solution were purchased from MP Biomedicals (Solon, Ohio). Fetal bovine serum (FBS), all-trans retinoic acid (RA) and human recombinant leptin were purchased from Sigma-Aldrich (St. Louis, Mo.). 5-Aminoimidazole-4-carboxyamide ribonucleoside (AICAR) was purchased from Cell Signaling Technology (Danvers, Mass.). Myristolated-AIP (Myr-AIP) (CaM kinase II inhibitor—1 μM) was purchased from Biomol International (Plymouth Meeting, Pa.). Compound C (AMPK inhibitor—1 μM), D-erythro-Sphingosine, N-Acetyl-($C_2$ ceramide) (PP2A activator—1 μM), lithium choloride (LiCl) (GSK-3β inhibitor—10 mM), $N^4$-(6-Aminopyrimidin-4-yl)-sulfanilamide, HCl (N6A4S) (CDK5 inhibitor—2 μM), furanyl-nitroaminoguanidine (FNG) (ERK inhibitor—20 μM), Anthra[1,9-co]pyrazol-6(2H)-one 1,9-pyrazoloanthrone (SP600125) (JNK inhibitor—100 nM), KT5720 (PKA inhibitor—100 nM), 2-Hydroxy-4-(((4-methylphenyl)sulfonyloxy)acetyl)amino)-benzoic acid (S3I-201) (STAT3 inhibitor—100 µM), 5-(2,2-Difluoro-benzo[1,3]dioxo1-5-ylmethylene)-thiazolidine-2,4-dione (522 DB13D) (PI3K inhibitor—20 µM), 1L6-Hydroxymethyl-chiro-inosito1-2-(R)-2-0-methyl-3-O-octadecyl-sn-glycerocarbonate (1L6HCI) (Akt inhibitor—5 µM), 2-(4-Chlorophenyl)-4-(4-fluorophenyl)-5-pyridin-4-yl-1,2-dihydropyrazol-3-one (24C44F5P) (p38 MAP kinase inhibitor—100 nM) and H-Trp-Glu-OH (G3335) (PPARγ antagonist—30 µM) were purchased from EMD Chemicals (Gibbstown, N.J.). The final concentrations and incubation times used for all inhibitors or activators were based on previous reports (see, for example, Ishida, A., and Fujisawa, H. (1995) J. Biol. Chem., 270:2163-2170; Zhou, G., et al. (2001) J. Clin. Invest., 108:1167-1174; Ballou, L., et al (1992) J. Biol. Chem., 267:20044-20050; Klein, P. S., and Melton, D. A. (1996) Proc. Natl. Acad. Sci. USA, 93:8455-8459; Clare, P., et al. (2001) J. Biol. Chem., 276:48292-48299; Chen, F., et al. (2006) Bioorg. Med. Chem. Lett., 16:6281-6287; Han, Z., et al. (2001) J. Clin. Invest., 108:73-81; Kase, H., et al. (1987) Biochem. Biophys. Res. Commun., 142:436-440; Siddiquee, K., et al. (2007) Proc. Natl. Acad. Sci. USA, 104:7391-7396; Bilancio, A., et al. (2006) Blood, 107:642-650; Hu, Y., et al. (2000) J. Med. Chem., 43:3045-3051; de Laszlo, S. E., et al., (1998) Bioorg. Med. Chem. Lett., 8:2689-2694; Ye, F., et al., (2006), Chembiocem., 7:74-82). The content of each of these references is incorporated herein by reference.

2.1(b). Antibodies

Rabbit anti-Akt (pSer$^{473}$), -Jak2 pTyr$^{1007/1008}$, -AMPKα (pThr$^{172}$), GSK-3β (pSer$^9$), —CaMKII (pThr$^{286}$), —PKA (pThr$^{197}$), —PPARγ (81B8), p38 MAPK (pThr$^{180}$/Tyr$^{182}$) (28B10) mAb, tau (pSer$^{396}$) mAb and tau (tau46) mAb were purchased from Cell Signaling. PHF-tau mAb (clone AT8) was purchased from Pierce Biotechnology (Rockford, Ill.). PHF-1 mAb was a gift from Dr. Peter Davies, Albert Einstein College of Medicine (Bronx, N.Y.). Anti-Alzheimer Precursor Protein (APP) 643-695 mAb was purchased from Millipore (Billerica, Mass.). Rabbit anti-tau (pThr$^{181}$) was purchased from Sigma-Aldrich. Rabbit anti-α-tubulin mAb was purchased from Affinity BioReagents (Golden, Colo.).

2.1(c). Culture and Neuronal Induction of Cell Lines

Human neuroblastoma, SH-SY5Y and IMR-32, cell lines were purchased from ATCC. Cell culture was performed according to manufacturer's specific guidelines. Briefly, cells were propagated in MEM containing 10% FBS until 80-90% confluence, then detached from the flask by trypsin-EDTA and sub-cultured at a ratio of 1:5.

For neuronal differentiation, 1×10$^6$ SY5Y or IMR-32 cells were grown in neuronal induction medium (NIM), which consisted of MEM containing 2% FBS supplemented with 10 µM RA. Cells were incubated in NIM for 6 days, and switched to serum-free NIM prior to treatment and harvesting on day 7.

2.1(d). Culture of Rat Primary Neurons

Primary rat cortical neurons were purchased from BrainBits LLC (Sprinfield, Ill.), and cultured as per manufacturer's instructions. Briefly, tissues were dispersed and supernatant was transferred to a new tube and centrifuged for 1 minute at 1100 rpm. Neurons were then seeded in Ewell plates coated with poly-D-lysine (BD Biosciences; San Jose, Calif.) and grown in Neurobasal medium supplemented with B27 and 0.5 mM L-glutamine. Medium was changed after 4 days, and at 7 days in culture the neurons were treated as described below and harvested.

2.1(d). Protein Extraction and Immunoblotting

Neuronal cells were treated with leptin (1600 ng/ml) for 4 hours or AICAR (2 mM) or specific inhibitors for 1 hour, unless otherwise specified, and then harvested by scraping. Cell pellets were resuspended in protease and phosphatase inhibitor-supplemented 1× radioimmunoprecipitation assay (RIPA) lysis/extraction buffer (Pierce), and then subjected to freeze/thaw cycles in a dry ice/ethanol bath. Total protein was determined with the Coomassie (Bradford) Protein Assay Kit (Pierce). Whole cell extracts (25 µg) were analyzed by immunoblot using 10% or 4-20% tris-glycine SDS-PAGE pre-cast gels (Lonza; Rockland, Me.), and the proteins were transferred onto polyvinylidene difluoride membranes (Millipore). Membranes were incubated overnight at 4° C. with primary antibodies and then detected the following day with HRP-conjugated secondary IgG. All primary antibodies, except tau-pSer$^{396}$, total tau, APP (all 1:500) and PHF-tau AT8 (1:200), and secondary antibodies were used at final dilutions of 1:1,000 and 1:10,000, respectively. HRP was developed with SuperSignal West Pico Chemiluminescent Substrate (Pierce), and imaged using a BioRad (Hercules, Calif.) ChemiDoc XRS System. The membranes were stripped with Restore PLUS Western Blot Stripping Buffer (Pierce) for reprobing with other antibodies.

2.1(e). GSK-3β Overexpression and Knockdown

For knockdown of glycogen synthase kinase-3β (GSK-3 (3), differentiated SY5Y were transiently tranfected with 50 nM SignalSilence GSK-3β siRNA (Cell Signaling) for 48 hours using the TransIT-TKO transfection reagent (Mirus; Madison, Wis.). Briefly, approximately 24 hours prior to transfection, cells are plated at an appropriate cell density to obtain about 60-80% confluence the following day (3×10$^4$ to 1.2×10$^5$ cells per well of a 24-well plate, depending on cell size and characteristics). The adherent cells are plated in 500 µl of complete growth media per well, and incubated overnight. Alternately, for cells in suspension, immediately prior to transfection, cells are plated in 0.25 ml of complete growth media per well, at an appropriate density to obtain about 60-80% confluence at time of transfection (3–5×10$^5$ cells per well). Alternatively, cells may be plated the day prior to transfection to obtain about 60-80% confluence at the time of transfection (1.5–2.5×105 cells per well). In a sterile, plastic tube, 50 µl of serum-free medium is added. TransIT-TKO Transfection Reagent then is directly added (1-4 µl per well) into the serum-free media, the suspension mixed throughly by pipetting or vortexing, and incubated at room temperature for 5 to 20 minutes. The siRNA (at a concentration such that the final concentration in the well is about 25 nM) is added to the diluted TransIT-TKO Reagent, mixed gently by pipetting, then incubated at room temperature for 5 to 20 minutes. For adherent cell types, the volume in the well is adjusted to 250 µl of complete growth media by removing about 250 µl (half) of the original plating media. The TranIT-TKO Reagent/siRNA complex mixture is added dropwise to the cells. The complexes are evenly distributed to the dish by gently rocking the dish back and forth and from side to side (no swirling), then incubated for 24 to 72 hours. The cells then are assayed for knockdown of target gene expression. Cells transfected with 50 nM SignalSilence Control siRNA (fluorescein conjugate) (Cell Signaling), were used as a negative control and for measuring transfection efficiency.

For GSK-3β overexpression, differentiated SY5Y were transiently transfected with 2 µg of expression vector (pCMV6-XL4) containing the GSK-3β full-length cDNA sequence (Accession No: NM 002093.2) (OriGene; Rockville, Md.) for 48 hours using the TurboFectin 8.0 transfection reagent (OriGene), according to manufacturer's specific instructions. Briefly, the transfection reagent is added to the cell media prior to exposure to the expression vector. Cells transfected with 2 µg empty pCMV6-XL4 (OriGene) served as a negative control.

Following transfection, cells were harvested and knockdown or overexpression of GSK3β was confirmed by immunoblot.

2.1(f). GSK-3β and β-Amyloid$_{(1-40)}$ Quantification

GSK-3β levels in cellular extracts and Aβ$_{(1-40)}$ levels in cell culture media were determined using the PhosphoDetect GSK-3β (pSer$^9$) ELISA kit (EMD Chemicals) and the Human β-Amyloid 1-40 Colorimetric Immunoassay kit (Invitrogen; Carlsbad, Calif.), respectively, according to manufacturer's specific instructions. GSK-3β and Aβ$_{(1-40)}$ levels were calculated from a standard curve developed with OD at 450 nm versus 8 serial dilutions of known concentration.

2.1(g). Statistical Analysis

Statistical data analyses were performed with analysis of variance and Tukey-Kramer multiple comparisons test. Densitometric analyses were performed using the UN-SCAN-IT gel 6.1 software (Silk Scientific; Orem, Utah). $p<0.05$ was considered statistically significant.

Example 2.2

Regulation of Tau Phosphorylation in Differentiated SY5Y

Studies have shown that Tau phosphorylation at AD-related sites in human neuroblastoma SY5Y cells increases with RA-induced differentiation (RA-SY5Y). These changes have been attributed to an increase in the absolute levels of tau during differentiation, rather than hyperphosphorylation of the protein. Due to this increased basal expression, RA-SY5Y cells represent a convenient culture system to monitor changes in human tau phosphorylation.

Kinases implicated in directly phosphorylating tau (FIG. 7 and Table 1) were studied. Specific corresponding kinase inhibitors were used to treat cells for 1 hour (described above in 2.1, *Materials and Methods*), and the effect on tau phosphorylation at AD-related sites was measured. For comparison, cells were treated for 1 hour with C2 ceramide, a protein phosphatase 2A (PP2A) activator, which did not affect significantly the levels of phospho-tau (FIG. 7 and Table 1).

Figure 7:
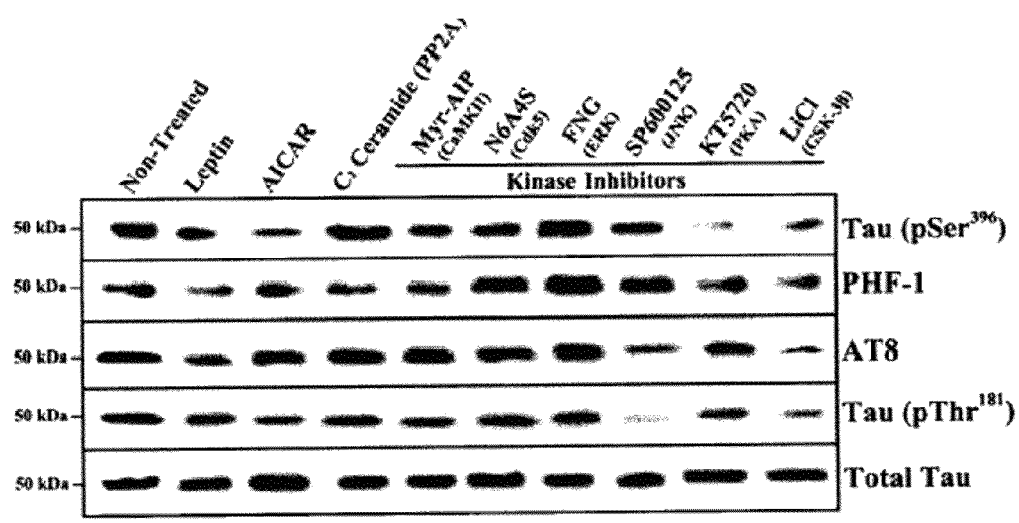
FIG. 7 shows enzymatic regulation of tau phosphorylation in RA-SY5Y.

FIG. 7 shows enzymatic regulation of tau phosphorylation in RA-SY5Y. RA-SY5Y were incubated with the PP2A activator, C2 ceramide, or different kinase inhibitors for 1 hour, or non-treated (vehicle), and phosphorylation of tau at multiple sites was measured. Treatment with leptin (1600 ng/ml) or AICAR (2 mM) served as positive control. Whole-cell lysates were prepared and analyzed by immunoblot with phosphorylated tau-specific antibodies (pSer396, PHF-1, AT8 or pSer181). Membranes were stripped and re-probed with total tau antibody for normalization. Representative blots are shown (n=3). Semi-quantitative band density analyses are presented in Table 1. Normalized bands from FIG. 7 were analyzed by densitometry and results are presented in Table 1 as the mean±SD percent fold change, relative to vehicle, which were arbitrarily assigned a value of 0; vs. vehicle.

The results showed that inhibition of calcium/calmodulindependent protein kinase II (CaMKII) (Myr-AIP), protein kinase A (PKA) (KT5720) or GSK-3β (LiC1) produced the most significant ($p<0.05$) reduction of tau phosphorylation at multiple sites compared to controls (vehicle-treated cells) (FIG. 7 and Table 1). Treatments with leptin (1600 ng/ml for 4 hours) or AICAR (2 mM for 1 hour reduced tau phosphorylation, and thus were included as positive controls.

Figure 14:
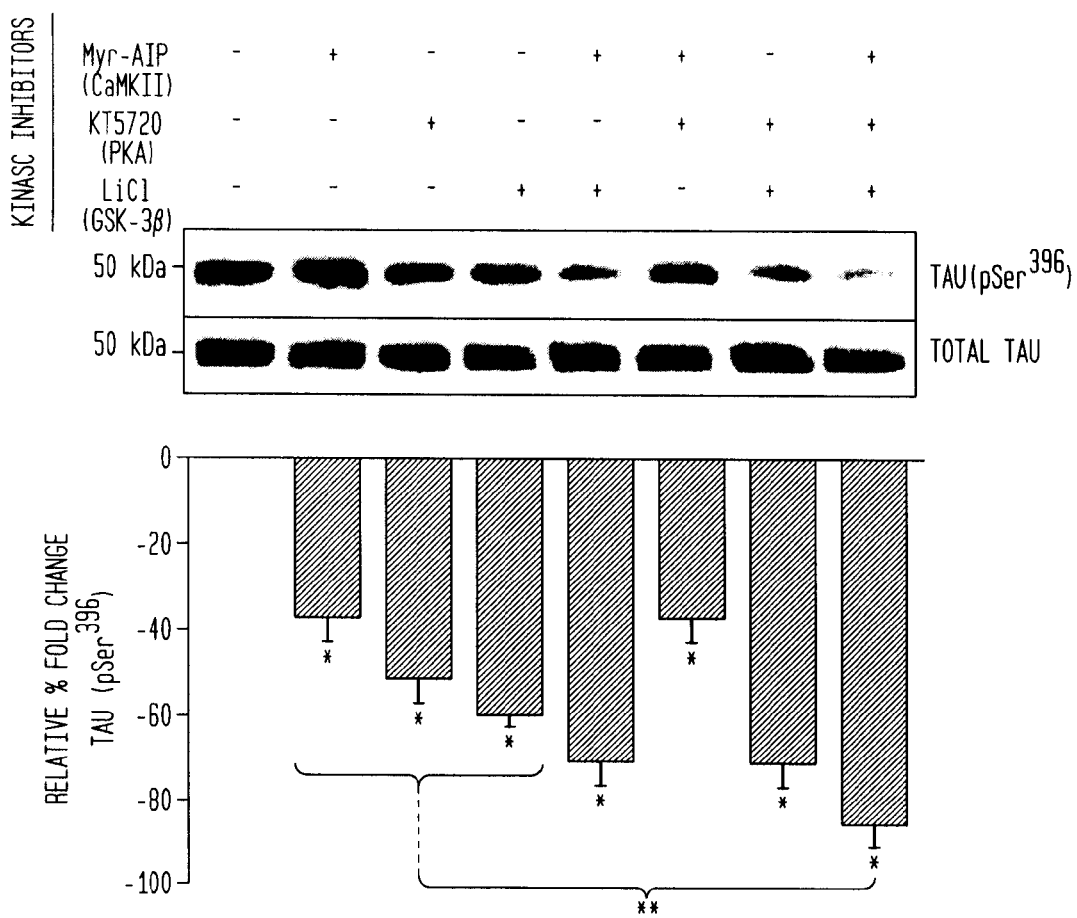
FIG. 14 shows decreased phosphorylation of tau by multiple kinase inhibition. RASY5Y cells were incubated with CaMKII, PKA or GSK-3P inhibitors alone or in various combinations for 1 hr, or non-treated (vehicle), and phosphorylation of tau was measured. Whole-cell lysates were prepared and analyzed by immunoblot with a phosphorylated tau-specific antibody (pSer396). * vs. non-treated (vehicle); ** vs. treatment with any individual kinase inhibitor

FIG. 14 shows decreased phosphorylation of tau by multiple kinase inhibition. RASY5Y were incubated with CaMKII, PKA or GSK-3P inhibitors alone or in various combinations for 1 hr, or non-treated (vehicle), and phosphorylation of tau was measured. Whole-cell lysates were prepared and analyzed by immunoblot with a phosphorylated tau-specific antibody (pSer396). Membranes were stripped and re-probed with total tau antibody for normalization. Representative blots are shown, n=3. Normalized bands were analyzed by densitometry and results are presented as the mean±SD percent fold change, relative to non-treated samples, which were arbitrarily assigned a value of 0; * vs. non-treated (vehicle); ** vs. treatment with any individual kinase inhibitor. FIG. 14 shows that Combined inhibition utilizing CaMKII-, PKA- and GSK-3β-specific inhibitors produced a synergistic effect in reducing tau phosphorylation compared to either inhibitor alone.

These data indicate that tau is the substrate for a number of kinases.

The effect of Leptin and/or AICAR on the phosphorylation status of any of these kinases was studied. Typically, phosphorylation of these kinases results in refolding, and this triggers a change in activity. FIG. 8 shows the effects of leptin and AICAR on tau-specific kinase activation in RA-SY5Y. RA-SY5Y were treated with leptin (1600 ng/ml), AICAR (2 mM) or non-treated (vehicle), and phosphorlyation of (A) CaMKII (pThr286), (B) PKA (pThr197) and (C) GSK-3β (pSer9) were measured by immunoblot. Membranes were stripped and re-probed with (A,B) α-tubulin or (C) total GSK-3β for normalization. Representative blots are shown, n=3. Normalized bands were analyzed by densitometry and results are presented as the mean±SD percent fold change, relative to non-treated samples, which were arbitrarily assigned a value of 0.D. Whole-cell lysates were prepared and analyzed by ELISA for GSK-3β (pSer9). Cells incubated for 1 hour with the GSK-3β inhibitor, LiC1 (10 mM), served as positive control. Results (n=3) are presented as the mean normalized GSK-3β (pSer9) concentration (Units/mg total protein)±SD, relative to non-treated samples, which were arbitrarily assigned a value of 0. * vs. non-treated (vehicle).

It generally is believed that tau phosphorylation will be affected accordingly. Generally, phosphorylation increases the activity of the kinases studied, with the exception of GSK-3β, which is inhibited. RA-SY5Y treated with leptin or AICAR did not significantly ($p>0.05$) alter phosphorylation

TABLE 1

Regulation of tau phsphorylation by kinases/phosphatases in RA–SY5Y

Figure 8A:
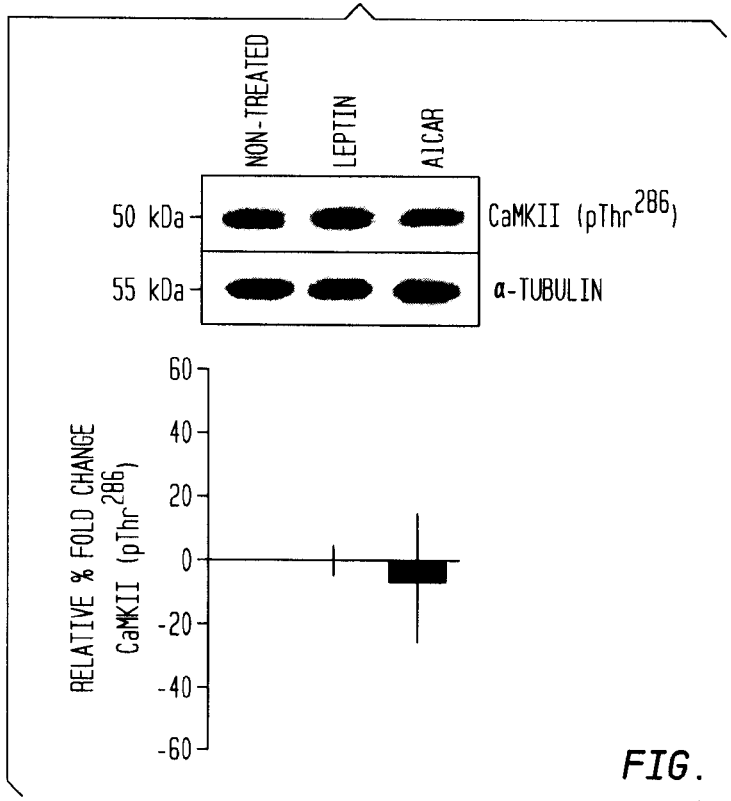
FIG. 8 shows the effect of leptin and AICAR on tau-specific kinase activation in RA-SY5Y. RA-SY5Y were treated with leptin (1600 ng/ml), AICAR (2 mM) or non-treated (vehicle), and phosphorylation of (A) CaMKII (pThr286), (B) PKA (pThr197) and (C) GSK-3β (pSer9) were measured by immunoblot.
Figure 8B:
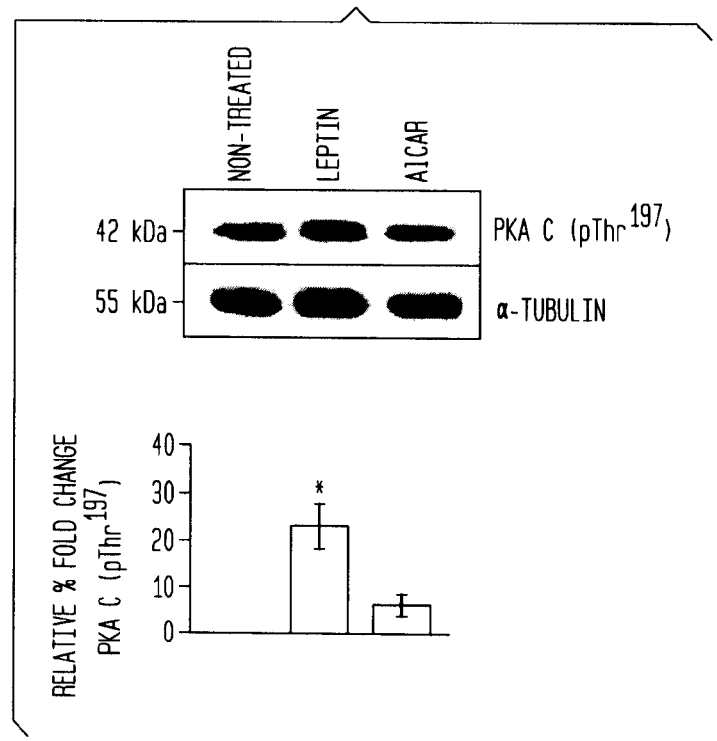
Figure 8C:
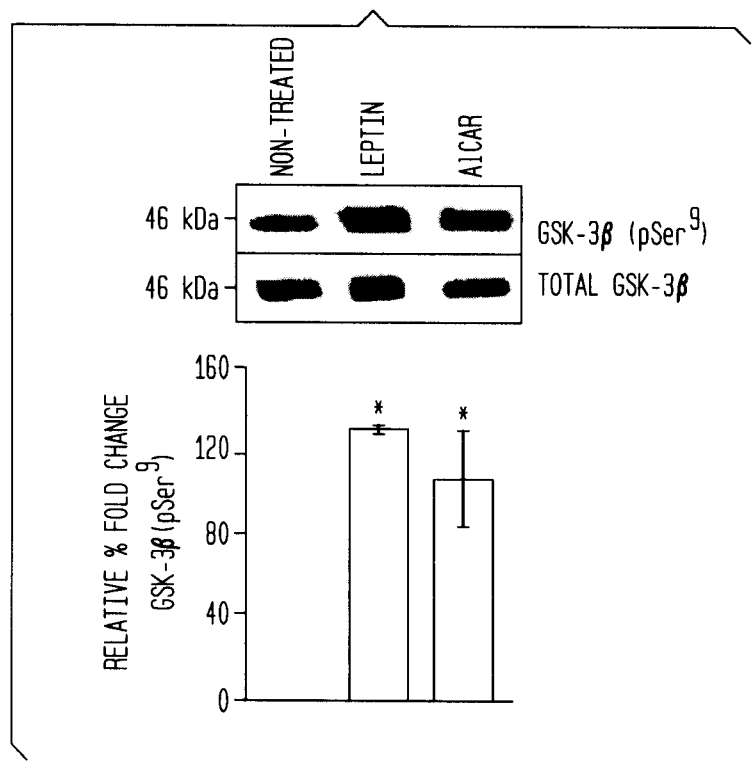
Figure 8D:
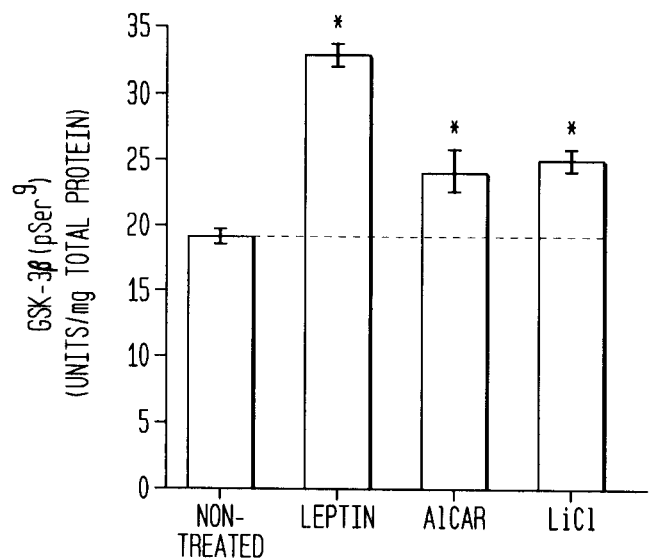

| Phopho-epitope | Treatment | | | | | | | | | |
|---|---|---|---|---|---|---|---|---|---|---|
| | Vehicle | Leptin | AICAR | C2 ceramide | Myr-AIP† | N6A4S† | FNG† | SP600125† | KT5720† | LiCl† |
| pSer$^{396}$ | 0 | −53 + 15* | −68 ± 6* | 36 + 19 | −34 ± 7* | −18 + 9 | 35 + 14 | −5 ± 9 | −60 + 9* | −61 ± 4* |
| PHF-1 | 0 | −44 + 8* | −26 + 4* | −32 + 12 | −43 + 10* | 50 ± 28 | 73 + 13* | 21 + 13 | −25 + 5* | −38 + 4* |
| AT8 | 0 | −48 ± 6* | −27 + 6* | −10 + 7 | −4 + −29 | −11 + 20 | −33 + 27 | −40 + 32 | −25 + 11 | −79 ± 11* |
| pSer$^{181}$ | 0 | −55 + 9* | −64 + 13* | −9 ± 6 | −30 + 17 | −31 + 15 | −34 + 18 | −77 + 5* | −54 + 22 | −75 + 11* | where † = a kinase inhibitor.

of CaMKII compared to non-treated cells (FIG. 8A), and only leptin was able to significantly (p<0.05) increase PKA phosphorylation (FIG. 8B, middle bar). However, both treatments significantly (p<0.05) increased GSK-3β phosphorylation at $Ser^9$ compared to control (FIG. 8C, white bars). These findings were confirmed by ELISA, which showed a significant (p<0.05) increase in the amount of GSK-3β ($pSer^9$) induced by leptin (FIG. 8D, second bar from left) and AICAR (second bar from right). This increase was at/or above levels observed with LiC1, a known GSK-3β inhibitor (far right bar). Thus, leptin appears to reduce phosphorylation of tau through the inhibition of GSK-3β.

Example 2.3

Leptin and AICAR Regulate Tau Phosphorylation Via GSK-3β

The above experiments were repeated while modulating GSK-3β activity to determine whether leptin and/or AICAR require GSK-3β to regulate phosphorylation of tau. Enzyme inhibitors or siRNA technology was used to block GSK-3β activity. FIG. 9 shows that leptin and AICAR modulate tau phosphorylation via a GSK-3,3-dependent mechanism. (A) RA-SY5Y were transiently transfected with GSK-3,3-specific siRNA, or untransfected lane (1), and later treated with leptin (1600 ng/ml—lane 4), AICAR (2 mM—lane 5) or no treatment (vehicle—lane 3). Cells transfected with fluorescein-conjugated control siRNA (lane 2) were used to assess transfection efficiency and served as negative control. Whole-cell lysates were prepared and analyzed by immunoblot with GSK-3,3-specific (panel I) or phosphorylated tau-specific antibodies (pSer396, PHF-1, AT8 or pSer181; panel II). Membranes were stripped and re-probed with total GSK-3β (panel I) or total tau (panel II) antibodies for normalization. Representative blots are shown (n=3). Normalized tau bands were analyzed by densitometry and results (panels III-IV) are presented as the mean±SD percent fold change, relative to negative control samples, which were arbitrarily assigned a value of 0. (B) RA-SY5Y were transiently transfected with a GSK-3β full-length cDNA expression vector, or untransfected (lane 1), and later treated with leptin (1600 ng/ml—lane 4), AICAR (2 mM—lane 5) or no treatment (vehicle—lane 3). Cells transfected with empty expression vector (lane 2) served as negative control. Whole-cell lysates were prepared, analyzed and normalized as in A. Results (n=3) are presented as in A. * vs. negative control (lane 2); ** vs. GSK-3β-overexpressing cells treated with vehicle (lane 3).

Figure 9A:
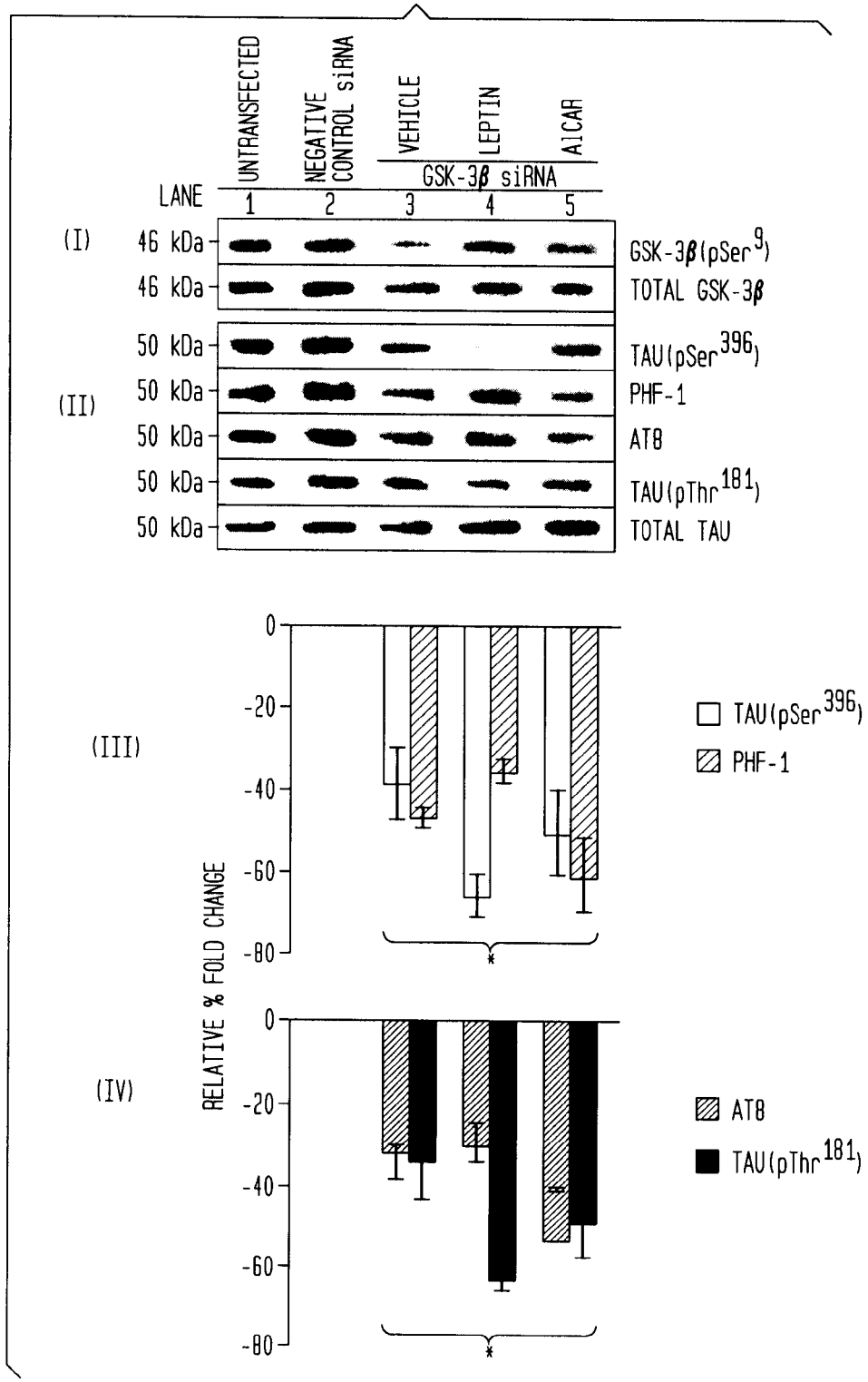
FIG. 9 shows leptin and AICAR modulate tau phosphorylation via a GSK-3β-dependent mechanism. (A) RA-SY5Y transiently transfected with GSK-3β-specific siRNA, or untransfected lane (1), and later treated with leptin (1600 ng/ml—lane 4), AICAR (2 mM—lane 5) or no treatment (vehicle—lane 3). Cells transfected with fluorescein-conjugated control siRNA (lane 2) were used to assess transfection efficiency and served as negative control. Whole-cell lysates were prepared and analyzed by immunoblot with GSK-3β-specific (panel I) or phosphorylated tau-specific antibodies (pSer396, PHF-1, AT8 or pSer181; panel II). Membranes were stripped and re-probed with total GSK-3β (panel I) or total tau (panel II) antibodies for normalization. (B) RA-SY5Y were transiently transfected with a GSK-3β full-length cDNA expression vector, or untransfected (lane 1), and later treated with leptin (1600 ng/ml—lane 4), AICAR (2 mM—lane 5) or no treatment (vehicle—lane 3). Cells transfected with empty expression vector (lane 2) served as negative control. Whole-cell lysates were prepared, analyzed and normalized as in A. * vs. negative control (lane 2); ** vs. GSK-3β-overexpressing cells treated with vehicle (lane 3).

GSK-3β was overexpressed in neuronal cells using a mammalian expression vector with a strong promoter (FIG. 9) to increase activity. Specifically, RA-SY5Y cells were transiently transfected with GSK-3β-specific siRNA, and then treated with leptin, AICAR or vehicle (FIG. 9A). These were compared to cells transfected with control siRNA or to cells that were not transfected. Cells were assayed for total GSK-3β (active plus inactive forms) expression and phosphorylated GSK-3β (inactive form) to confirm knockdown of the specific protein (FIG. 9A, panel I) and its effect on kinase activity, as measured by the levels of different forms of phosphorylated tau (FIG. 9A, panels II-IV). GSK-3β knockdowns (panel I, lanes 3-5) showed a significant (p<0.05) decrease in tau phosphorylation at all sites (panels II-IV, lanes 3-5) compared to controls (lanes 1-2). In the presence of leptin (but not AICAR) increased phosphorylation of the residual GSK3β (panel I, lane 4) after knockdown, was associated with further decrease in the phosphorylation of $pSer^{396}$ tau (panels lane 4 white bar) and $pThr^{181}$ tau (panels II and IV, lane 4 black bar), but this was not significant.

Figure 15:
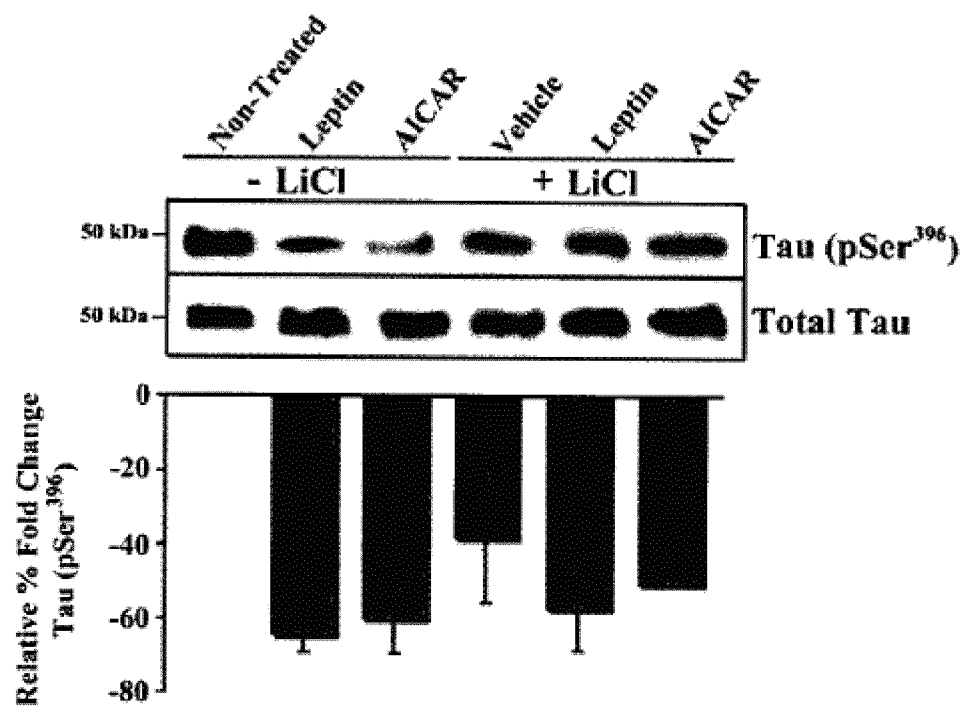
FIG. 15 shows that leptin and AICAR do not significantly reduce tau phosphorylation in RA-SY5Y cells incubated with lithium. RA-SY5Y were incubated with or without lithium (10 mM), in the presence of leptin (1600 ng/ml), AICAR (2 mM) or no additional treatment (vehicle), and phosphorylation of tau was measured.
Figure 16:
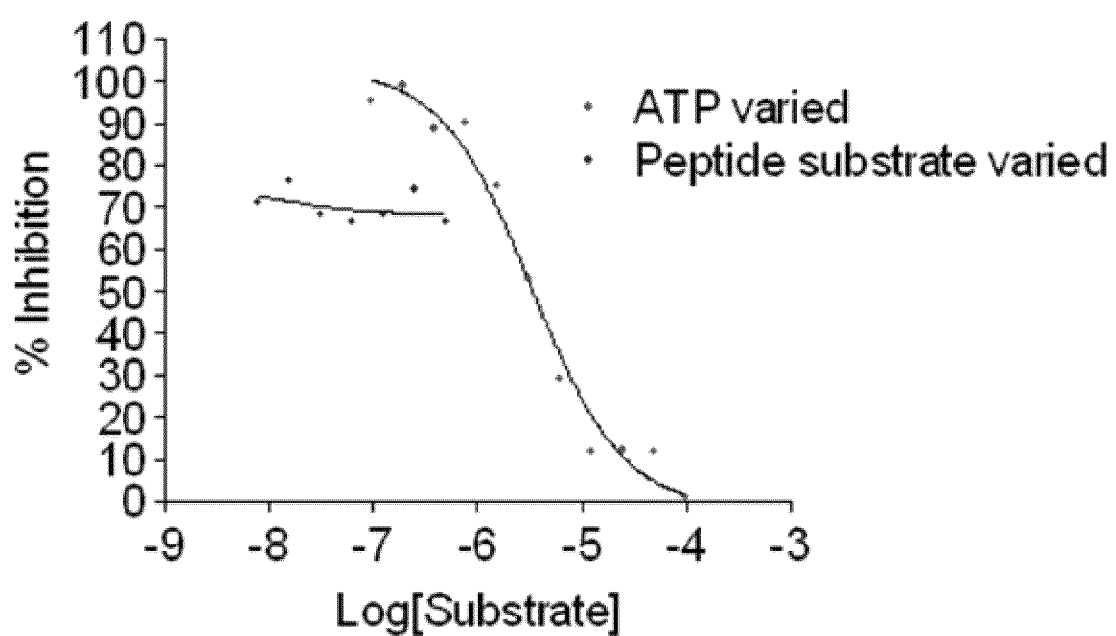
FIG. 16 shows a plot of illustrative data from a model for assessing a mode of inhibition of an enzyme.

Similar results were obtained following ablation of GSK-3β activity by LiC1 treatment. FIG. 15 shows that leptin and AICAR do not significantly reduce tau phosphorylation in RA-SY5Y incubated with lithium. RA-SY5Y were incubated with or without lithium (10 mM), in the presence of leptin (1600 ng/ml), AICAR (2 mM) or no additional treatment (vehicle), and phosphorylation of tau was measured. Whole-cell lysates were prepared and analyzed by immunoblot with a phosphorylated tau-specific antibody (pSer396). Membranes were stripped and re-probed with total tau antibody for normalization. Representative blots are shown, n=3. Normalized bands were analyzed by densitometry and results are presented as the mean±SD percent fold change, relative to non-treated samples, which were arbitrarily assigned a value of 0.

Figure 9B:
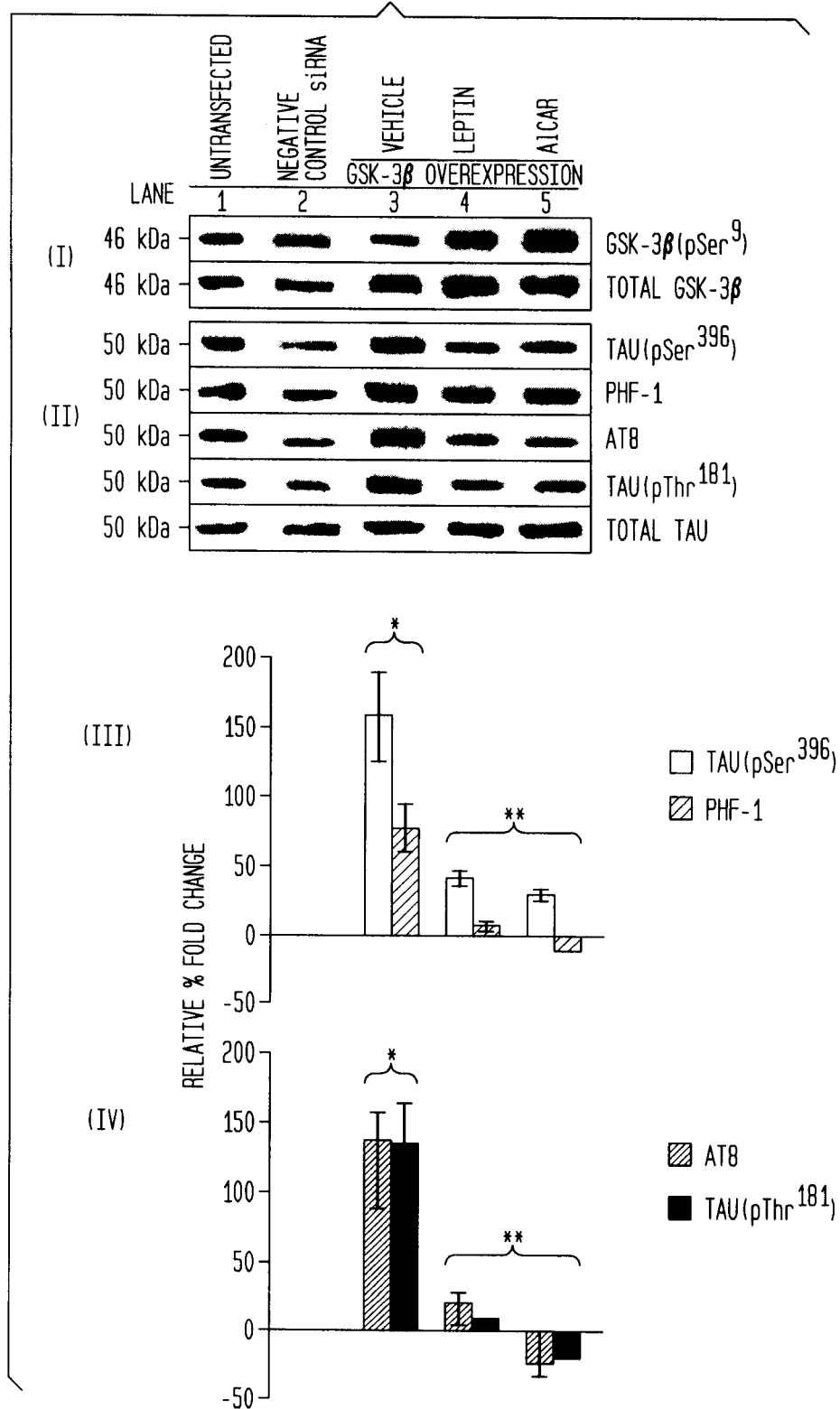

Additionally, studies with RA-SY5Y cells overexpressing GSK-3β provided further mechanistic insight. (FIG. 9B). Cells were transiently transfected with a GSK-3β expression vector, and significantly higher levels of the corresponding protein were produced (panel I, lane 3) compared to untransfected cells or cells transfected with empty vector (panel I, lanes 1-2). Leptin or AICAR treatment of these cells significantly increased the levels of GSK-3β phosphorylation ($pSer^9$) (panel I, lanes 4-5) compared to vehicle and transfection controls. Overexpression of GSK-3β was coincident with an increase of all phospho-tau sites examined (panels II-IV, lane 3), however both leptin and AICAR treatments significantly (p<0.05) reduced these increases (panels II-IV, lanes 4-5). This effect may be due to increasing levels of inactive GSK-3β.

In summary, these findings suggest that leptin and its downstream signaling protein, AMPK (through AICAR), reduce phosphorylation of tau by inhibiting GSK-3β.

Example 2.4

Leptin and AICAR in Other Cell Types

Figure 10:
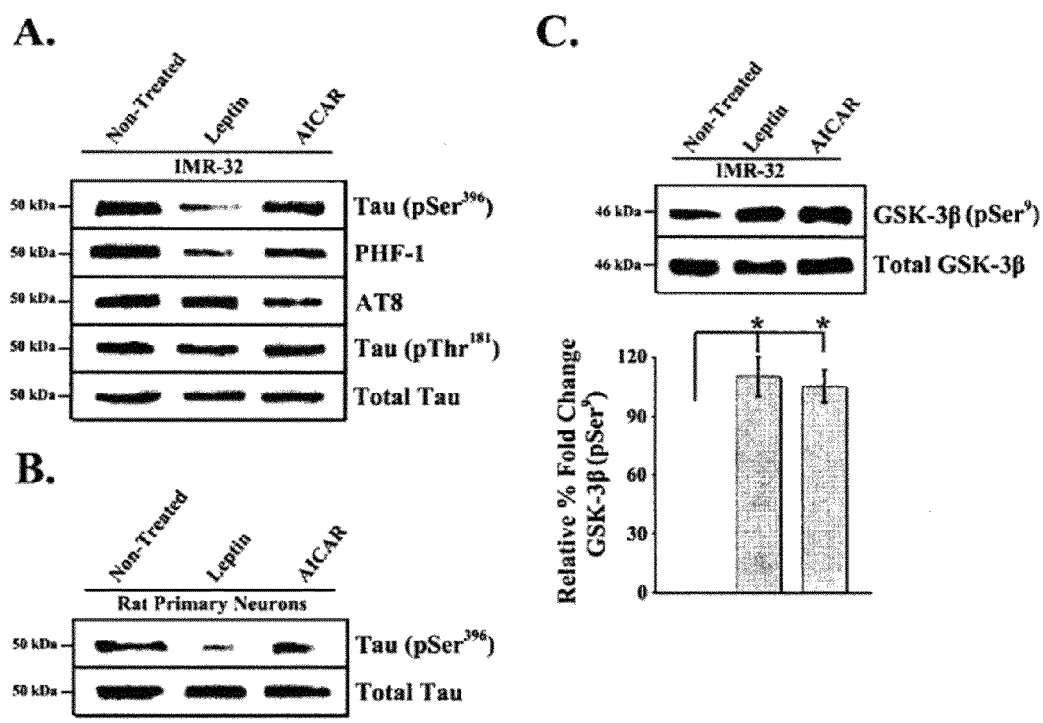
FIG. 10 shows effects of leptin and AICAR in other neuronal models. (A) Human IMR-32 cells; (B) rat primary cortical neurons; (C) IMR-32 cells were treated with leptin (1600 ng/ml), AICAR (2 mM) or non-treated (vehicle). Whole-cell lysates were prepared and analyzed by immunoblot with phosphorlyated tau-specific antibodies (pSer396, PHF-1, AT8 or pSer181). IMR-32 cells (C) were treated as in (A) and phosphorylation of GSK-3β (Ser9) was measured by immunoblot. * vs. non-treated (vehicle).

Leptin and AICAR were studied in other neuronal cells. FIG. 10 shows the effects of leptin and AICAR in other neuronal cell models. (A) Human IMR-32 cells and (B) rat primary cortical neurons were treated with leptin (1600 ng/ml), with AICAR (2 mM) or with vehicle (non-treated control). Whole-cell lysates were prepared and analyzed by immunoblot with phosphorlyated tau-specific antibodies (pSer396, PHF-1, AT8 or pSer191). Membranes were stripped and re-probed with total tau antibody for normalization. Representative blots are shown (n=3). Semi-quantative band density analyses are presented in Table 2. (C) IMR-32 cells were treated as in (A) and phosphorylated of GSK-3β (Ser9) was measured by immunoblot. Membranes were stripped and re-probed with total GSK-3β for normalization. Representative blots are shown (n=3). Normalized bands were analyzed by densitometry and results are presented as the mean±SD percent fold change, relative to non-treated samples, which were arbitrarily assigned a value of 0. * vs. non-treated (vehicle).

RA-induced, human neuroblastoma IMR-32 cells (FIG. 10A) and rat primary cortical neurons (FIG. 10B) were treated with leptin, AICAR or no treatment. Again, leptin and AICAR induced a significant (p<0.05) decrease in tau phosphorylation at all sites (panels II-IV, lanes 3-5) compared to vehicle-treated cells (Table 2). In Table 2, normalized tau bands from FIG. 10 were analyzed by densitometry and results are presented as the mean±SD percent fold change, relative to vehicle, which were arbitrarily assigned a value of 0; * vs. vehicle.

TABLE 2

Relative tau phosphorylation in treated neuronal cultures

| Cell Type | Phospho- Epitope | Treatment | | |
|---|---|---|---|---|
| | | Vehicle | Leptin | AICAR |
| IMR-32 | pSer$^{396}$ | 0 | −69 ± 7* | −25 ± 2* |
| | PHF-1 | 0 | −63 ± 8* | −29 ± 1* |
| | AT8 | 0 | −26 ± 8* | −48 ± 6* |
| | PSer$^{181}$ | 0 | −36:0* | −29 ± 9* |
| Rat 1° Neurons | pSer$^{396}$ | 0 | −95 ± 3* | −39 ± 1* |

To confirm that the effect of leptin and AICAR on tau phosphorylation in other models is mechanistically similar to RA-SY5Y (FIG. 8 and FIG. 9), phosphorylation of GSK-3β was measured in differentiated IMR-32 cells (FIG. 10C). Leptin and AICAR significantly (p<0.05) increased GSK-3β phosphorylation compared to vehicle control (gray bars).

These findings suggest that leptin and AICAR consistently modulate tau through inactivation of GSK-3β, as observed in RA-SY5Y cells and also in differentiated IMR-32 cells (FIG. 10).

Example 2.5

Upstream Signaling Events Regulating Tau Phosphorylation

A role for AMPK upstream of GSK-3β inactivation was examined; more specifically, the upstream signaling events leading from leptin's binding to its receptor to inactivation of GSK-3β. FIG. 11 shows that leptin and AICAR regulate tau phosphorylation via overlapping signaling pathways. (A) RASY5Y cells were incubated with inhibitors to known downstream effectors of leptin signaling (STAT3, AMPK, PI3K, Akt, p38) in the presence of leptin (1600 ng/ml—lanes 3-7), or non-treated (vehicle—lane 1). Cells treated with leptin alone served as positive control (lane 2). Whole-cell lysates were prepared and analyzed by immunoblot with phosphorylated tau-specific antibodies (pSer396, PHF-1, AT8 or pSer181). Membranes were stripped and re-probed with total tau antibody for normalization. Representative blots are shown, n=3. Normalized tau bands were analyzed by densitometry and results are presented as the mean±SD percent fold change, relative to non-treated samples, which were arbitrarily assigned a value of 0. (B) Whole-cell lysates from (A), except those which did not significantly alter tau phosphorylation compared to leptin alone (STAT3, phosphotidylinositol-3 kinase (PI3K)), were analyzed by immunoblot with phosphorylated GSK-3P-specific antibody. Membranes were stripped and re-probed with total GSK-3β for normalization. Results (n=3) are presented as in (A).(C) Cells treated with leptin, AICAR or vehicle), and activation of the signaling molecules (Jak2, AMPK, p38, Akt) implicated in regulating tau phosphorylation were examined by immunoblot using phosphorylation-specific antibodies. Membranes were stripped and re-probed with a-tubulin antibody for normalization. Representative blots are shown, n=3. * vs. non-treated (vehicle—lane 1); ** leptin alone (lane 2)

Figure 11A:
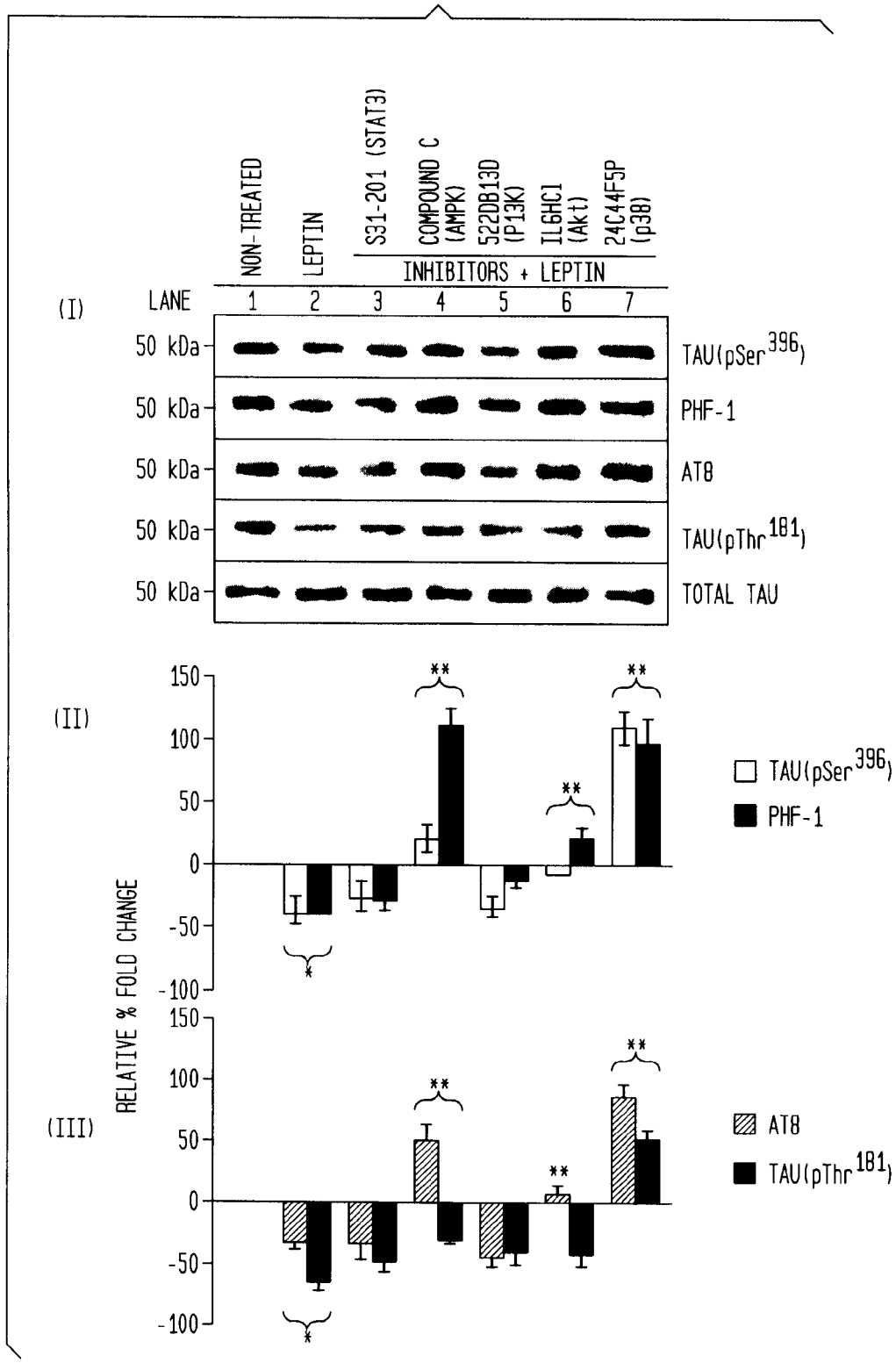
FIG. 11 shows leptin and AICAR regulate tau phosphorylation via overlapping signaling pathways. (A) RASY5Y were incubated with inhibitors to known downstream effectors of leptin signaling (STAT3, AMPK, PI3K, Akt, p38) in the presence of leptin (1600 ng/ml—lanes 3-7), or non-treated (vehicle—lane 1). Cells treated with leptin alone served as positive control (lane 2). Whole-cell lysates were prepared and analyzed by immunoblot with phosphorylated tau-specific antibodies (pSer396, PHF-1, AT8 or pSer181). (B) Whole-cell lysates from (A), except those which did not significantly alter tau phosphorylation compared to leptin alone (STAT3, phosphotidyl-inositol-3 kinase (PI3K)), were analyzed by immunoblot with phosphorylated GSK-3P-specific antibody. (C) Cells were treated with leptin, AICAR or non-treated (vehicle), and activation of the signaling molecules (Jak2, AMPK, p38, Akt) implicated in regulating tau phosphorylation were examined by immunoblot using phosphorylation-specific antibodies. Membranes were stripped and re-probed with a-tubulin antibody for normalization. * vs. non-treated (vehicle—lane 1); ** leptin alone (lane 2)
Figure 11B:
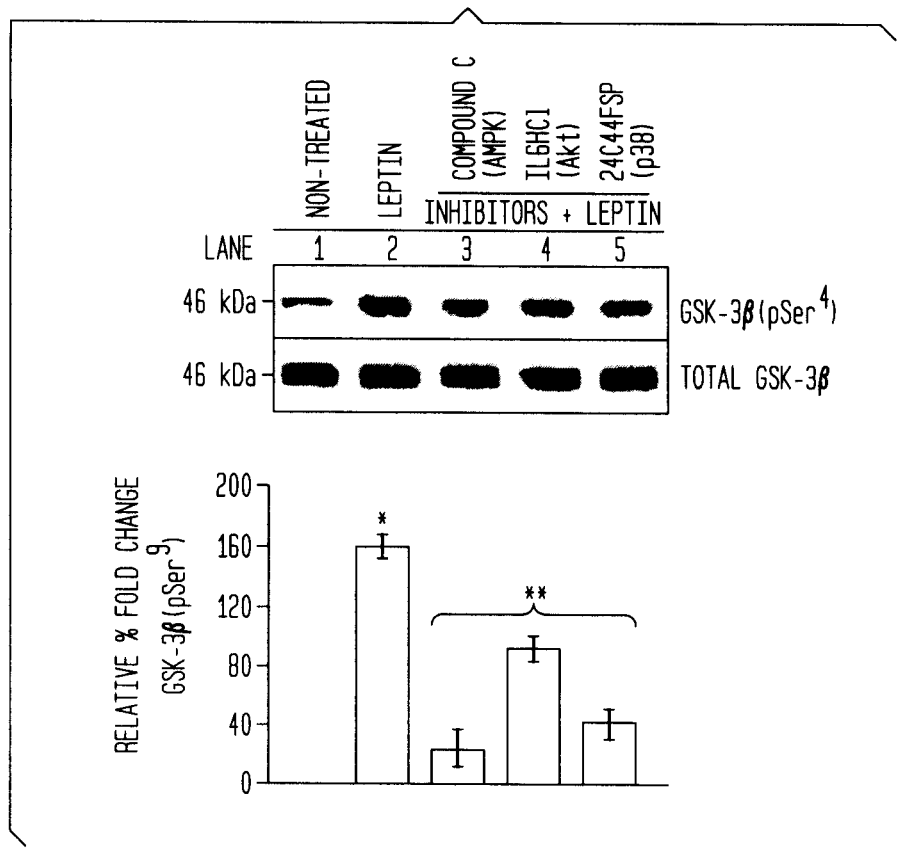
Figure 11C:
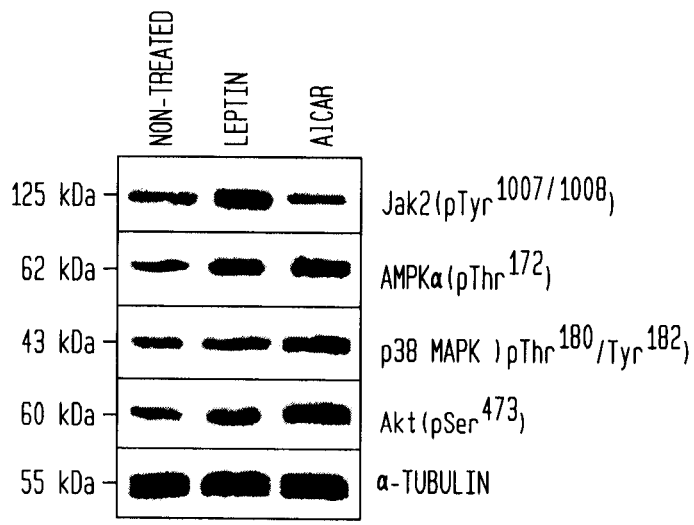

RA-SY5Y cells were treated with leptin in the presence or absence of inhibitors to known signaling proteins activated following leptin's binding to its receptor (for concentrations see (Section 2.1, Materials and Method, supras) (FIG. 11A). Phosphorylation of tau at several different epitopes again served as the experimental endpoint. Comparisons were made relative to cells treated with leptin alone or vehicle. Inhibitors of AMPK, Akt (protein kinase B) or p38 MAP kinase significantly (p<0.05) impeded leptin's ability to reduce tau phosphorylation (panels I-III, lanes 4, 6 and 7) and, in some instances, increased phosphorylation compared to vehicle-treated control (i.e., panel II, lane 4 gray bar). Similar data were obtained from cells treated with specific inhibitors in the absence of leptin (data not shown).

The involvement of AMPK, Akt and/or p38 in leptin-mediated GSK-3β inactivation (FIG. 11B) was studied Inhibition of AMPK, Akt or p38 MAP kinase (lanes 3-5) significantly (p<0.05) reversed the leptin-induced increase of GSK-3β phosphorylation (lane 2). Cells treated with specific inhibitors in the absence of leptin did not significantly affect GSK-3β phosphorylation compared to vehicle control (data not shown).

The phosphorylation of the above kinases following leptin treatment (FIG. 11C) was studied. Leptin treatment of RA-SY5Y cells resulted in the phosphorylation of all examined kinases (middle lane). Similar results were observed for the AMPK activator, AICAR, with the exception of Janus kinase 2 (Jak2) (top row, right lane), thus confirming that AMPK is downstream of Jak2 in the signaling cascade.

In summary, the data provide substantial information regarding a signaling pathway linking leptin's binding to its receptor and tau phosphorylation. This pathway appears to be regulated by several principal kinases, including, but not limited to, e AMPK, p38 MAP kinase, Akt and GSK-3β.

Example 2.6

Leptin Regulates All Release via AMPK

The interconnection of pathways leading to Aβ production and tau phosphorylation, both of which are modulated by leptin, was studied.

Figure 12:
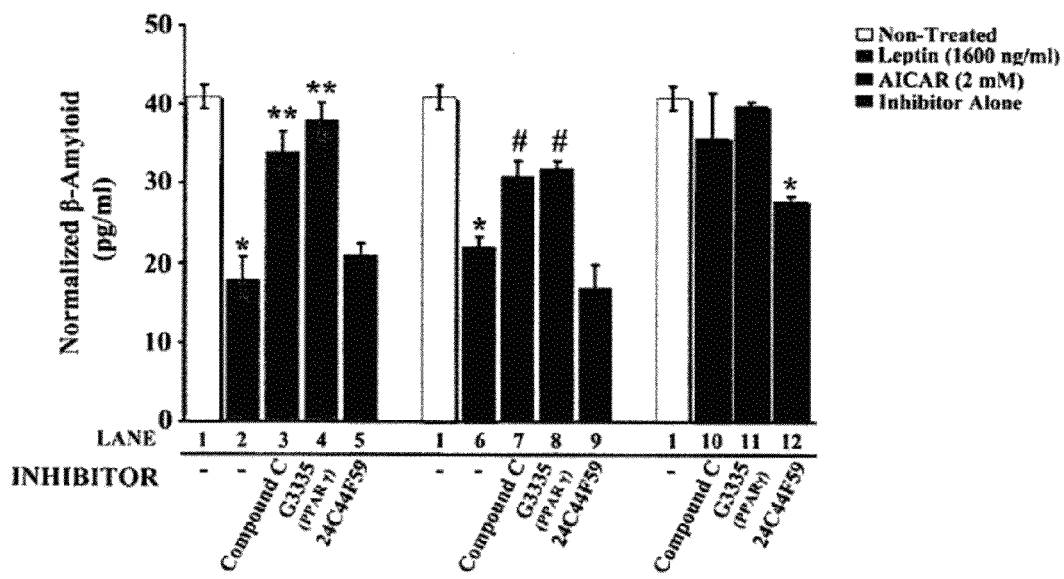
FIG. 12 shows leptin and AICAR regulate AP production via overlapping signaling pathways. (A) RA-SY5Y were treated for 6 hrs with leptin (1600 ng/ml—lane 2), AICAR (2 mM—lane 6) and/or inhibitors to each of the following signaling proteins AMPK (lanes 3 and 7), PPARy (lanes 4 and 8) or p38 (lanes 5 and 9). Non-treated (vehicle—lane 1) cells or cells treated with inhibitor alone (lanes 10-12) served as control. Culture media was collected and assayed for AP(1-40) by ELISA. (B) RA-SY5Y were treated with leptin, AICAR (2 mM) or non-treated (vehicle), and levels of PPARy were measured by immunoblot. Membranes were stripped and re-probed with α-tubulin antibody for normalization. * vs. non-treated (vehicle—lane 1); ** vs. leptin alone (lane 2); # vs. AICAR alone (lane 6)
Figure 12:
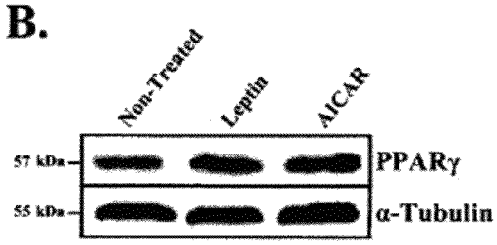

The roles of peroxisome proliferator-activated receptor γ (PPARγ), p38 and the leptin-AMPK pathway in regulating Aβ release) was studied. FIG. 12 shows that leptin and AICAR regulate AP production via overlapping signaling pathways. (A) RA-SY5Y were treated for 6 hrs with leptin (1600 ng/ml—lane 2), AICAR (2 mM—lane 6) and/or inhibitors to each of the following signaling proteins AMPK (lanes 3 and 7), PPARγ (lanes 4 and 8) or p38 (lanes 5 and 9). Non-treated (vehicle—lane 1) cells or cells treated with inhibitor alone (lanes 10-12) served as control. Culture media was collected and assayed for AP(1-40) by ELISA. Results were normalized to total protein in cell lysates and are presented as the mean AP concentration (pg/ml)±SD. (B) RA-SY5Y were treated with leptin, AICAR (2 mM) or non-treated (vehicle), and levels of PPARy were measured by immunoblot. Membranes were stripped and re-probed with a-tubulin antibody for normalization. Representative blots are shown, n=3. * vs. non-treated (vehicle—lane 1); ** vs. leptin alone (lane 2); # vs. AICAR alone (lane 6)

A significant (p<0.05) decrease in soluble Aβ was observed in cells treated with leptin (lane 2) or AICAR (lane 6). These effects were negated by co-treatment with AMPK (lanes 3 and 7) or PPARγ (lanes 4 and 8) inhibitors, but not p38 inhibitor (lanes 5 and 9).

Additionally, cells treated with leptin or AICAR for 6 hours increased expression of PPARγ compared to non-treated controls (FIG. 12B), thereby verifying a link between leptin, AMPK and PPARγ.

These results show that Aβ production can be modulated by AMPK, an energy regulator linked to phosphorylation of tau.

Example 2.7

Tau and Aβ Pathways Do Not Overlap Downstream of AMPK

Figure 13A:
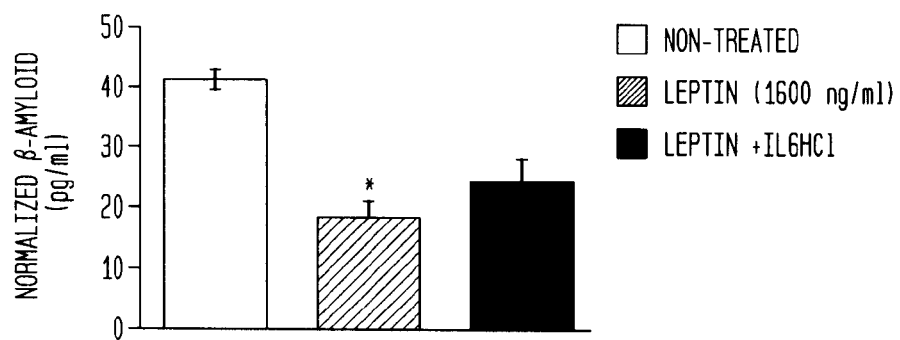
FIG. 13 shows leptin and AICAR signaling pathways downstream of AMPK do not mediate both tau phosphorylation and Aβ production. (A) RA-SY5Y treated for 6 hrs with leptin (1600 ng/ml) alone or in the presence of Akt inhibitor (1L6HCI). Non-treated (vehicle) cells served as control. Culture media was collected and assayed for AP(1-40) by ELISA. (B) RA-SY5Y treated for 6 hrs with leptin (1600 ng/ml) alone or in the presence of PPARy inhibitor (G3335). Non-treated (vehicle) cells served as control. Whole-cell lysates were prepared and analyzed by immunoblot with phosphorylated tau-specific antibodies (pSer396, PHF-1, AT8 or pSer181). (C) Cartoon depicting the signaling pathways activated by leptin and AICAR in RA-SY5Y. Activation of AMPK by either leptin or AICAR reduces both AP production and tau phosphorylation. However, the signaling pathways downstream of AMPK act independently to mediate tau- or AP-specific effects; * vs. non-treated (vehicle)
Figure 13B:
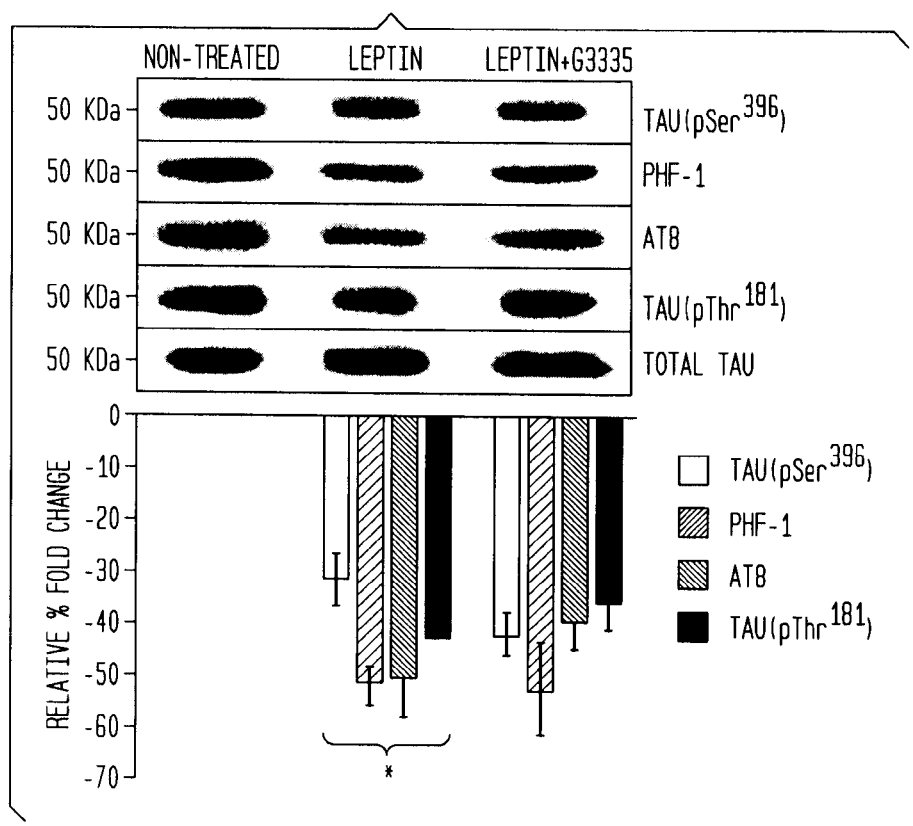
Figure 13C:
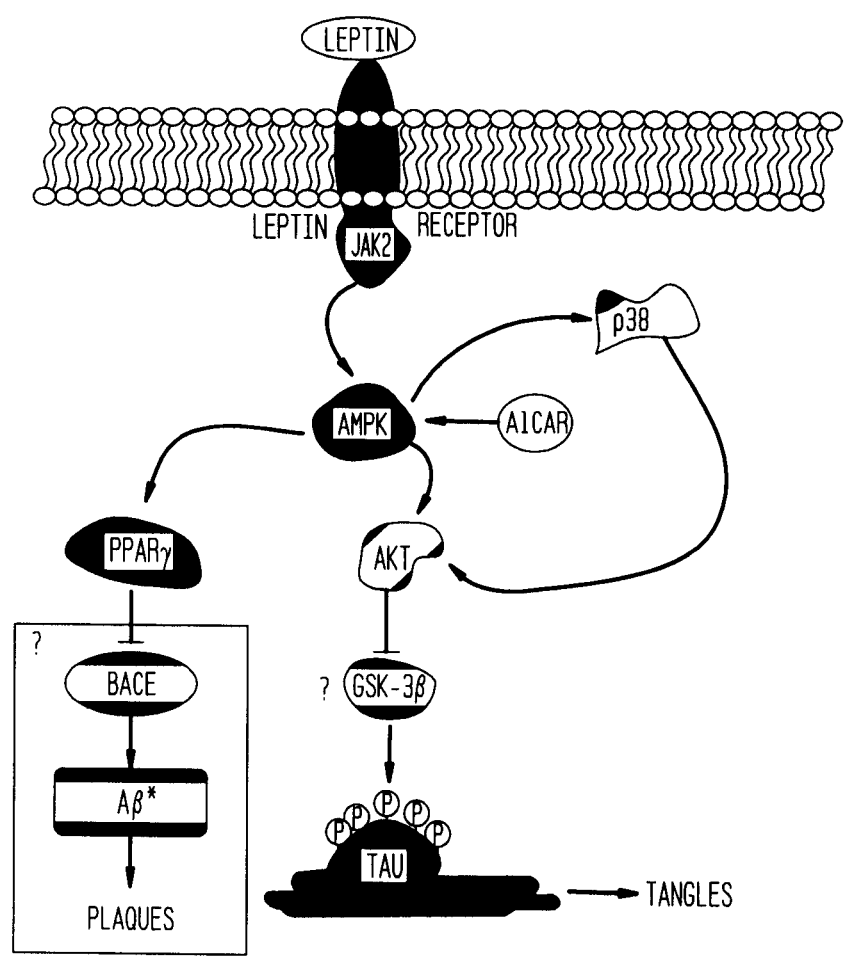

The overlap between the leptin-mediated tau and Aβ pathways beyond AMPK (FIG. 13) was studied. FIG. 13 shows that leptin and AICAR signaling pathways downstream of AMPK do not mediate both tau phosphorylation and AP production. (A) RA-SY5Y were treated for 6 hrs with leptin (1600 ng/ml) alone or in the presence of Akt inhibitor (1L6HCI). Non-treated (vehicle) cells served as control. Culture media was collected and assayed for AP(1-40) by ELISA. Results were normalized to total protein in cell lysates and are presented as the mean AP concentration (pg/ml)±SD. (B) RA-SY5Y were treated for 6 hrs with leptin (1600 ng/ml) alone or in the presence of PPARy inhibitor (G3335). Non-treated (vehicle) cells served as control. Whole-cell lysates were prepared and analyzed by immunoblot with phosphorylated tau-specific antibodies (pSer396, PHF-1, AT8 or pSer181). Membranes were stripped and re-probed with total tau antibody for normalization. Representative blots are shown, n=3. Normalized tau bands were analyzed by densitometry and results are presented as the mean±SD percent fold change, relative to non-treated samples, which were arbitrarily assigned a value of 0. (C) Cartoon depicting the signaling pathways activated by leptin and AICAR in RA-SY5Y. Activation of AMPK by either leptin or AICAR reduces both AP production and tau phosphorylation. However, the signaling pathways downstream of AMPK act independently to mediate tau- or AP-specific effects; * vs. non-treated (vehicle)

RA-SY5Y cells were treated with leptin in the presence or absence of Akt (FIG. 13A) or PPARγ (FIG. 13B) inhibitors. AICAR increased phosphorylation of Akt (FIG. 11C) and expression of PPARγ (FIG. 12B), however, inhibition of Akt was unable to significantly (p>0.05) reverse the leptin-induced reduction of soluble Aβ release (FIG. 13A, dark gray bar). Likewise, inhibition of PPARγ did not significantly (p>0.05) reverse the leptin induced reduction of tau phosphorylation at all examined sites (FIG. 13B, right set of bars). Thus, further components shared by the two pathways were not identified.

In summary, leptin regulates phosphorylation of tau and Aβ production and release through distinct signaling pathways in neuronal cells. These pathways diverged downstream of leptin-mediated AMPK activation to produce specific effects.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for improving cognitive function of an Alzheimer's Disease subject suffering from at least one symptom of cognitive impairment comprising administering to the Alzheimer's Disease subject suffering from the at least one symptom of cognitive impairment a therapeutic amount of a leptin composition, wherein the leptin composition comprises
    (i) a leptin as a first therapeutic agent;
    (ii) a second therapeutic agent, wherein the second therapeutic agent comprises at least one kinase inhibitor of Glycogen Synthase Kinase-3 beta (GSK- 3β); and
    (iii) a pharmaceutically acceptable carrier,
    wherein the therapeutic amount of the leptin composition is effective to improve cognitive function of the subject by reducing
    (1) the extracellular accumulation of amyloid beta in brain tissue, relative to the accumulation of amyloid beta in brain tissue of a subject treated with placebo,
    (2) the amount of abnormally phosphorylated tau in brain, relative to the amount of abnormally phosphorylated tau observed in a subject treated with placebo, and
    (3) the accumulation of neurofibrillary tangles in brain tissue, relative to the accumulation of neurofibrillary tangles observed in a subject treated with placebo,
    wherein the symptom of cognitive impairment is further characterized
    (1) as an impairment in memory, an impairment in language skill, an impairment in perceptual skills, an impairment in attention, an impairment in constructive ability, an impairment in orientation ability, an impairment in problem solving ability, an impairment in functional ability, or a combination thereof, as compared to a healthy subject, and
    (2) associated with (a) the extracellular accumulation of amyloid beta in brain tissue, (b) the aberrant pattern of phosphorylation of a tau protein in brain tissue, and (c) the accumulation of neurofibrillary tangles in brain tissue due to Alzheimer's disease.

2. The method according to claim 1, wherein the abnormal phosphorylation of tau is at least one phosphorylation site selected from the group consisting of $Ser^{181}$, $Ser^{202}$, $Thr^{205}$, $Ser^{212}$, $Ser^{214}$, $Ser^{231}$, $Ser^{235}$, $Ser^{396}$ and $Ser^{404}$.

3. The method according to claim 1, wherein the at least one kinase inhibitor of Glycogen Synthase Kinase-3 beta (GSK-3β) is selected from the group consisting of Lithium Chloride, 6-bromoindirubin-3'-oxime ((2'Z,3'E)-6-bromoindirubin-3'-oxime, 3-(2,4-dichlorophenyl)-4-(1-methyl-1 H-indol-3-yl)-1 H-pyrrole-2,5-dione, and TDZD-8 (4-Benzyl-2-methyl-1,2,4-thiadiazolidine-3,5-dione-8).

4. The method according to claim 1, wherein the therapeutic amount of the leptin in the leptin composition is an amount from about 0.0001 mg/kg body weight to about 100 g/kg body weight.

* * * * *